US012661385B2

(12) United States Patent
Ahmed et al.

(10) Patent No.: US 12,661,385 B2
(45) Date of Patent: Jun. 23, 2026

(54) MODULATION OF mTORCI ACTIVITY AND AUTOPHAGY VIA CIB2-RHEB INTERACTION

(71) Applicants: Zubair M. Ahmed, Ellicott City, MD (US); Saumil Sethna, Baltimore, MD (US); Saima Riazuddin, Ellicott City, MD (US)

(72) Inventors: Zubair M. Ahmed, Ellicott City, MD (US); Saumil Sethna, Baltimore, MD (US); Saima Riazuddin, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 1007 days.

(21) Appl. No.: 17/264,939

(22) PCT Filed: Aug. 1, 2019

(86) PCT No.: PCT/US2019/044745
§ 371 (c)(1),
(2) Date: Feb. 1, 2021

(87) PCT Pub. No.: WO2020/028717
PCT Pub. Date: Feb. 6, 2020

(65) Prior Publication Data
US 2021/0290727 A1     Sep. 23, 2021

Related U.S. Application Data

(60) Provisional application No. 62/713,044, filed on Aug. 1, 2018.

(51) Int. Cl.
| | |
|---|---|
| *A61K 38/17* | (2006.01) |
| *A61K 31/11* | (2006.01) |
| *A61K 35/76* | (2015.01) |
| *A61K 38/46* | (2006.01) |
| *A61P 27/02* | (2006.01) |
| *A61P 35/00* | (2006.01) |
| *C07K 14/47* | (2006.01) |
| *C12N 7/00* | (2006.01) |
| *C12N 15/86* | (2006.01) |
| *A61K 48/00* | (2006.01) |

(52) U.S. Cl.
CPC .......... *A61K 38/1738* (2013.01); *A61K 31/11* (2013.01); *A61K 35/76* (2013.01); *A61K 38/465* (2013.01); *A61P 27/02* (2018.01); *A61P 35/00* (2018.01); *C07K 14/4728* (2013.01); *C12N 7/00* (2013.01); *C12N 15/86* (2013.01); *A61K 48/00* (2013.01); *C07K 2319/00* (2013.01); *C12N 2750/14143* (2013.01)

(58) Field of Classification Search
CPC .... A61K 38/1738; A61K 31/11; A61K 35/76; A61K 38/465; A61K 48/00; A61K 48/005; A61P 27/02; A61P 35/00; C07K 14/4728; C07K 2319/00; C07K 14/47; C12N 7/00; C12N 15/86; C12N 2750/14143; A01K 2217/075; A01K 2227/105; A01K 2267/0306
See application file for complete search history.

(56) References Cited

U.S. PATENT DOCUMENTS

| | | | | |
|---|---|---|---|---|
| 7,053,200 B1 * | 5/2006 | Zoghbi | .............. | C07K 14/4702 |
| | | | | 536/23.4 |
| 2009/0053189 A1 * | 2/2009 | Glimcher | ................ | A61P 19/08 |
| | | | | 506/10 |
| 2014/0068797 A1 * | 3/2014 | Doudna | ............... | C12N 15/907 |
| | | | | 435/375 |
| 2015/0240263 A1 * | 8/2015 | Holmes | ................ | C12N 15/907 |
| | | | | 424/94.6 |
| 2015/0258120 A1 * | 9/2015 | Zarnitsyn | ........... | A61K 31/4439 |
| | | | | 514/180 |
| 2017/0326254 A1 * | 11/2017 | Chen | .................... | A61K 9/0046 |
| 2018/0133327 A1 * | 5/2018 | Derouazi | ............. | A61K 38/177 |
| 2018/0369414 A1 * | 12/2018 | Stankovic | ............... | A61P 27/16 |
| 2019/0255192 A1 * | 8/2019 | Kirn | ....................... | C12N 15/86 |
| 2019/0275168 A1 * | 9/2019 | Wu | ...................... | C12N 15/113 |

OTHER PUBLICATIONS

Rong et al. "Novel and recurrent MYO7A mutations in Usher syndrome type 1 and type 2." PLOS One. May 15, 2014;9(5):e97808. (Year: 2014).*
Addo, E., Bamiro, O.A., Siwale, R. (2016). Anatomy of the Eye and Common Diseases Affecting the Eye. In: Addo, R. (eds) Ocular Drug Delivery: Advances, Challenges and Applications. Springer, Cham. https://doi.org/10.1007/978-3-319-47691-9_2 (Year: 2016).*
Riazuddin et al. "Alterations of the CIB2 calcium- and integrin-binding protein cause Usher syndrome type 1J and nonsyndromic deafness DFNB48." Nature Genetics vol. 44, pp. 1265-1271 (2012) (Year: 2012).*
Dricu, A. "Oncogenic Signalling of Growth Factor Receptors in Cancer: Mechanisms and Therapeutic Opportunities." Int J Mol Sci. Jul. 2, 2022;23(13):7376. (Year: 2022).*
Kasner et al. "Sirolimus Enhances Remission Induction in Patients with High Risk Acute Myeloid Leukemia and mTORC1 Target Inhibition." Invest New Drugs. Apr. 2, 2018;36(4):657-666. (Year: 2018).*

(Continued)

*Primary Examiner* — Titilayo Moloye
(74) *Attorney, Agent, or Firm* — Nevrivy Patent Law Group P.L.L.C.

(57) ABSTRACT

Provided herein are compositions and methods for down-regulating mTORC1 signaling in a subject, comprising administering to the subject an effective amount of one or more compositions that promote increased levels or activity of CIB2 or a biologically active fragment or variant thereof in the subject.

20 Claims, 33 Drawing Sheets

Specification includes a Sequence Listing.

(56)  References Cited

OTHER PUBLICATIONS

International Search Report from Appl. No. PCT/US19/44745, mailed on Jan. 13, 2020.

Zhu et al., CIB2 Negatively Regulates Oncogenic Signaling in Ovarian Cancer via Sphingosine Kinase 1, Cancer Res, (2017), 77(18): 4823-4834.

Jin et al., Preclinical study of CC223 as a potential anti-ovarian cancer agent. Oncotarget, (2017), 8:58469-58479.

Rodriguez et al., Sphingosine-1 Phosphate: A New Modulator of Immune Plasticity in the Tumor Microenvironment, Front. Oncol, (2016), 6:218.

Young et al., Shingosine Kinase 1 cooperates with Autophagy to Maintain Endocytic Membrane Trafficking, Cell Rep. (2016), 17:1532-1545.

Bouquerel et al., Essential role for SphK1/S1P signaling to regulate hypoxia-inducible factor 2α expression and activity in cancer. Oncogenesis, (2016), 5:e209, p. 1-12.

Supplemantary European Search Report from Appl. No. EP19845195, mailed on Apr. 13, 2022.

Zhu et al., CIB2 Negatively Regulates Oncogenic Signaling in Ovarian Cancer via Sphingosine Kinase 1, Cancer Research, (2017), 77:4823-4834.

Giese et al., CIB2 interacts with TMC1 and TMC2 and is essential for mechanotransduction 1n auditory hair cells, Nature Communications, (2017), 8: 1-13.

Ballou et al., Rapamycin and mTOR kinase inhibitors, Journal of Chemical biology, (2008), 1: 27-36.

* cited by examiner

Fig. 1

2 month 8 month

Fig. 12

MODULATION OF mTORC1 ACTIVITY AND AUTOPHAGY VIA CIB2-RHEB INTERACTION

CROSS REFERENCE TO RELATED APPLICATIONS

This application claims the benefit of U.S. Provisional Application No. 62/713,044, filed Aug. 1, 2018, the contents of which are incorporated by reference herein in their entirety.

STATEMENT OF FEDERALLY SPONSORED RESEARCH AND DEVELOPMENT

This invention was made with government support under Grant Numbers DC012564, DC016295, and DC011803 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable amino acid and nucleotide sequence listing submitted concurrently herewith and identified as follows: One 20,099 Byte ASCII (Text) file named "SEQ_Listing.TXT," created on Aug. 1, 2019.

FIELD OF THE INVENTION

The field of the invention relates to pharmaceuticals and medicine, particularly compositions and methods to treat disease such as age-related macular degeneration, cancer, neurodegeneration, and other diseases/disorders wherein mTORC1 is hyperactive.

BACKGROUND OF THE INVENTION

Age-related macular degeneration (AMD) affects 10% of the population over 65 years and rising to more than 25% of population older than 75 years. By 2050, the prevalence is expected to increase by further 50% (Brown et al., Transactions of the American Ophthalmological Society 103, 173-186 (2005); Wong et al., The Lancet Global Health 2, e106-e116 (2014)). AMD can be clinically stratified in to 'wet' and 'dry' forms. Wet AMD, which arises from the dry form, affects about 10% of the patients and involves choroidal neovascularization invading the avascular sub-retinal region. Wet AMD may rapidly lead to complete blindness if left untreated, however, excellent treatment options are available (Al-Zamil, W. M., and Yassin, S. A. *Clinical Interventions in Aging* 12, 1313-1330 (2017)). In contrast, dry AMD is a protracted disease with variable symptoms and progression (Ambati, J., and Fowler, Benjamin J. *Neuron* 75, 26-39 (2012)) . . . . The dry form of AMD has no treatment options even though several causal genes and lifestyle factors such as smoking have been identified (Cheng et al., 2015; Edwards et al., 2005; Fritsche et al., 2014; Fritsche et al., 2016; Hageman et al., 2005; Haines et al., 2005; Huang et al., 2015; Klein et al., 2005; Swaroop et al., 2009; The, 2013). Dry AMD's primary etiological site is the retinal pigment epithelium (RPE)/choroid and secondarily affects the function and integrity of photoreceptors (PR).

The RPE is a single layer of polarized cuboidal epithelium. The RPE apical microvilli are in close contact to the rod PR outer segments (OS). On the basolateral side, along with the Bruch's membrane, RPE forms the blood-subretinal space barrier. Further, the RPE secrets inhibitory factors from the apical side to maintain sub-retinal space avascularity, while simultaneously secreting pro-vascular growth factors such as VEGF from basolateral side to promote choroidal vasculature growth. RPE absorbs excess light, is essential for visual cycle regeneration of vitamin A derivatives, shuttles nutrients to the PR and metabolites out of the sub-retinal space amongst others. One of the notable functions of RPE is the LC3-associated phagocytosis (LAP) of OS for maintaining the length and thus health of the PR (Strauss, (2005). Physiological Reviews 85, 845-881).

Macroautophagy (henceforth autophagy) is a catabolic process which removes cellular debris and damaged/aged organelles and shares many features with LAP. Autophagy is an essential process for all cells, but particularly post-mitotic cells such as PRs (Zhou et al., (2015a). Cell Death And Differentiation 22, 488; Zhou et al., (2015b). Autophagy 11, 1821-1832) and RPE (Kim et al., (2013). Cell 154, 365-376). which have the highest life-long phagocytic load of any cell-type in body. LAP of OS requires canonical autophagy proteins Atg5 and LC3 but pre-initiation complex proteins ULK1/Fip2000/Atg13 are dispensable (Kim et al., (2013). Cell, 154, 365-376). Defects in phagocytosis/autophagy have been implicated in dry AMD (Golestanch et al., (2017). Cell Death &Amp; Disease 8, e2537). In dry AMD there is accumulation of drusen between the RPE and Bruch's membrane, vacuolization of the RPE, lipid deposits within the RPE and or RPE/Bruch's membrane amongst others (Fritsche et al., (2014). Annual Review of Genomics and Human Genetics 15, 151-171; Kaarniranta et al., (2013), Autophagy 9, 973-984). In cultured RPE cells, age-lipid such as lipofuscin have been shown to interfere with degradative process within phagolysosomes and autolysosomes and further cause a feedback-loop-mediated accumulation of undigested lipids (Vives-Bauza et al., (2008). The Journal of Biological Chemistry 283, 24770-24780).

Mechanistic target of rapamycin (mTOR) forms 2 large multi-subunit complexes, mTORC1 and mTORC2. mTORC1 is the key balancer of catabolismand anabolism and is a negative regulator of autophagy under nutrient rich conditions via phosphorylating key initiation kinase, ULK1. mTORC1 is cytosolic and in presence of sufficient nutrients, specifically amino acids, is recruited to the surface of the lysosomes by the Rag-Ragulator complex (Saxton et al., (2017), Cell 168, 960-976; Wolfson et al. (2017). Cell Metabolism 26, 301-309). Growth factors and cell stressors converge on the Tuberous Sclerosis Complex (TSC) complex, upstream of mTORC1 (Demetriades et al., (2016). Nature Communications 7, 10662). TSC complex which consists of TSC1, TSC2, and TBC1D7 directly regulates the small GTPase, Rheb, via spatial control and TSC2's Rheb-GAP activity (Menon et al., (2014). Cell 156, 771-785). Rheb, in its GTP bound state, allosterically realigns the kinase active site of mTORC1 and thus is a potent and obligate activator of mTORC1 on the surface of the lysosomes (Yang et al., (2017). Nature 552, 368).

There is a significant need to develop new therapeutics and methods to treat diseases or conditions associated with mTORC1 signaling and aberrant autophagy.

This background information is provided for informational purposes only. No admission is necessarily intended, nor should it be construed, that any of the preceding information constitutes prior art against the present invention.

3

SUMMARY

It is to be understood that both the foregoing general description of the embodiments and the following detailed description are exemplary, and thus do not restrict the scope of the embodiments.

It is shown herein that calcium and integrin binding protein 2 (CIB2) is a negative regulator of mTORC1 but not mTORC2 signaling. Using a combination of ubiquitous and tissue-specific knockout mouse models, functional and biochemical assays, it was discovered that lack of CIB2, specifically in the RPE, leads to LAP/autophagy defects. Further, RPE lacking CIB2 have aberrant mTORC1 activity leading to autophagy flux defects, and AMD-like phenotype in mice. Concordant molecular deficits were observed in RPE/choroid tissues from humans affected with dry AMD. Mechanistically, it is shown herein that CIB2 regulates mTORC1 activity via preferential binding to GDP-bound state of Rheb, essentially acting as guanine dissociation inhibitor (GDI) of Rheb. Upregulation of mTORC1 signaling and aberrant autophagy is also implicated in ageing, cancers, obesity, TSC, epilepsy, autism, and Alzheimer's amongst others (Laplante and Sabatini, 2012). Further, overexpression of CIB2 in patient-derived lymphangioleiomyomatosis cells down-regulated hyperactive mTORC1 signaling. Thus, CIB2 represent a new molecular target for modulation of mTORC1 signaling in ageing organs and autophagy disorders.

In one aspect, the invention provides a method for down-regulating mTORC1 signaling in a subject, comprising administering to the subject an effective amount of one or more compositions that increase activity of CIB2 or a biologically active fragment or variant thereof in the subject.

In another aspect, the invention provides a method for down-regulating mTORC1 signaling in a cell, comprising administering to the cell an effective amount of one or more compositions that increase activity of CIB2 or a biologically active fragment or variant thereof in the cell.

In another aspect, the invention provides a method for treating a disease, condition, or disorder which would benefit from down-regulation of mTORC1 signaling in a subject, comprising administering to the subject an effective amount of one or more compositions that increase activity of CIB2 or a biologically active fragment or variant thereof, thereby treating the disease, condition, or disorder in the subject.

In another aspect, the invention provides a method for down-regulating mTORC1 signaling in a subject, comprising administering to the subject an effective amount of one or more compositions that promote increased levels of CIB2 or a biologically active fragment or variant thereof in the subject.

In another aspect, the invention provides a method for down-regulating mTORC1 signaling in a cell, comprising administering to the cell an effective amount of one or more compositions that promote increased levels of CIB2 or a biologically active fragment or variant thereof in the cell.

In another aspect, the invention provides a method for treating a disease, condition, or disorder which would benefit from down-regulation of mTORC1 signaling in a subject, comprising administering to the subject an effective amount of one or more compositions that promote increased levels of CIB2 or a biologically active fragment or variant thereof, thereby treating the disease, condition, or disorder in the subject.

In another aspect, the invention provides a method for increasing autophagy and/or phagolysosomal digestion in cells, comprising administering to the cells an effective amount of one or more compositions that increase activity of CIB2 or a biologically active fragment or variant thereof in the cells.

In another aspect, the invention provides a method for increasing autophagy and/or phagolysosomal digestion in cells, comprising administering to the cells an effective amount of one or more compositions that promote increased levels of CIB2 or a biologically active fragment or variant thereof in the cells.

In another aspect, the invention provides a method for increasing autophagy and/or phagolysosomal digestion in a subject, comprising administering to the subject an effective amount of one or more compositions that increase activity of CIB2 or a biologically active fragment or variant thereof in the subject.

In another aspect, the invention provides a method for increasing autophagy and/or phagolysosomal digestion in a subject, comprising administering to the subject an effective amount of one or more compositions that promote increased levels of CIB2 or a biologically active fragment or variant thereof in the subject.

In some embodiments, the disease, condition, or disorder is selected from ageing, cancer, obesity, epilepsy, autism, Alzheimer's, Tuberous Sclerosis Complex, lymphangioleiomyomatosis (LAM), Stargardt disease, and age-related macular degeneration (e.g., dry and/or wet).

In another aspect, the invention provides a viral vector comprising a nucleotide sequence encoding CIB2 or a biologically active fragment or variant thereof.

In another aspect, the invention provides an isolated nucleic acid molecule encoding CIB2 or a biologically active fragment or variant thereof.

In another aspect, the invention provides a nucleic acid encoding a fusion protein comprising
i) a nucleotide sequence encoding CIB2 or a biologically active fragment or variant thereof; and
ii) a nucleotide sequence encoding a protein transduction domain.

In another aspect, the invention provides an isolated polypeptide comprising CIB2 or a biologically active fragment or variant thereof.

In another aspect, the invention provides a fusion protein comprising
i) CIB2 or a biologically active fragment or variant thereof; and
ii) a protein transduction domain.

In another aspect, the invention provides a pharmaceutical composition comprising a polypeptide comprising CIB2 or a biologically active fragment or variant thereof and an agent that facilitates uptake of the polypeptide into cells.

In another aspect, the invention provides a pharmaceutical composition comprising a viral vector encoding CIB2 or a biologically active fragment or variant thereof and one or more pharmaceutically acceptable excipients.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

7 but reproducibly improved ERG amplitudes. f. TEM micrographs for indicated genotype at the end of the treatment paradigm as outlined in c (n=3/genotype). Scale bar. 2 μm. Unpaired two-tailed i test, p value of at least <0.05 (*).

Figure 5:
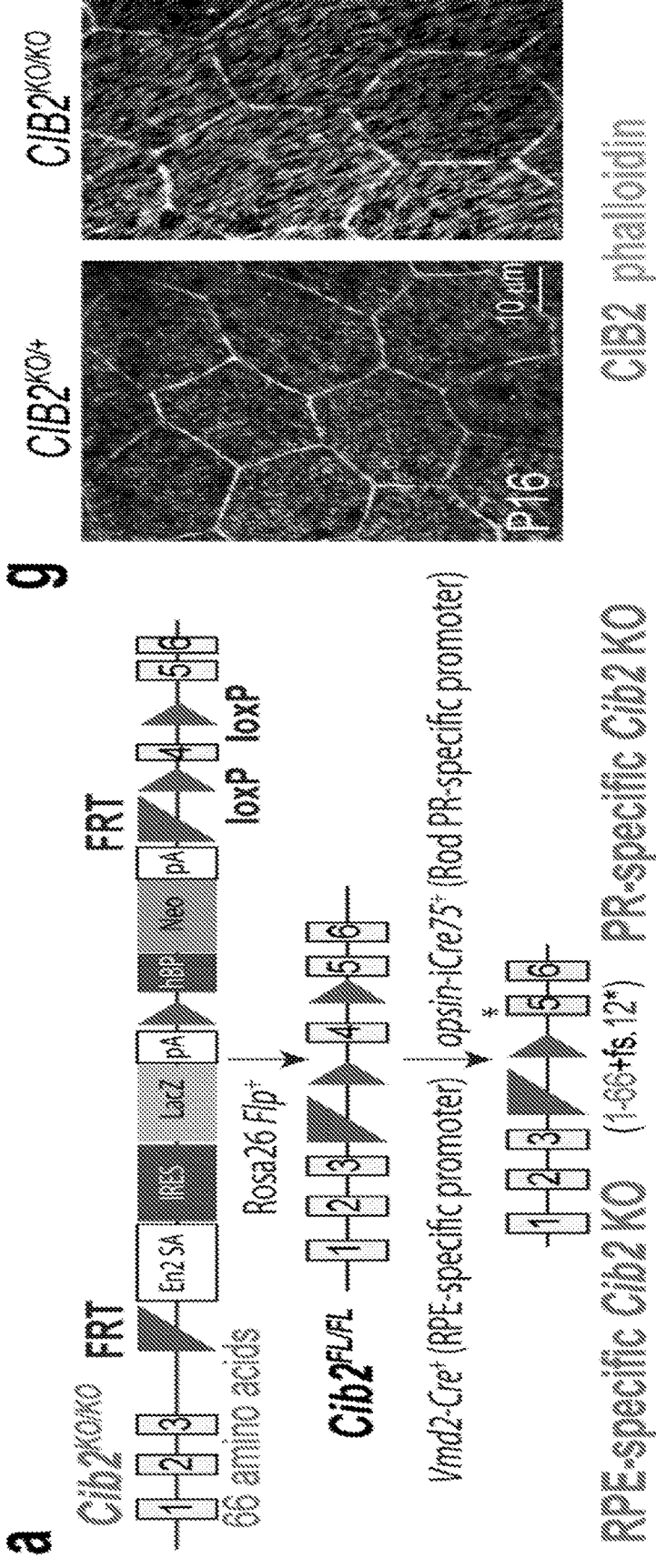
Figure 5:
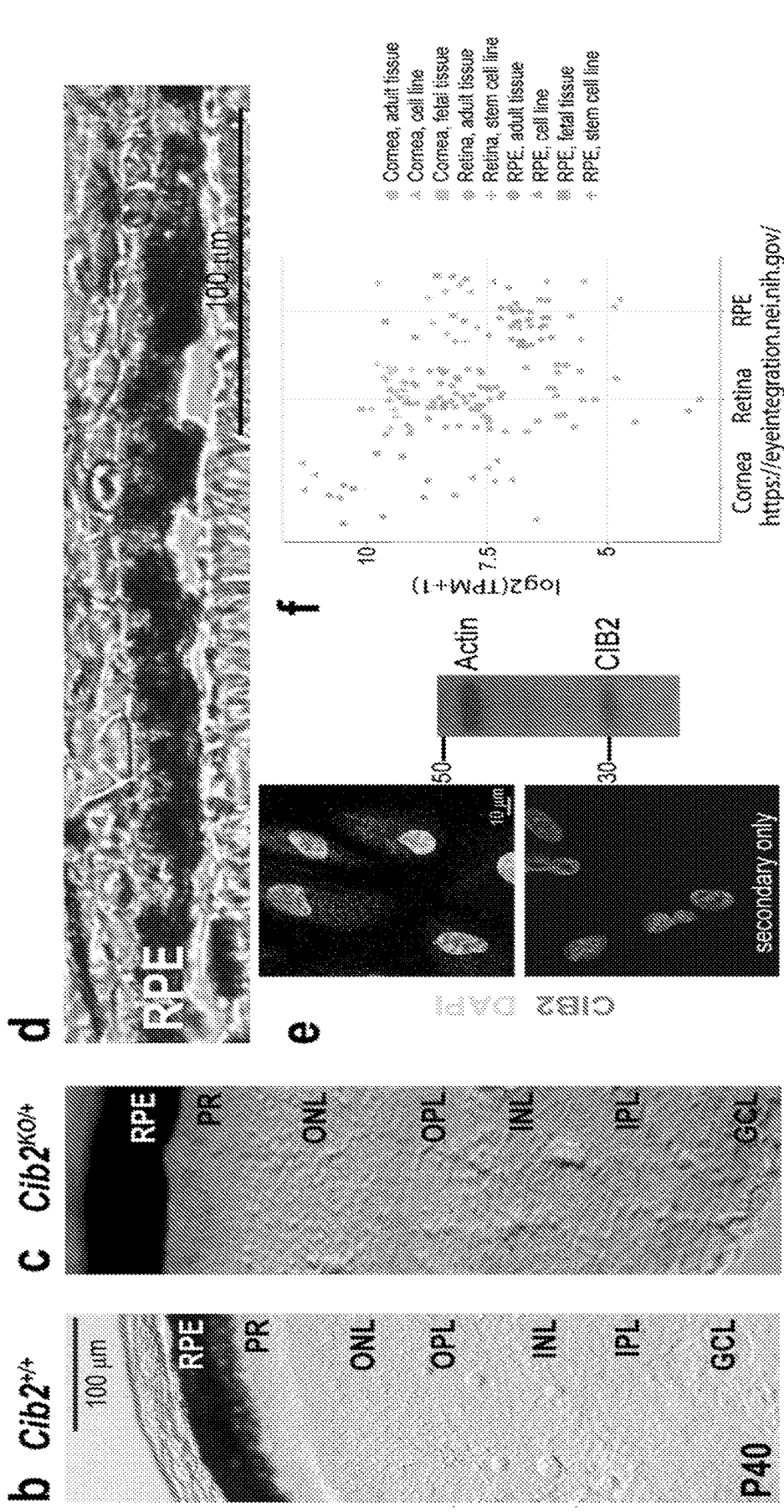

FIG. 5. Structure of Cib2 mutant alleles and expression of CIB2 in the retina. a. Schematic of specific constructs used to create mouse models used in these studies. b, c. X-gal staining (blue) of retina from P40 Cib2$^{+/+}$ (b) or Cib2$^{KO/+}$ (c) mouse shows Cib2 promoter activity in IS, OPL, INL, GCL, and RPE. d, Magnified image of retinal pigment epithelium (RPE) from Cib2$^{KO/+}$ mouse stained with X-gal (blue) shows Cib2 promoter activity. e, CIB2 (magenta) immunostaining (cyan-DAPI; left panel) and immunoblotting (right panel) for indicated proteins from rat RPE-J cell line. f. Scatter plot of CIB2 expression in indicated retinal/RPE tissues and cell lines collated by the NEI (https://eyeintegration.nei.nih.gov). g, CIB2 immunostaining (magenta) and actin stained with phalloidin (grey) in P16 RPE whole mounts from Cib2$^{KO/+}$ (left panel) Cib2$^{KO/KO}$ (right panel) shows specific absence of CIB2 staining in mutant mice. PR-photoreceptors; ONL-outer nuclear layer; OPL-outer plexiform layer; INL-inner plexiform layer; GCL-ganglion cell layer.

Figure 1:
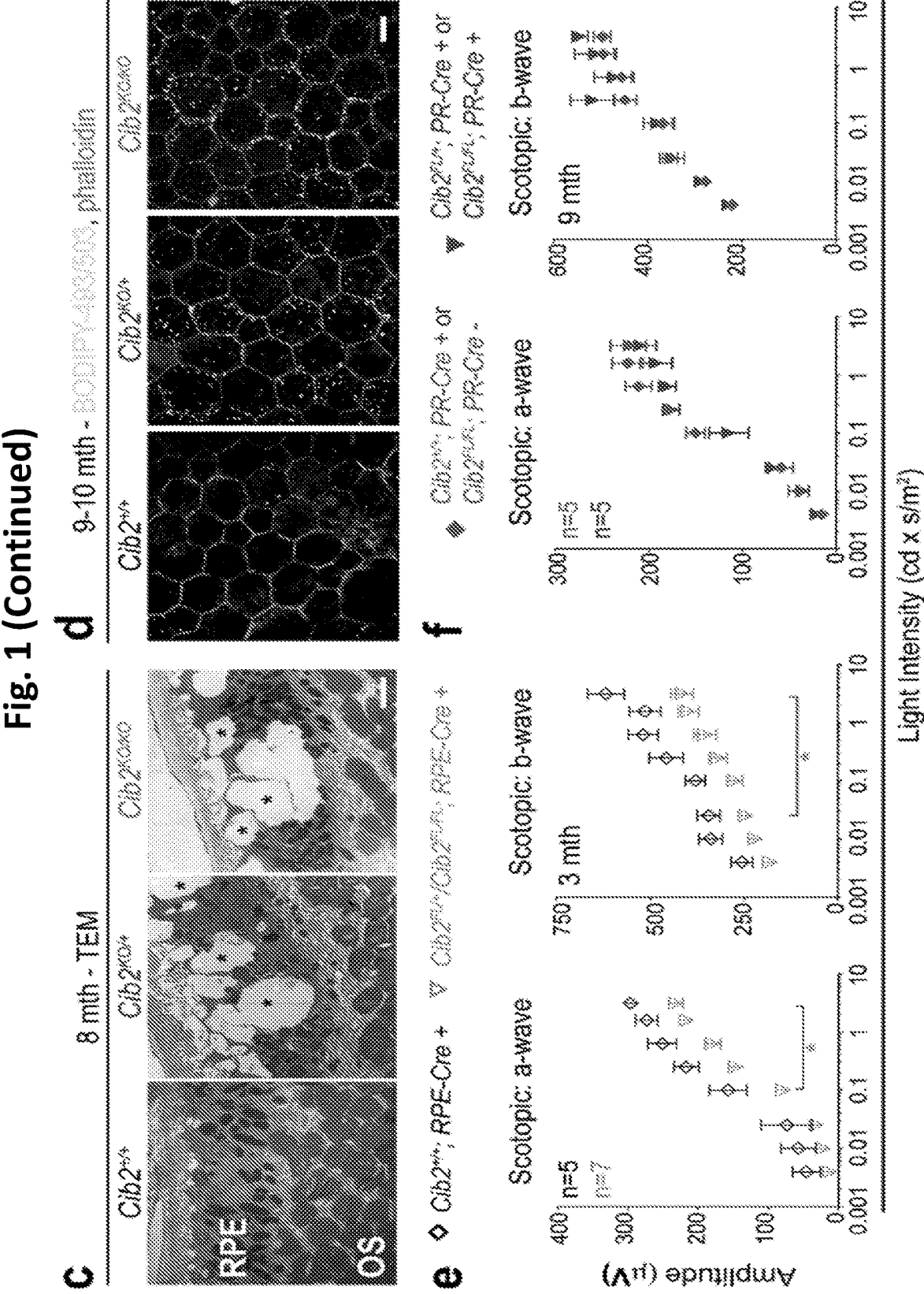
FIG. 1. Removal of CIB2, specifically from the RPE, leads to age-related PR dysfunction and RPE pathophysiology. a, Schematic representation of the different retinal layers. ERG a-wave originates from photoreceptors (PR), while b-wave amplitude originates from Müller glia and outer nuclear bipolar cells, and oscillatory potential of the amacrine cells. RPE—retinal pigment epithelium. b, Quantification of scotopic responses from WT (Cib2$^{+/+}$), Cib2$^{KO/+}$, and Cib2$^{KO/KO}$ at ages of 1 month and 3 months revealed progressive loss of both a- (left panels) and b-wave (right panels) amplitudes in Cib2 deficient mice. c, TEM micrographs of RPE/OS interface from 8 months old mice revealed vacuoles (*) and basal infoldings loss specifically in Cib2$^{KO/+}$ and Cib2$^{KO/KO}$ mutants. Scale bar, 2 μm. OS— outer segment. d. Representative photomicrographs of RPE whole mounts from 9-10 months old mice for denoted genotype showing accumulation of neutral lipid marker BODIPY-493/503 (cyan) in Cib2 deficient mice. Phalloidin (magenta) was used to decorate actin cytoskeleton. Scale bar. 10 μm. e, f, Quantification of scotopic a- (left panels) and b-wave (right panels) amplitudes for RPE-Cre+ (e, 3 months old) and PR-Cre mice (f, 9 months old). Loss of CIB2 specifically from RPE but not from PR resulted in ERG deficits. Data presented as mean±SEM. Each data point represents an individual mouse. One-way ANOVA and Bonferroni post hoc test (b) or unpaired two-tailed/test (c, f), p value of <0.05 (*). g, TEM micrographs of 8 months old RPE-Cre+ control Cib2$^{+/+}$ (right panel) and Cib2$^{FL/FL}$ (left panel) mice (n=3 per genotype). Red arrows (bottom panel) indicate boundaries of sub-RPE deposits in the mutant mice. CC—choriocapillary. Scale bar, 2 μm.
Figure 1:
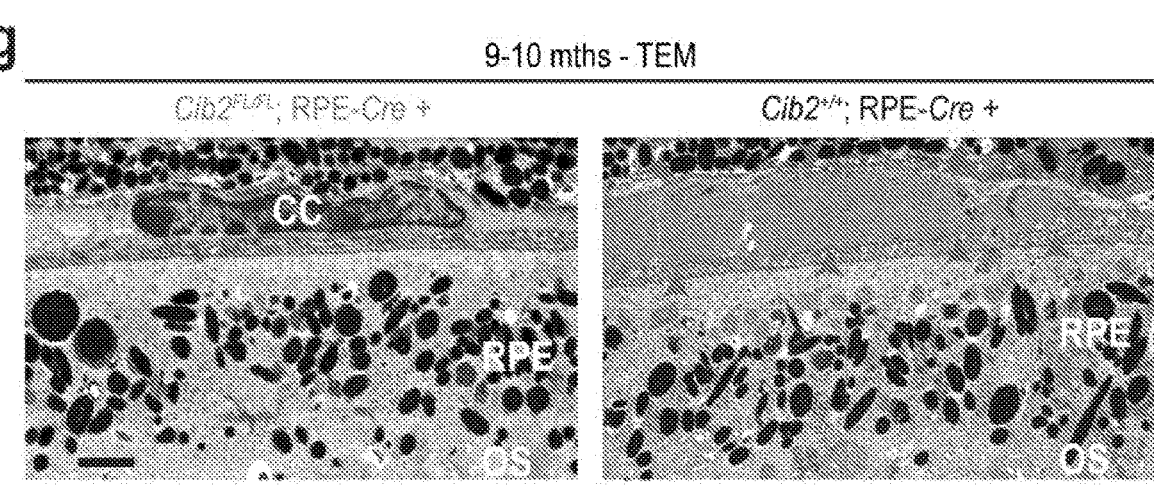
Figure 6:
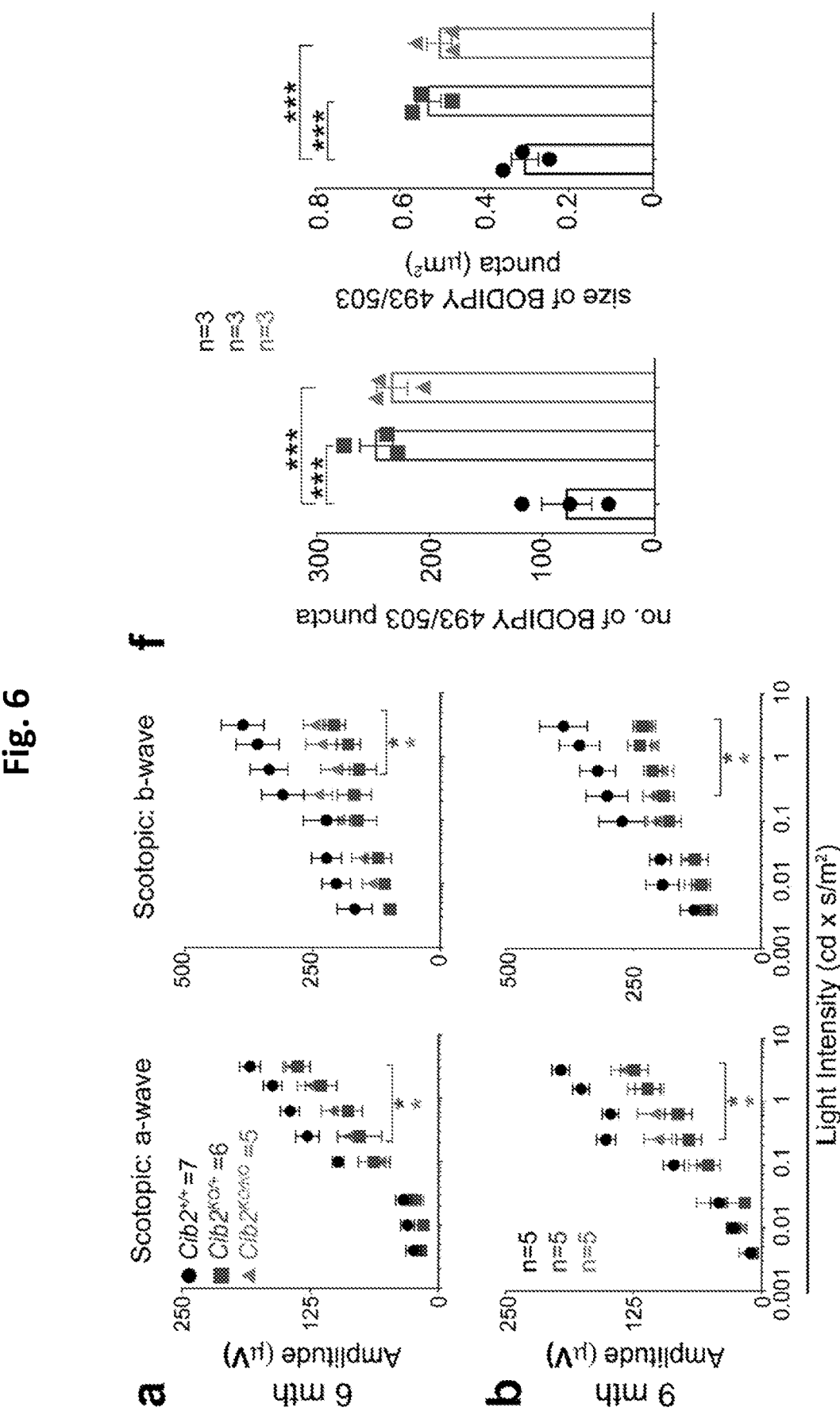
Figure 6:
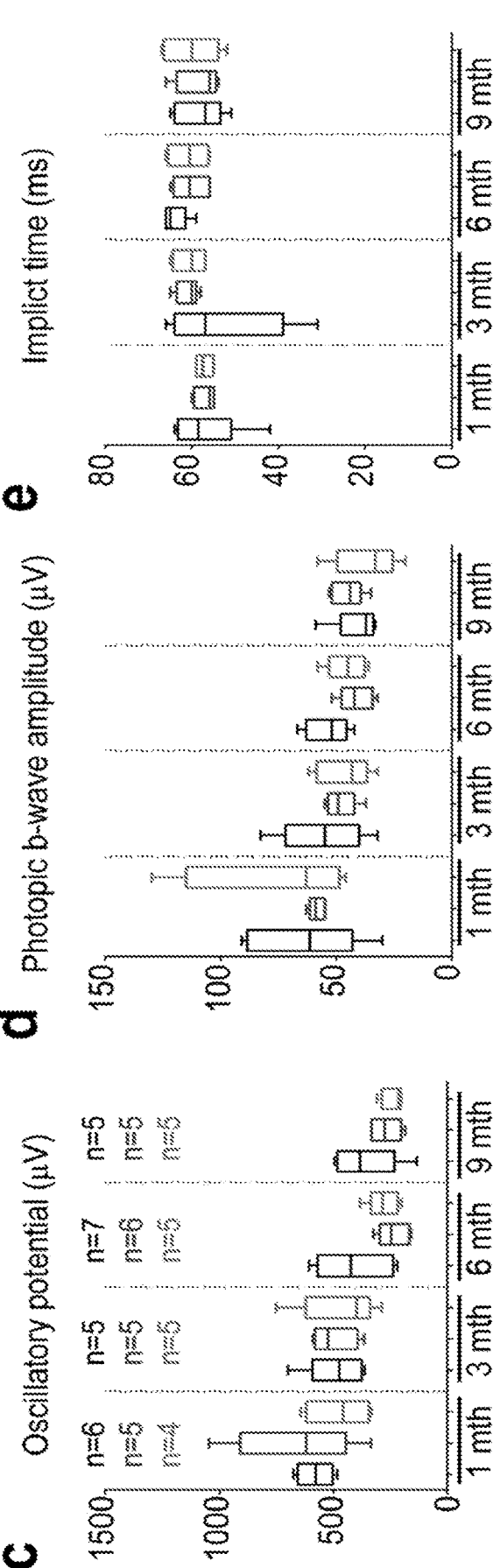

FIG. 6. Loss of CIB2 leads to age related PR dysfunction and neutral lipid accumulation. a, b, Quantification of scotopic a- (left panels) and b-wave (right panels) amplitudes from WT, Cib2$^{KO/+}$, and Cib2$^{KO/KO}$ mice at ages of (a) 6 months, and (b) 9 months shows progressive decline in ERG amplitude in the mutant mice (related to FIG. 1$b$). c-e, Box and whisker plots for oscillatory potential (c), photopic b-wave (d), and implicit time for scotopic b-wave (e) for indicated genotype and time point revealed no statistically significant differences between the control and mutant mice. f, Quantification of average number (left) or average size (right) of BODIPY-493/503-stained puncta per mouse shown in FIG. 1$d$. At least 3 images per mouse (~25 cells/image) were quantified and averaged for each genotype (n=3 mice/genotype). Data presented as mean±SEM; each point represents an individual mouse. One-way ANOVA and Bonferroni post hoc test, p value of <0.05 (*). <0.01 (), and <0.001 (*).

Figure 7:
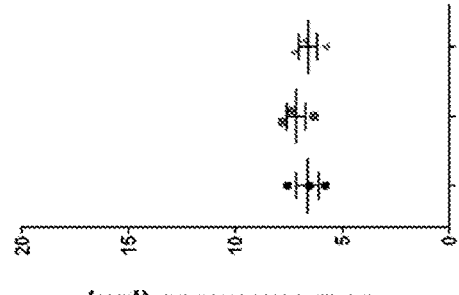
Figure 7:
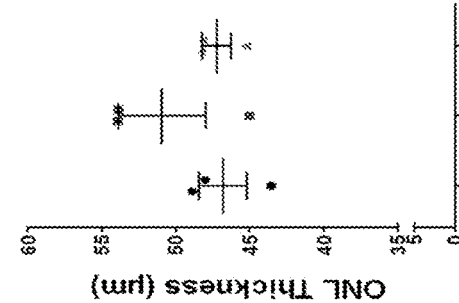
Figure 7:
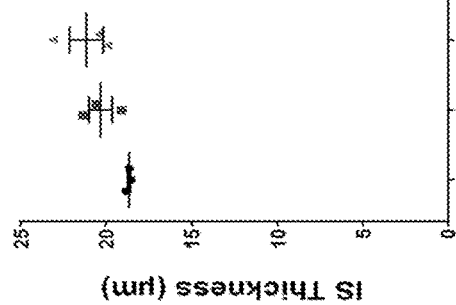
Figure 7:
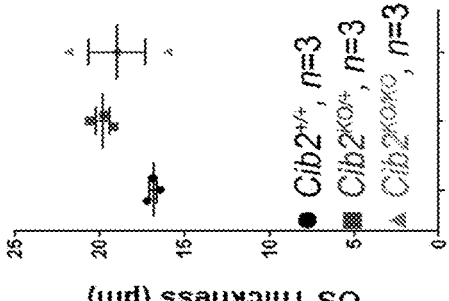
Figure 7:
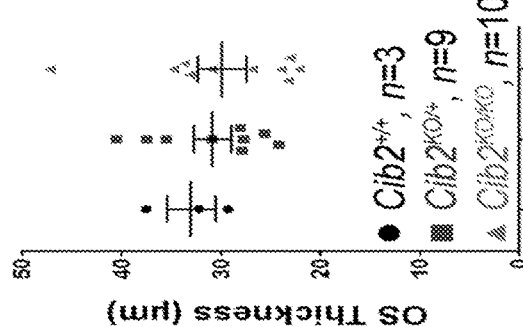

FIG. 7. Retinal morphometry shows no differences in gross morphology of Cib2$^{KO}$ mice. a, b, Morphometric analysis of retinal layer thickness in control and mutant mice aged 2 months (a) or 8 months (b) showed no obvious retinal degeneration, see Methods for quantification and orientation parameters. OS-outer segments; IS-inner segments; ONL-outer nuclear layer; OPL-outer plexiform layer; INL-inner plexiform layer.

Figure 8:
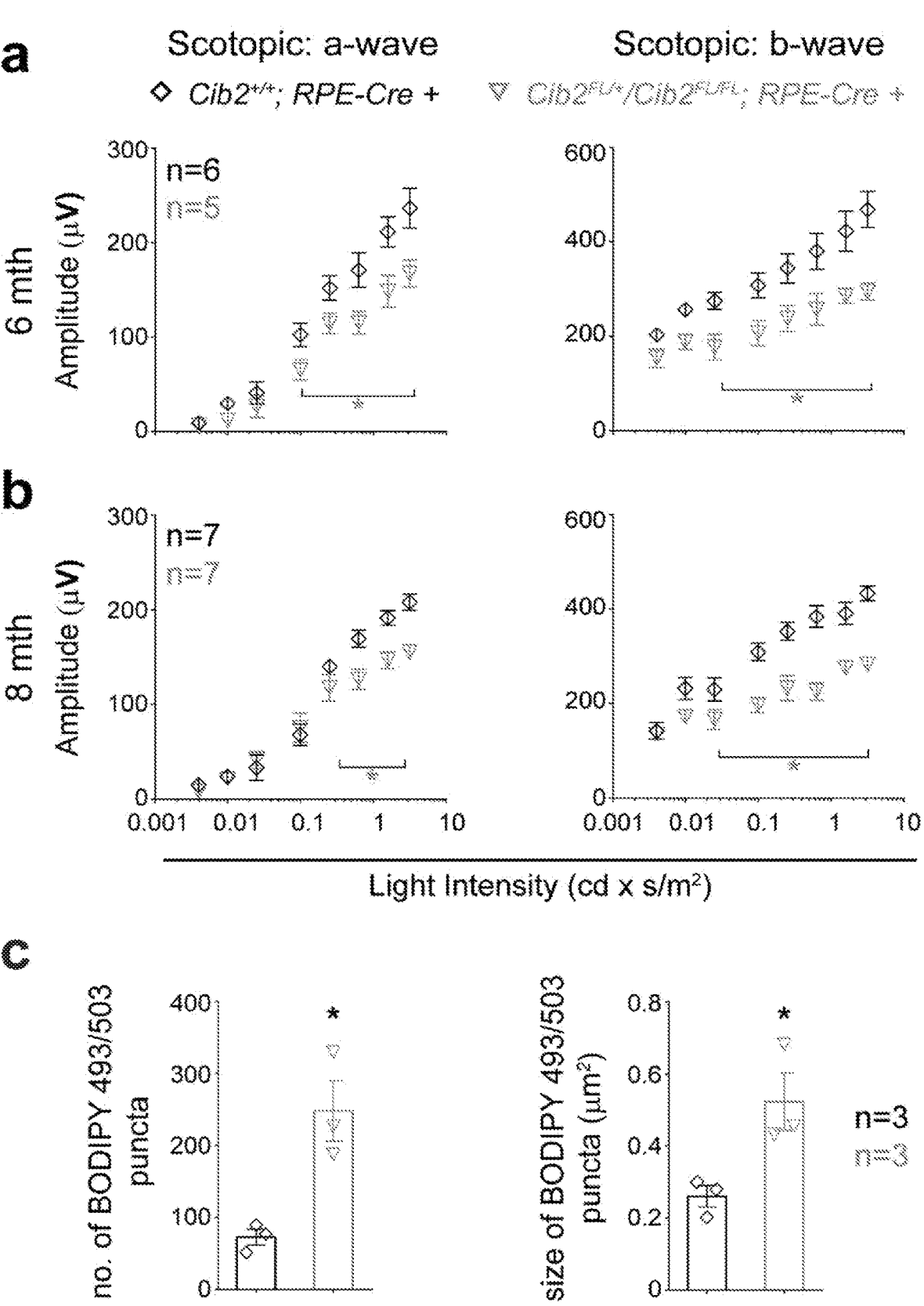

FIG. 8. RPE-specific loss of CIB2 recapitulates age related RPE phenotype. a, b, Quantification of scotopic (rod) a- (left panels) and b-wave (right panels) amplitudes from RPE-Cre+ mice at ages (a) 6 months (c) 8 months shows progressive ERG amplitude loss for RPE-specific Cib2 mutants. c, Quantification of average number (left) or size (right) of BODIPY-493/503 puncta per mouse. At least 3 images per mouse (~25 cells/image) were quantified and averaged for given genotypes (n=3/genotype). Data presented as mean±SEM. Each data point represents an individual mouse. Student unpaired t-test, p value <0.05 (*).

Figure 9:
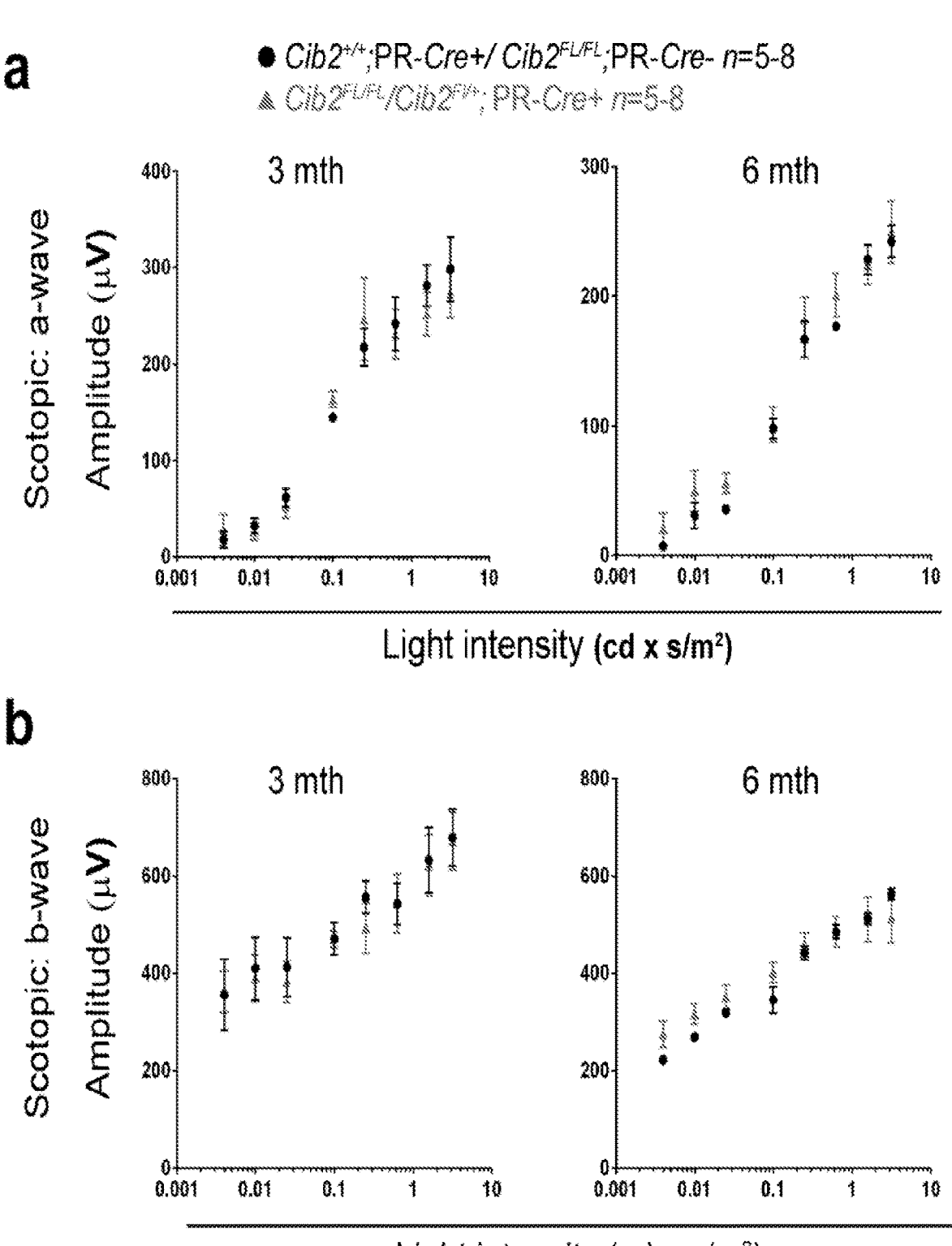
Figure 9:
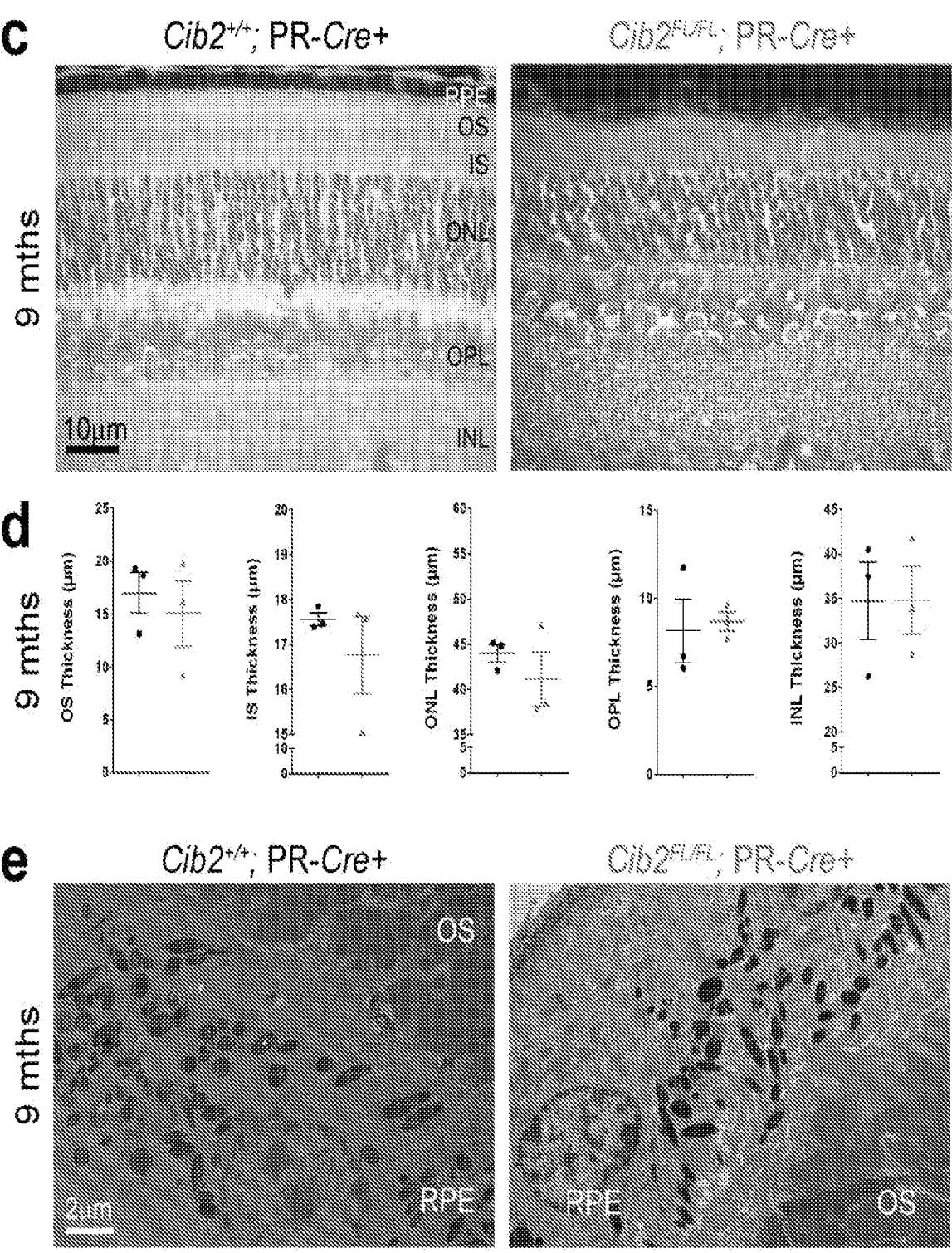

FIG. 9. ERG, light microscopic, and TEM analyses of rod PR-specific Cib2$^{KO}$ mice. a, b, Quantification of scotopic a- (left panels) and b-wave (right panels) amplitudes for indicated genotypes and ages showed no differences in ERG amplitudes. c. Light micrographs of indicated genotypes at 9 months of age. d. Morphometry of retinal layers' thicknesses for indicated genotypes at 9 months of age revealed no obvious damage. e, TEM micrographs of the interface of the RPE and OS at 9 months of age showed no obvious RPE defects (n=3). RPE-retinal pigment epithelium; PR-photoreceptors; ONL-outer nuclear layer; OPL-outer plexiform layer; INL-inner plexiform layer; GCL-ganglion cell layer.

Figure 2:
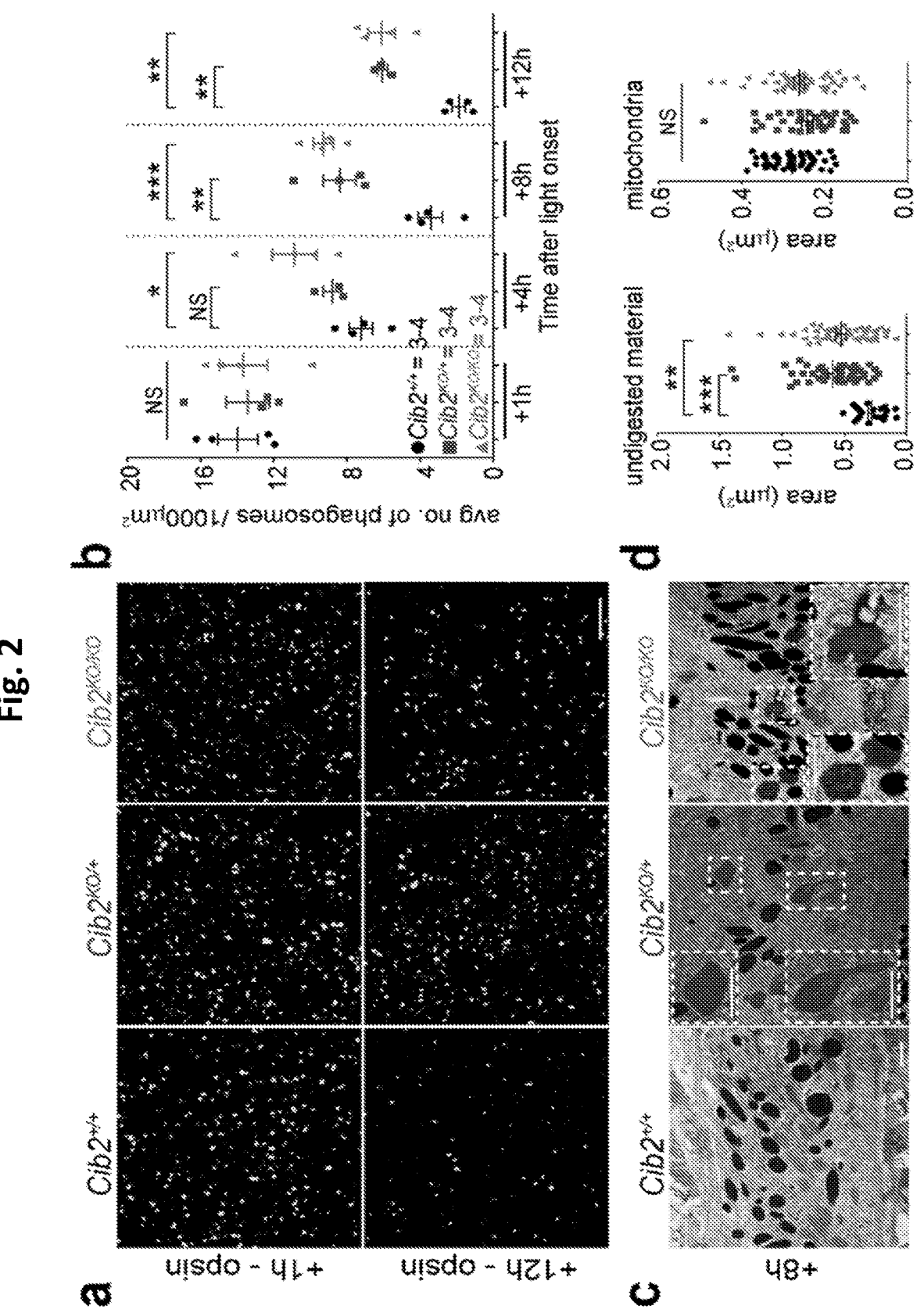
FIG. 2. Deficiency of CIB2 leads to impaired phagolysosomal processing of OS, increased mTORC1 signaling and reduced autophagy. a. RPE whole mounts from 3-4 months old mice immunostained with opsin Ret-P1 antibody (cyan) shows initial binding and ingestion of opsin-phagosomes is similar across genotypes (top panel), however, the phagolysosomal digestion is slower in mutant mice (bottom panel) as compared to WT control. Scale bar, 10 μm. b. Quantification of opsin-phagosomes shown in panel a and FIG. 11a. At least 3 images per mouse (~30 cells/image) were quantified and averaged. c. TEM micrographs of 2 months old mice euthanized 8 hr after light onset show accumulation of undigested material, and fused remnants of phago-melanosomes (Inset) only in Cib2$^{KO/+}$ and Cib2$^{KO/KO}$. Scale bar. 1 μm. d. Quantification of individual phagosomal (left) and mitochondrial (right) areas (as control) for images shown in panel c further confirms marked accumulation of phagosomal area. All phagosomes and 15 mitochondria/image in 3-5 images per mouse were counted. e. RPE whole mounts from 3-4 months old mice stained with BODIPY-pepstatin A demonstrate fewer indirectly stained lysosomes, quantified in panel f, in Cib2 deficient mice. Full panels with phalloidin staining are shown in FIG. 10a. At least 3 images per mouse (~30 cells/image) were quantified and averaged. Scale bar. 10 μm. g, Representative RPE whole mounts images from 3-4 months old mice immunostained with opsin Ret-P1 antibody (cyan) show slower phagolysosomal clearance, quantified in panel h, in RPE-specific Cib2 mutant mice. At least 3 images per mouse (~30 cells/image) were quantified and averaged number of phagosomes (left) or average size of phagosomes (right) per animal were plotted. Scale bar, 10 μm. i, j. Higher number of indirectly stained lysosomes were found in RPE-Cre+ but not PR-Cre mouse RPE. Quantification of average numbers (left) or sizes (right) of BODIPY-pepstatin A puncta per RPE-Cre+ (i) and PR-Cre (j) mouse are shown in FIG. 10b. k, l, Induced autophagy in vivo by food starving for 24 hrs shows reduced autophagy from RPE/choroid lysates, as levels of both, LC3-II and P62 are higher, quantified in panel 1, in Cib2 mutant mice. m, n, Higher levels, quantified in panel n, of phospho-protein levels of 4-EB-P1 and S6K1, but not mTORC2 target AKT2, indicate hyperactive mTORC1 in RPE/choroid lysates after in vivo induced autophagy. At least 3 images per mouse per genotype (~30 cells/image) were quantified and averaged. Data presented as mean±SEM. One-way ANOVA and Bonferroni post hoc test (b, d, f, l, n) or unpaired two-tailed t test (h-j), p value of <0.05 (*), <0.01 (), or <0.001 (*). NS—not significant.
Figure 2:
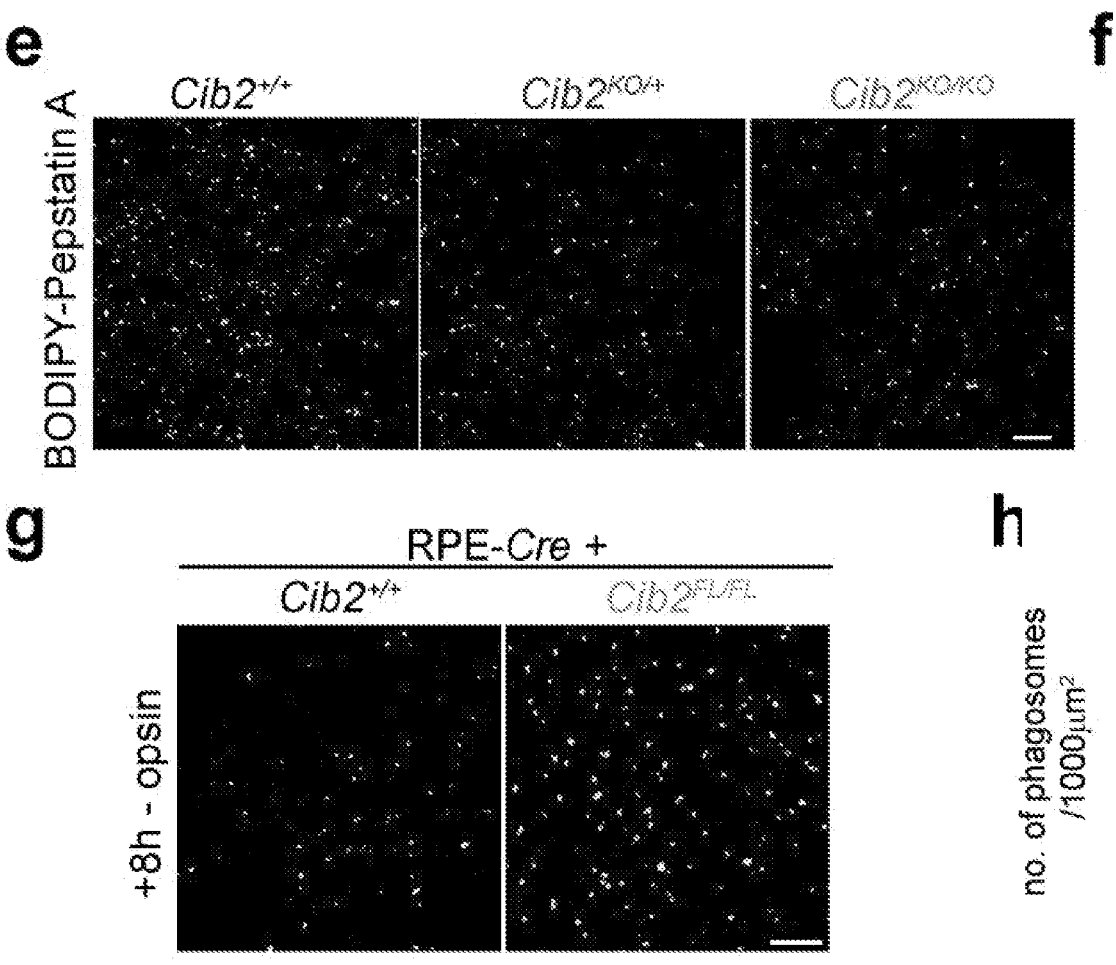
Figure 2:
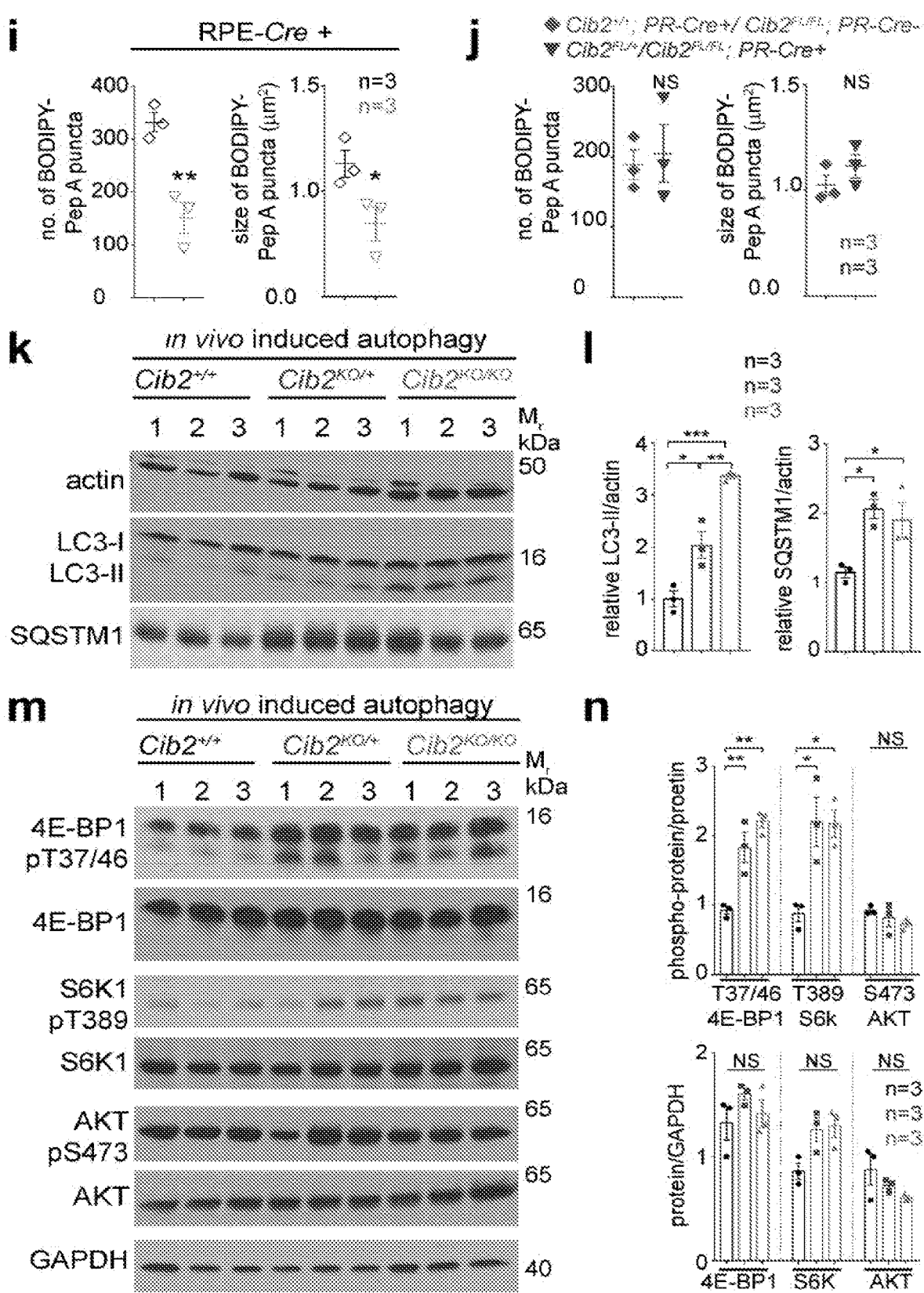
Figure 10:
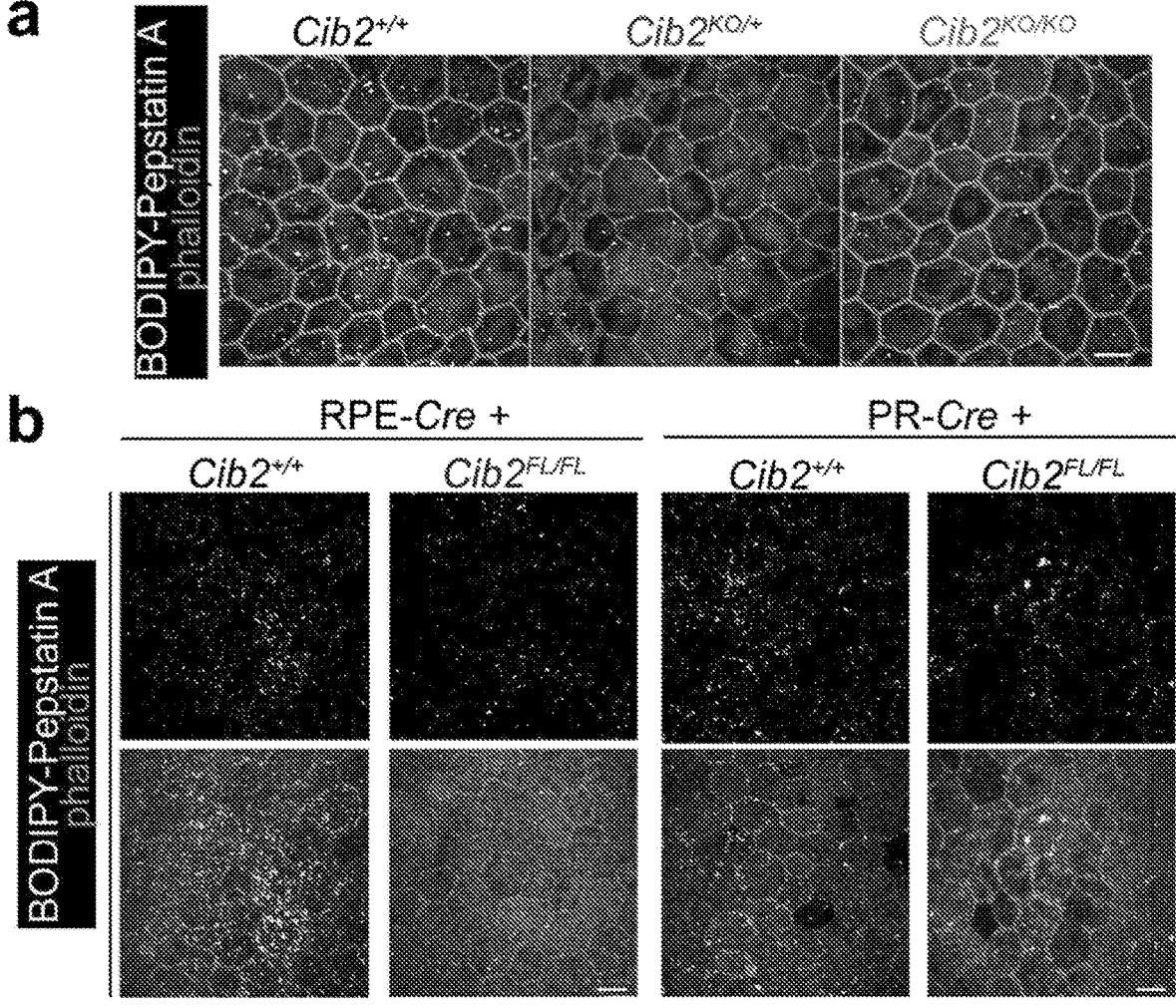

FIG. 10. BODIPY-pepstatin staining reveals fewer indirectly stained lysosomes in RPE of whole-body and RPE-specific Cib2$^{KO}$ but not PR-specific mutant mice. a. RPE whole mounts from 3-4 months old mice show that RPE-specific Cib2 mutants have less BODIPY-pepstatin A stained lysosomes, (related to FIG. 2$e$, $f$). Scale bar, 10 μm. b. BODIPY-Pepstatin A (yellow puncta) and phalloidin (magenta) in RPE flat mounts from indicated genotypes at 2-3 month of age (related to FIG. 2$i$, $j$). Scale bar, 10 μm.

Figure 11:
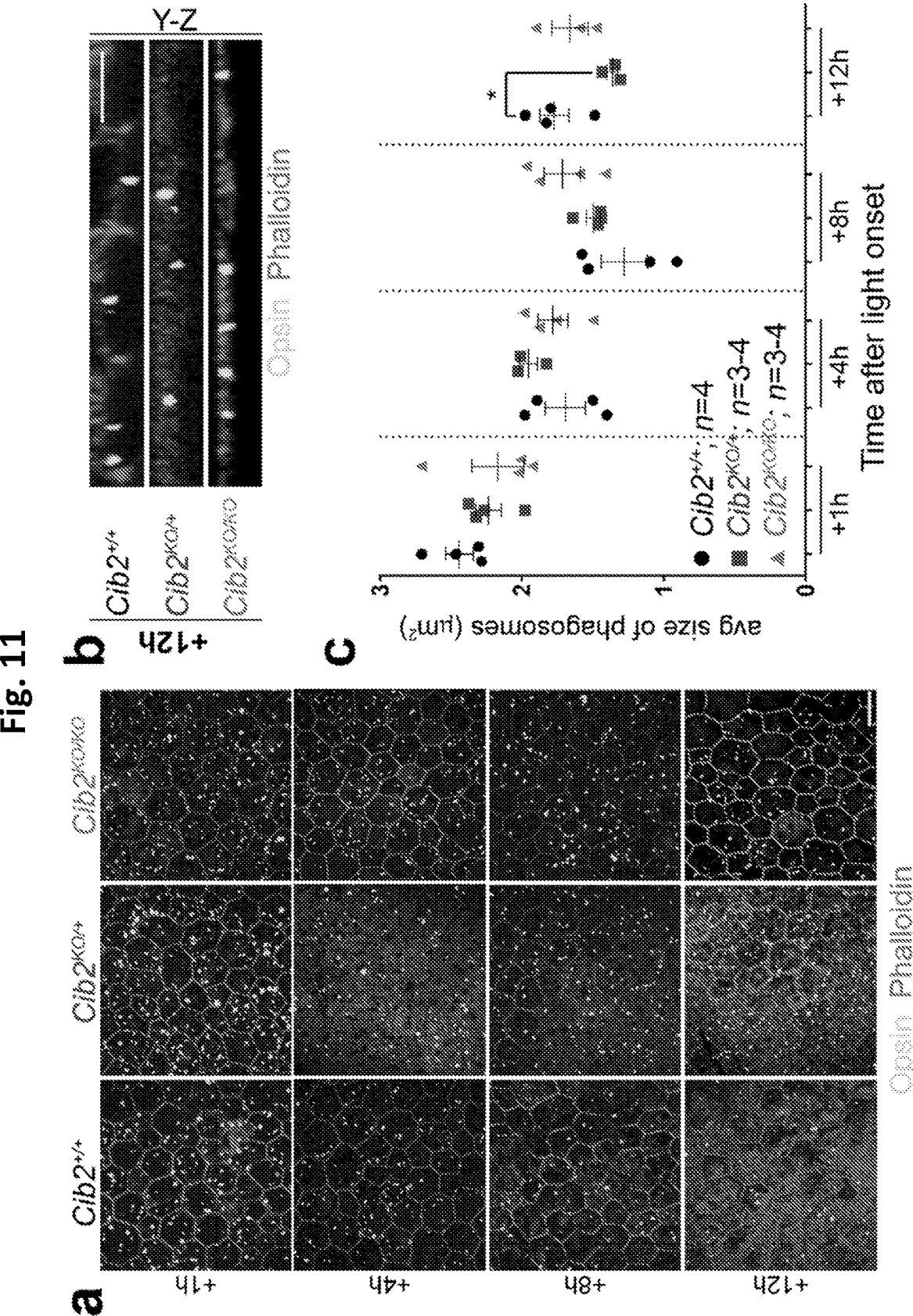

FIG. 11. Analysis of circadian LAP process revealed slower clearance of ingested OS segments. a, Confocal micrographs of flat mount RPE of indicated genotype and times from 3-4 month old mice showed declining opsin-positive phagosome with increasing time elapsed since lights-on. RPE flat mounts were stained for opsin Ret-P1 antibody (green) and phalloidin (red). In some images the phalloidin covers the entire scanned area, indicating the intact apical microvilli. b. Y-Z section from selected areas for the indicated genotypes and time elapsed since lights-on. In RPE of Cib2$^{KO}$ mice, the opsin-phagosomes were distributed more apically. c. Quantification of sizes of opsin-phagosomes with time elapsed indicates that in WT mice the size decreases in concert with time of day, while in mutant mice those changes are much slower, suggesting phagolysosomal digestion defects. Scale bar, 10 μm.

Figure 12:
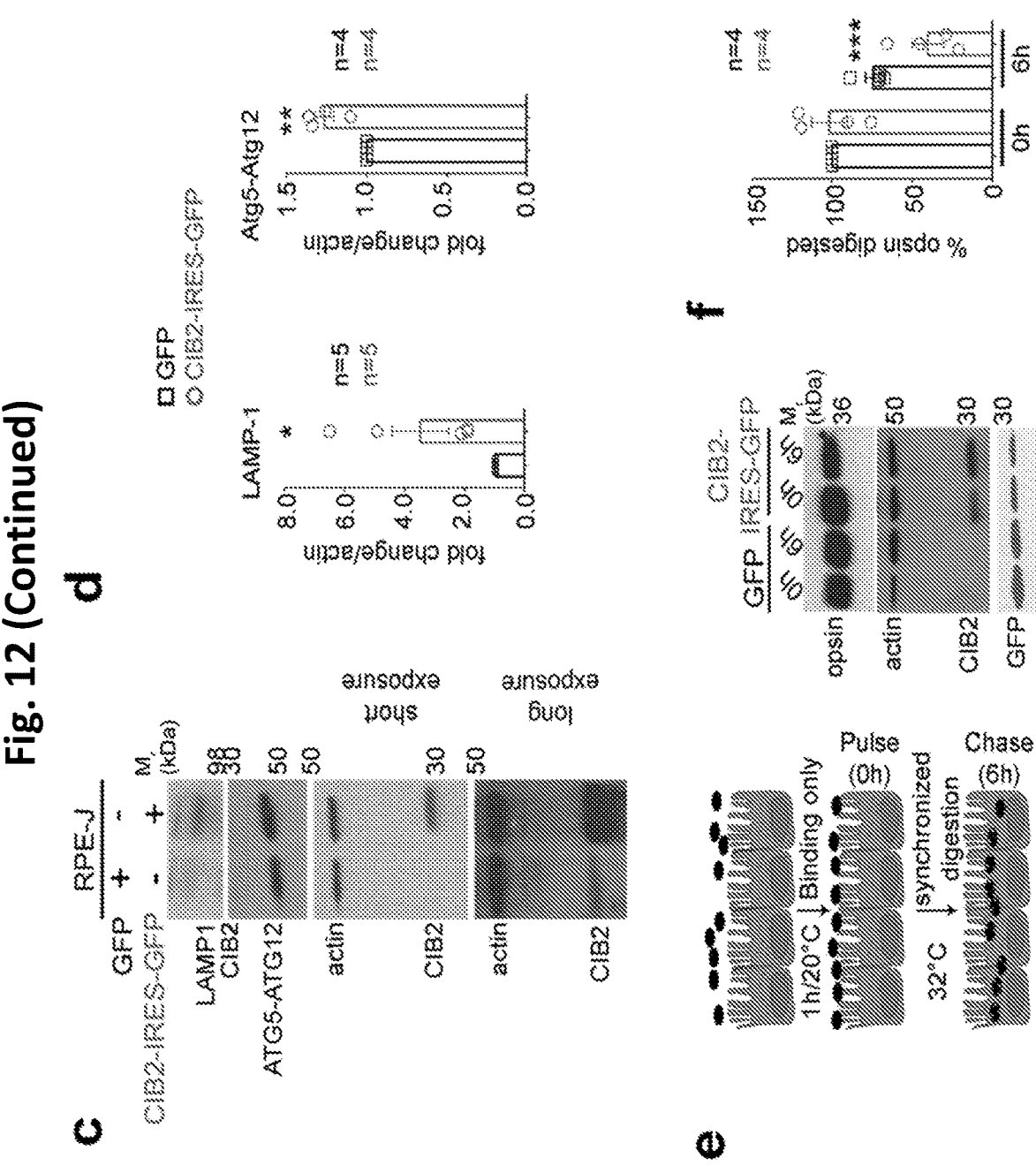

FIG. 12. CIB2 mutant mice have less autophagy/lysosomal proteins, and overexpression of CIB2. in vitro, is sufficient to boost levels of autophagy/lysosomal proteins and clearance of opsin. a. Representative immunoblots for denoted proteins from RPE/choroid lysates obtained from mice euthanized either 1 or 12 hr after light onset for denoted genotypes indicates that lysosomal/autophagy proteins levels were decreased in mutant mice at both time points assessed. ψ. pro-cathepsin D immunoblot was overexposed for mature-cathepsin D to be observable. b, Quantification for immunoblots shown in (a). n=3/genotype/time point. Pro-cathepsin D levels were quantified from non-saturated exposures. c. Representative immunoblots for indicated autophagy/lysosomal proteins from RPE-J cells transiently transfected with GFP or CIB2-IRES-GFP. Endogenous CIB2 is observable in long exposure immunoblot, while transiently overexpressed CIB2 is readily observable in short exposure immunoblot. d. Quantification for immunoblots shown in (c). n=5 (LAMP-1) or 4 (ATG5-ATG12) independent transfection experiments. e, Schematic of the pulse-chase phagocytosis assay (left panel)—also see Examples below. Representative opsin immunoblots (right panel) for cells pulsed with porcine OS for 1 hr at 20° C. (0 h) or chased with 5% serum (6 h) phagocytosis assay from RPE-J cells transiently transfected with GFP or CIB2-IRES-GFP show that initial binding is unaffected but lower amount of opsin at 6h in CIB2 over-expressing cells suggests faster clearance. f, Quantification for immunoblots shown in panel E. n=4 independent experiments. Opsin content for RPE cells transiently expressing GFP and pulsed with OS (0 h) was set to 100%. Unpaired two-tailed t test (b, d, f), p value of <0.05 (*), <0.01 (), <0.001 (*), NS—not significant.

Figure 13:
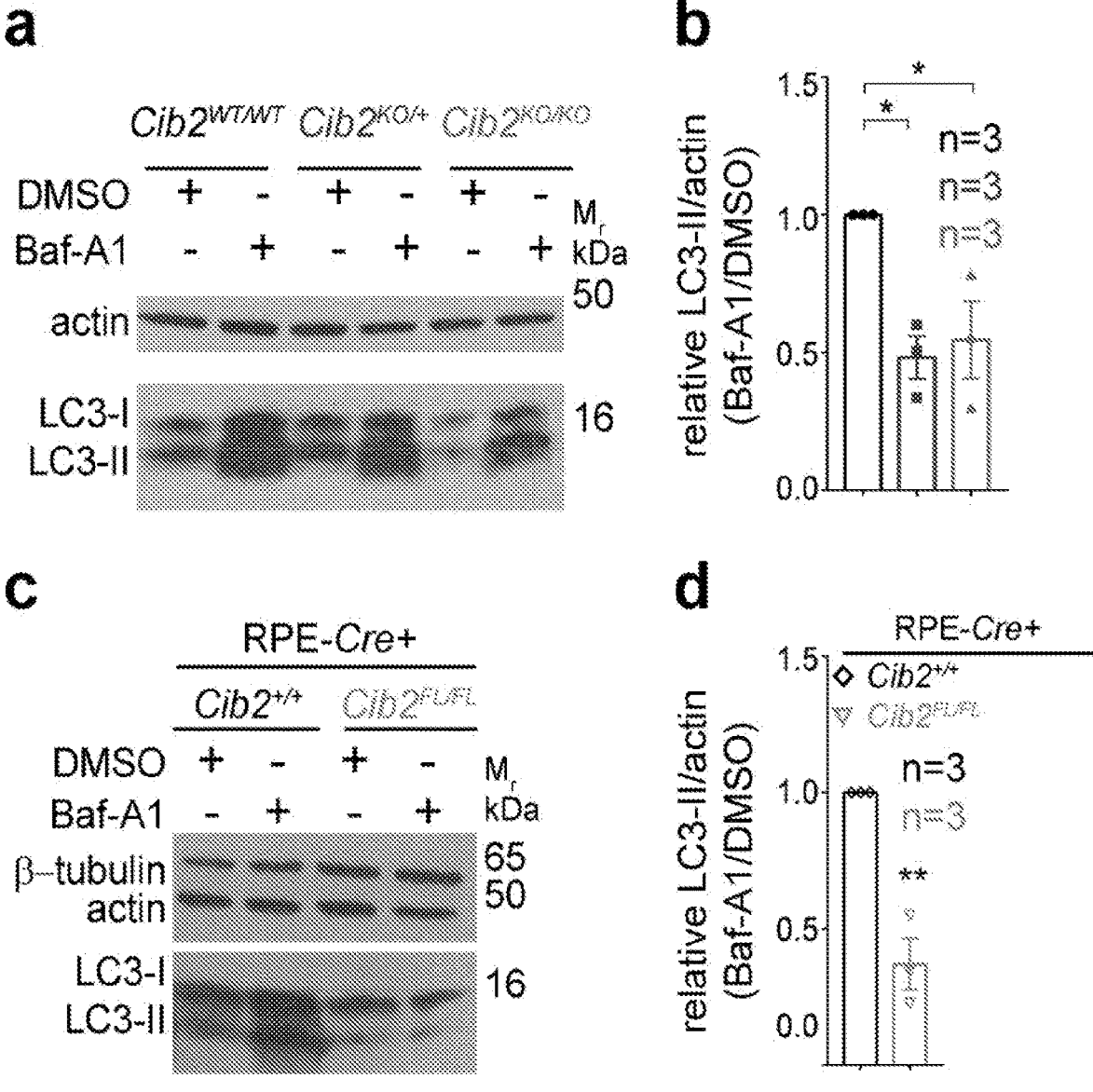
Figure 13:
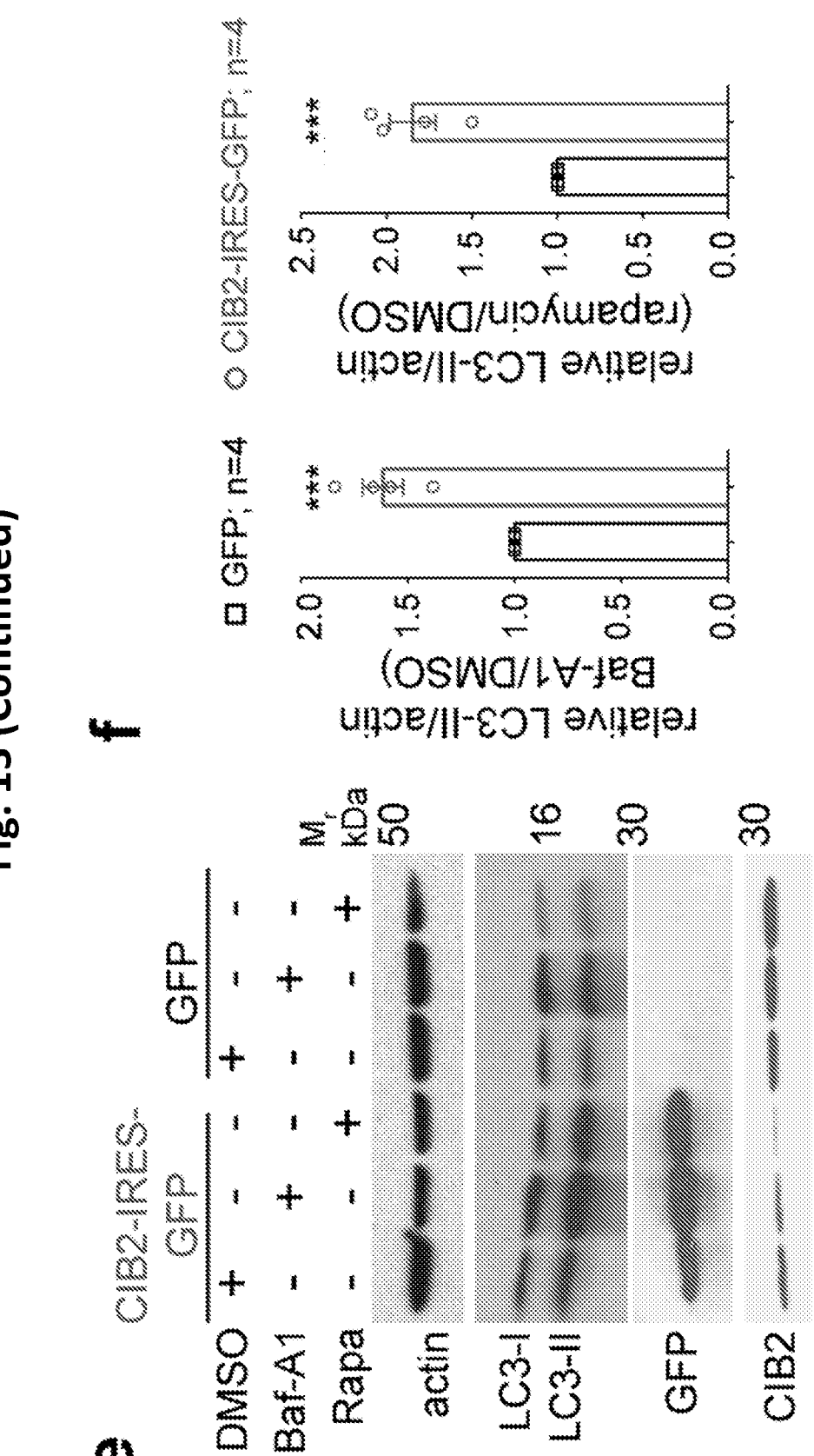

FIG. 13. Loss of CIB2, specifically in the RPE, leads to LC3 flux deficits, while CIB2 overexpression, in vitro, restores LC3 flux._a-d, RPE whole mounts treated with DMSO or 50 μM bafilomycin A1 (Baf-A1) overnight show reduced levels of LC3-II, quantified in panels b and d, in Cib2 deficient mice as compared to WT controls, indicating autophagy deficits. Ratio for WT or RPE-Cre+; Cib2+/+ was set to 1. e. Representative immunoblots for LC3-II induction in transiently transfected (GFP or CIB2-IRES-GFP) RPE-J cells treated with DMSO, 50 µM bafilomycin-A1 (Baf-A1), or 100 nM rapamycin (Rapa) for 24 hrs. f. Quantification of LC3 flux (ratio of LC3-II/actin in Baf-A1 to DMSO treated samples) or LC3B-II/actin ratio up on rapamycin treatment for immunoblots shown in (e). Ratio for GFP expressing cells was set to 1. n=4 independent experiment/treatment. One-way ANOVA and Bonferroni post hoc test (b) or unpaired two-tailed t test (d, f). p value of <0.05 (*), <0.01 (), or <0.001 (*).

Figure 14:
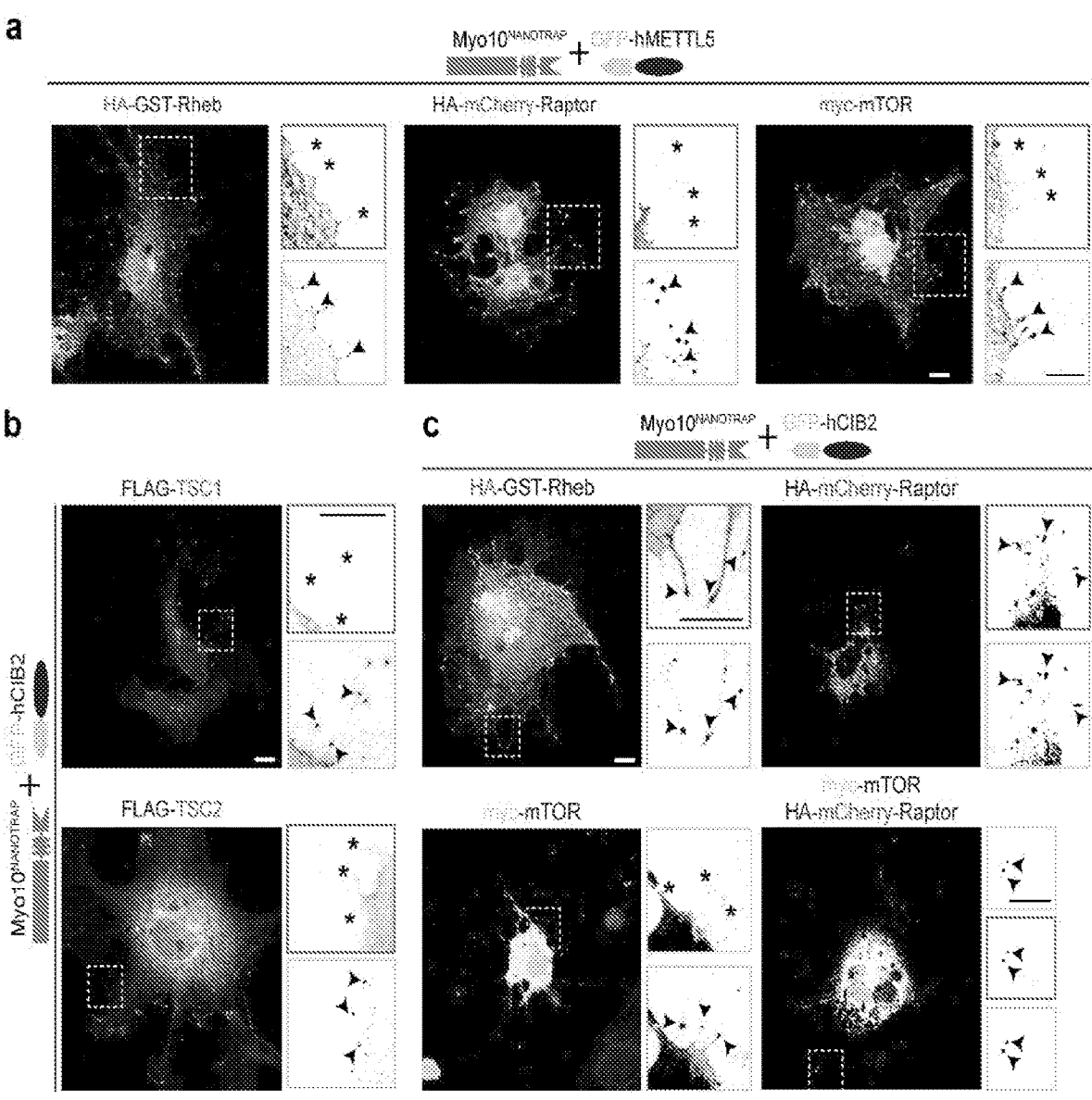
Figure 14:
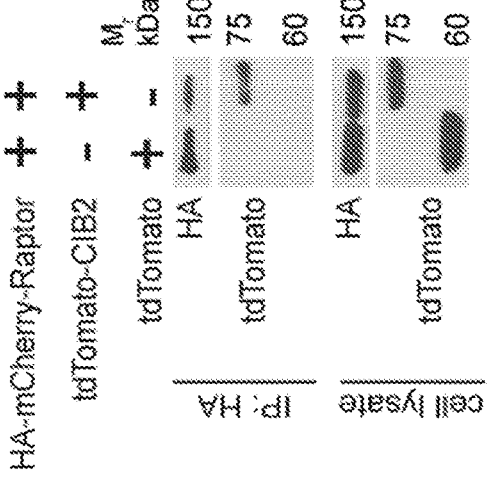
Figure 14:
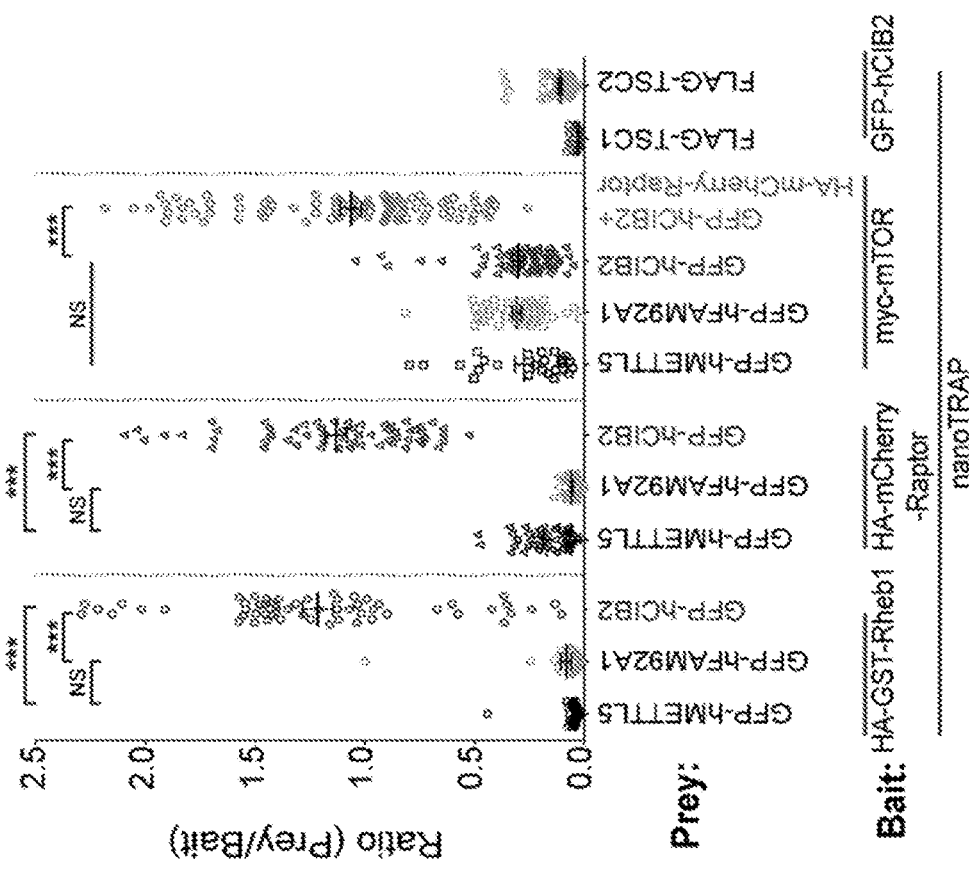

FIG. 14. Rheb-mTORC1 pathway analysis revealed CIB2 interacts with Rheb and forms a tripartite complex with mTOR via Raptor. a. Confocal micrographs of the HA-GST-Rheb, HA-mCherry-Raptor and myc-mTOR constructs transiently transfected with nanoTRAP and GFP-METTL5 (controls) in COS-7 cells. Arrowheads indicate accumulation of GFP-METTL5 at the tip of filopodia, * indicates absence of the indicated construct in the red channel at the filopodia tips, suggesting no interaction of tagged proteins with the nanoTRAP and control GFP-METTL5 construct. Similar results were obtained with nanoTRAP and GFP-FAM92A1 (control) construct. b, Confocal images for FLAG-tagged TSC1 (top panel) and TSC2 (bottom panel) and nanoTRAP plus GFP-hCIB2 shows no interaction for either protein with hCIB2-eGFP. Arrowheads indicate filopodia tip accumulation of hCIB2-eGFP, * indicates no accumulation of indicted constructs in the red channel. c. Representative confocal images (top panel) showing CIB2 (green) interaction with Rheb (red) and Raptor (red) using NanoTRAP assay. Bottom panel of merged images for indicated constructs in green: GFP-hCIB2, cyan: myc-mTOR, red: HA-mCherry-Raptor indicating that mTOR does not interact directly with CIB2 but forms a tripartite complex with Raptor and CIB2. Zoomed images of inset shows reverse color images of indicated constructs at the tip of filopodia. Arrowheads indicate filopodia tip accumulation of indicated constructs, * indicates no accumulation of indicted construct in the red or far-red channel. Scale bar: 10 µm. d. Quantification for nanoTRAP assay for images shown above. *** p<0.001 by one-way ANOVA. e, Co-IP experiments show interaction between Raptor and CIB2.

Figure 3:
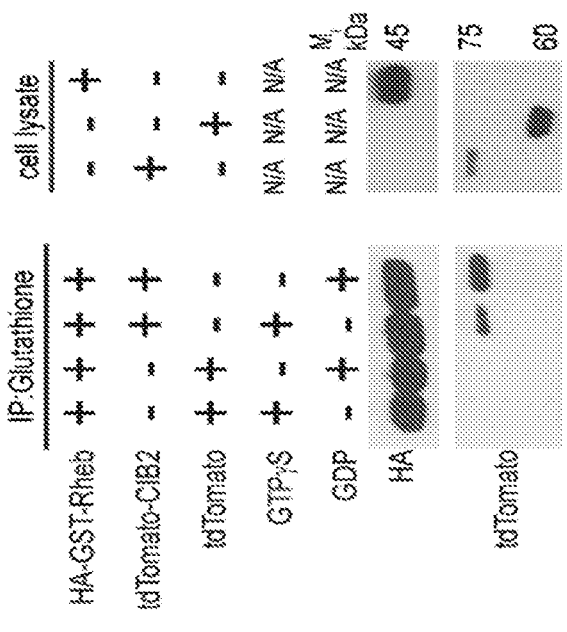
FIG. 3. CIB2 modulates mTORC1 signaling via preferentially binding to inactive-state of Rheb. a, Representative immunoblots of indicated phosphoproteins and total proteins from HEK293 lysates expressing increasing amounts of tdTomato-CIB2 and decreasing amounts of tdTomato (total amount of plasmid DNA for each condition is 9 μg), causing reduction in mTORC1 activity. b, Co-IP confirms interaction between tdTomato tagged CIB2 and HA-GST-Rheb variants. Note the stronger interaction between CIB2 and Rheb S20N variant as compared to Q64L variant (GDP vs GTP mimetic, respectively). c, CIB2 preferentially interacts with GDP-loaded Rheb is further confirmed by co-IP experiments of HA-GST-Rheb immobilized on GST beads and loaded with either GDP or GTPγS, followed by incubation with tdTomato-CIB2 lysate. d, Proposed model of CIB2 function in retinal sensory cells. Our data revealed that CIB2 is critical for regulating mTORC1 signaling and autophagy in RPE via interaction with GDP-Rheb (inactive form) and raptor. Loss of CIB2 results in reduced autophagy and exacerbated mTORC1 signaling, thus leading to RPE pathology and secondary PR dysfunction. e, f Immunoblots from RPE/choroid lysates from dry AMD or control age-matched donors indicate reduced CIB2 expression, overactive mTORC1 and reduced autophagy, quantified in panel f. Unpaired two-tailed 1 test was used to determine statistical significance. p value of <0.05 (*), <0.01 (), and <0.001 (*). Please note that one control sample (ψ) is outliner and is highly variant from the rest, Re-quantification, omitting the highly variant control sample, is shown in FIG. 15. g. Immunoblots from lymphangioleiomyomatosis patient-derived cell line (LAM-621; left panel) or TSC2$^{-/-}$, p53$^{-/-}$ mouse embryonic fibroblasts (MEF; right panel) lysates over-expressing either tdTomato or CIB2 show that in absence of TSC, CIB2 can partially reduce the overactive mTORC1 signaling.
Figure 3:
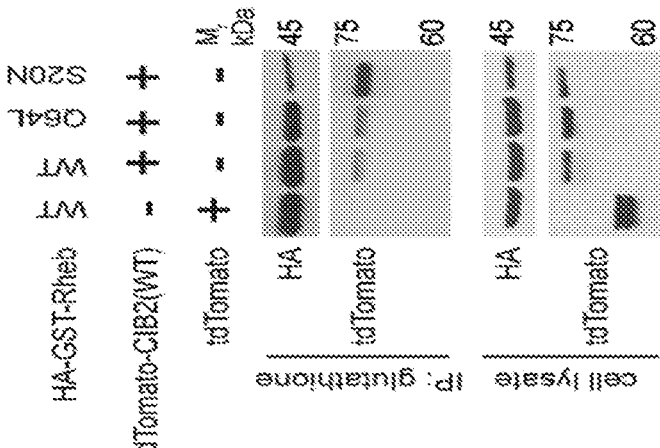
Figure 3:
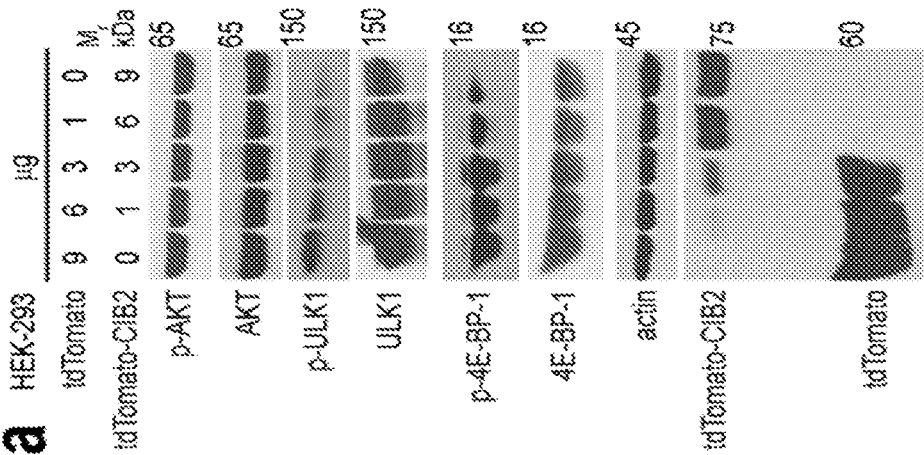
Figure 3:
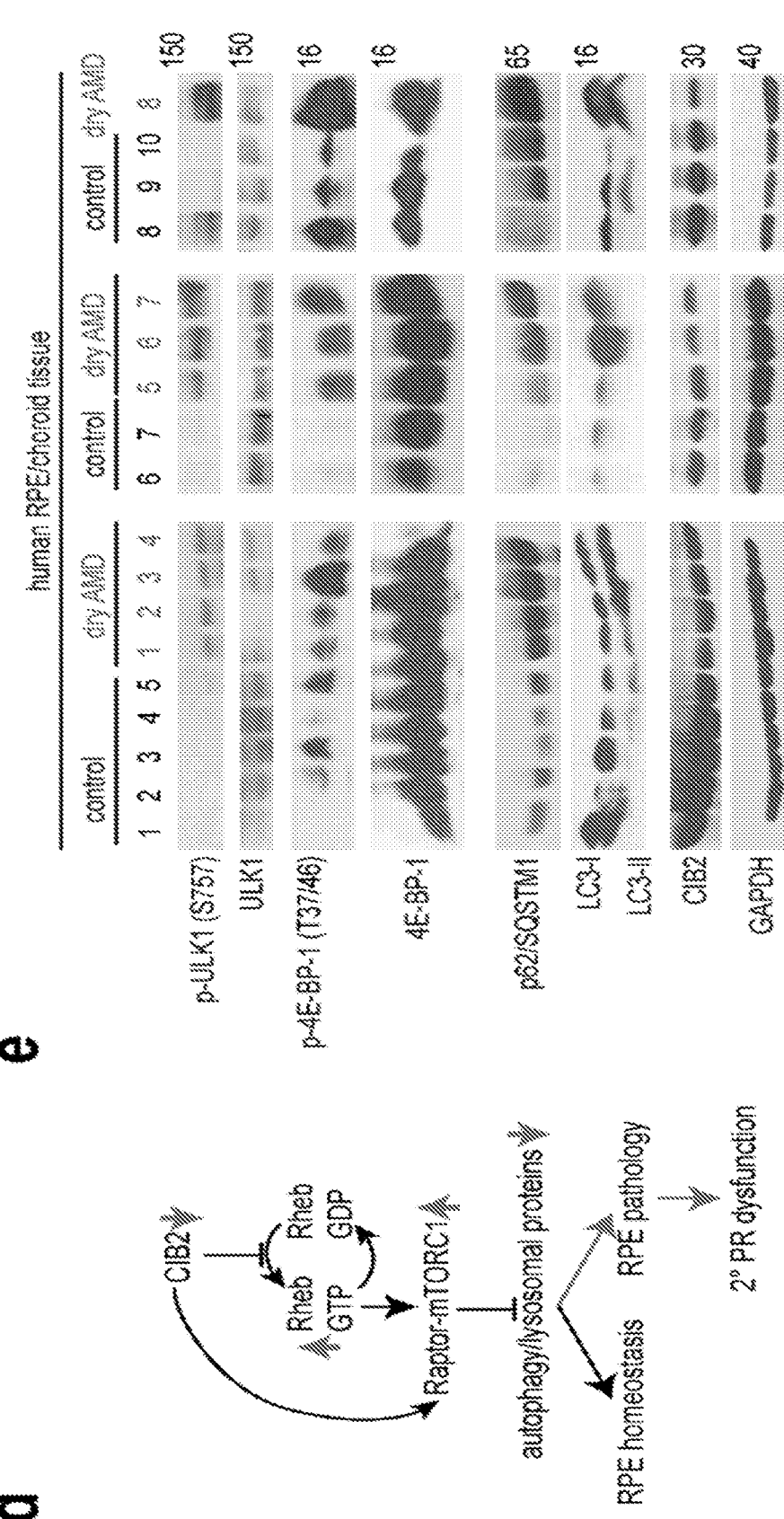
Figure 3:
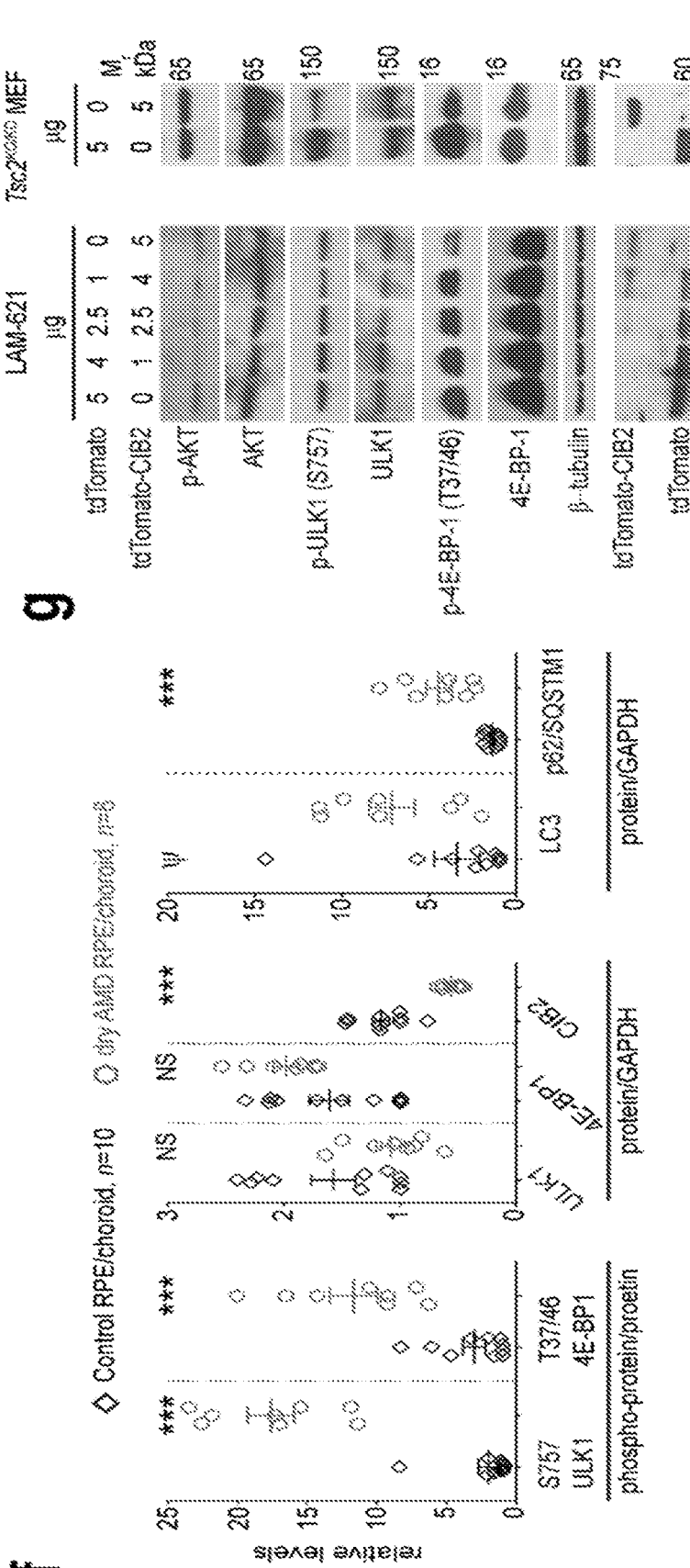
Figure 15:
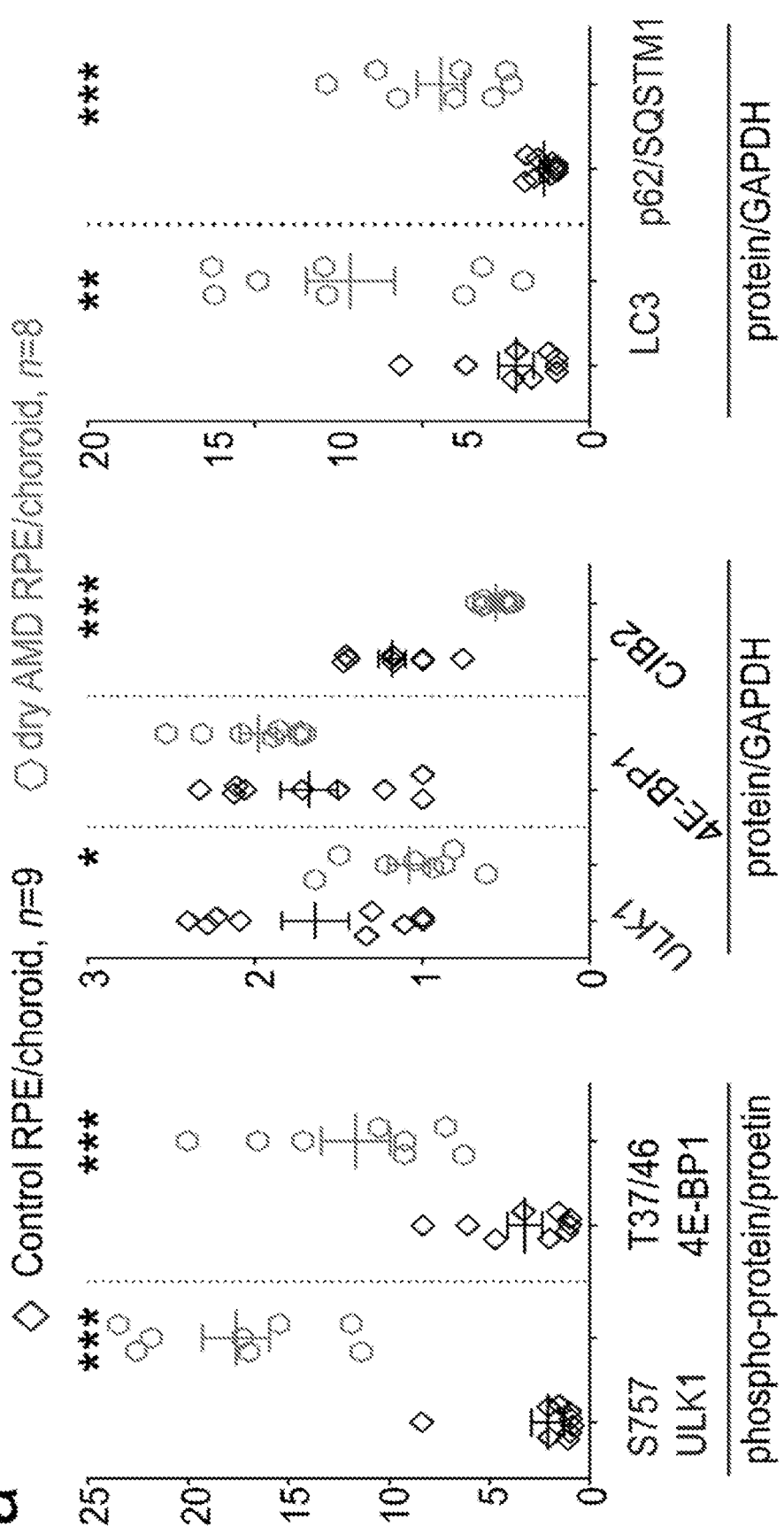

FIG. 15. mTORC1 dysregulation in RPE/choroid lysates from dry AMD cases. a, Re-quantification of blots shown in FIG. 3f with the outlier control sample (FIG. 3g, ψ omitted for quantification. Unpaired two-tailed t test was used to determine statistical significance. P value of <0.05 (*), <0.01 (), and <0.001 (*).

Figure 16:
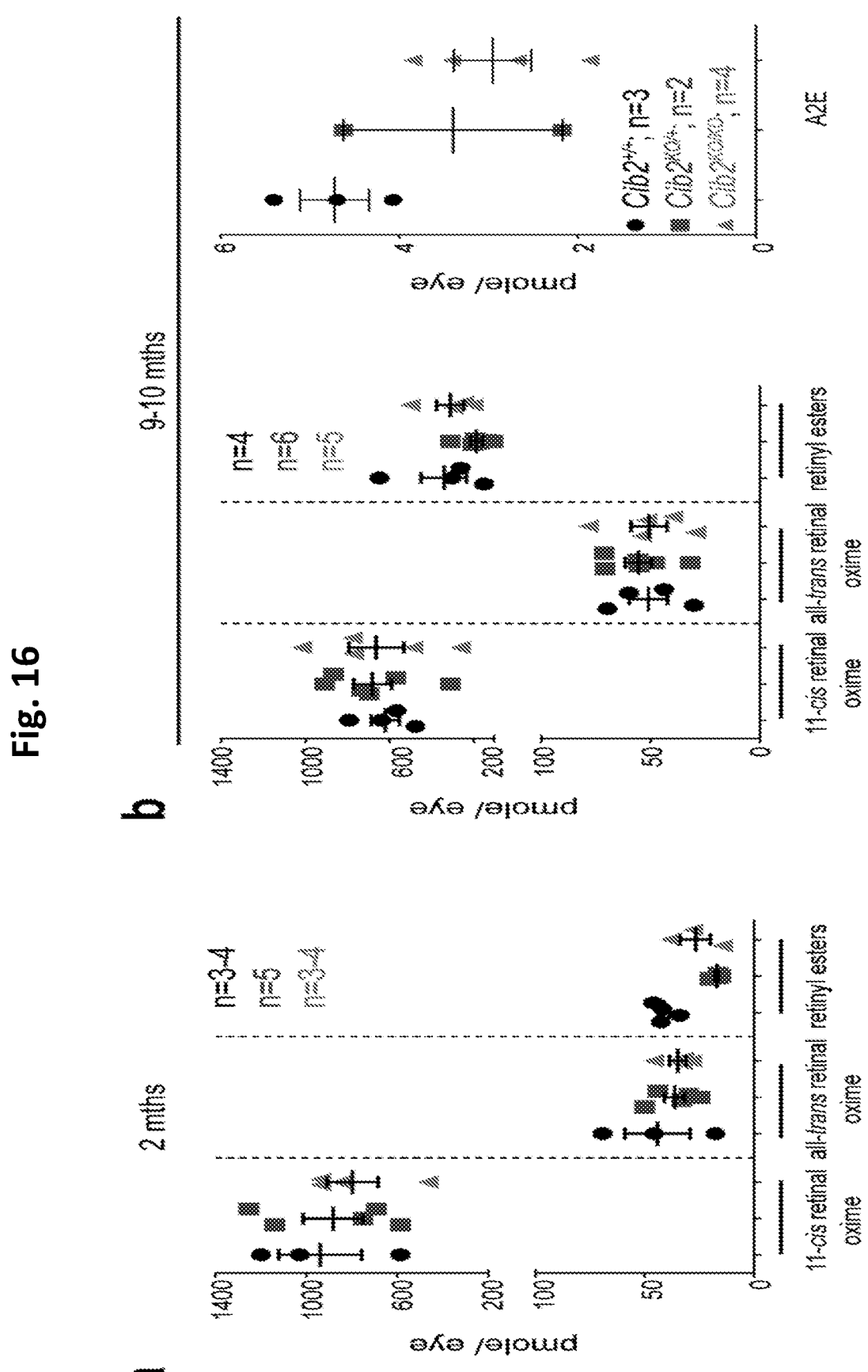

FIG. 16. Analysis of retinoid data shows no significant differences in the retinoid species in Cib2 mutant mice. a, b, Retinoid quantification for indicated retinal derivatives at ages 2 months (a) and 9-10 months (b) revealed no statistically significant differences between control and mutant mice.

Figure 17:
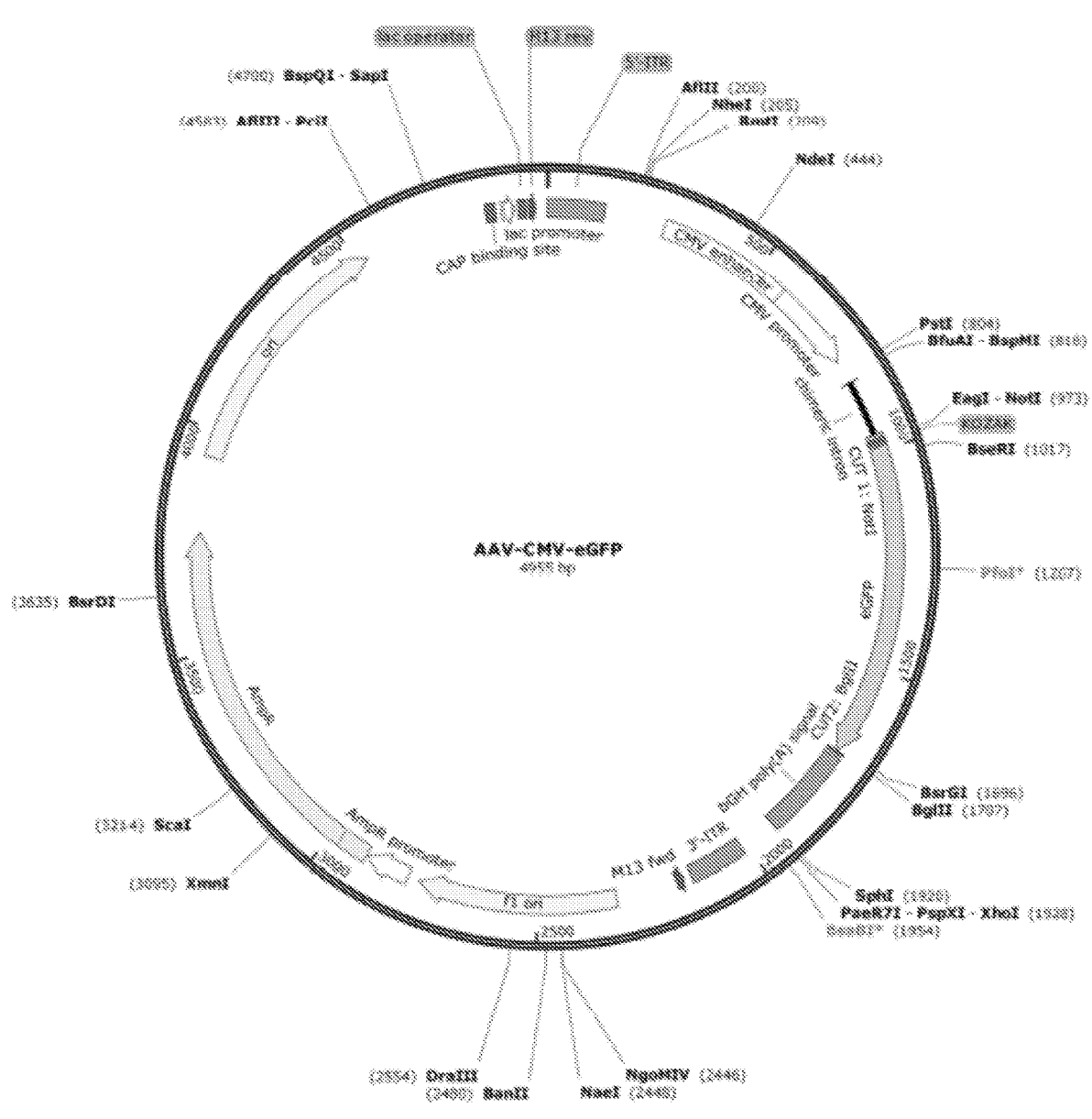

FIG. 17. Schematic of AAV.CMV.eGFP vector construct.

Figure 18:
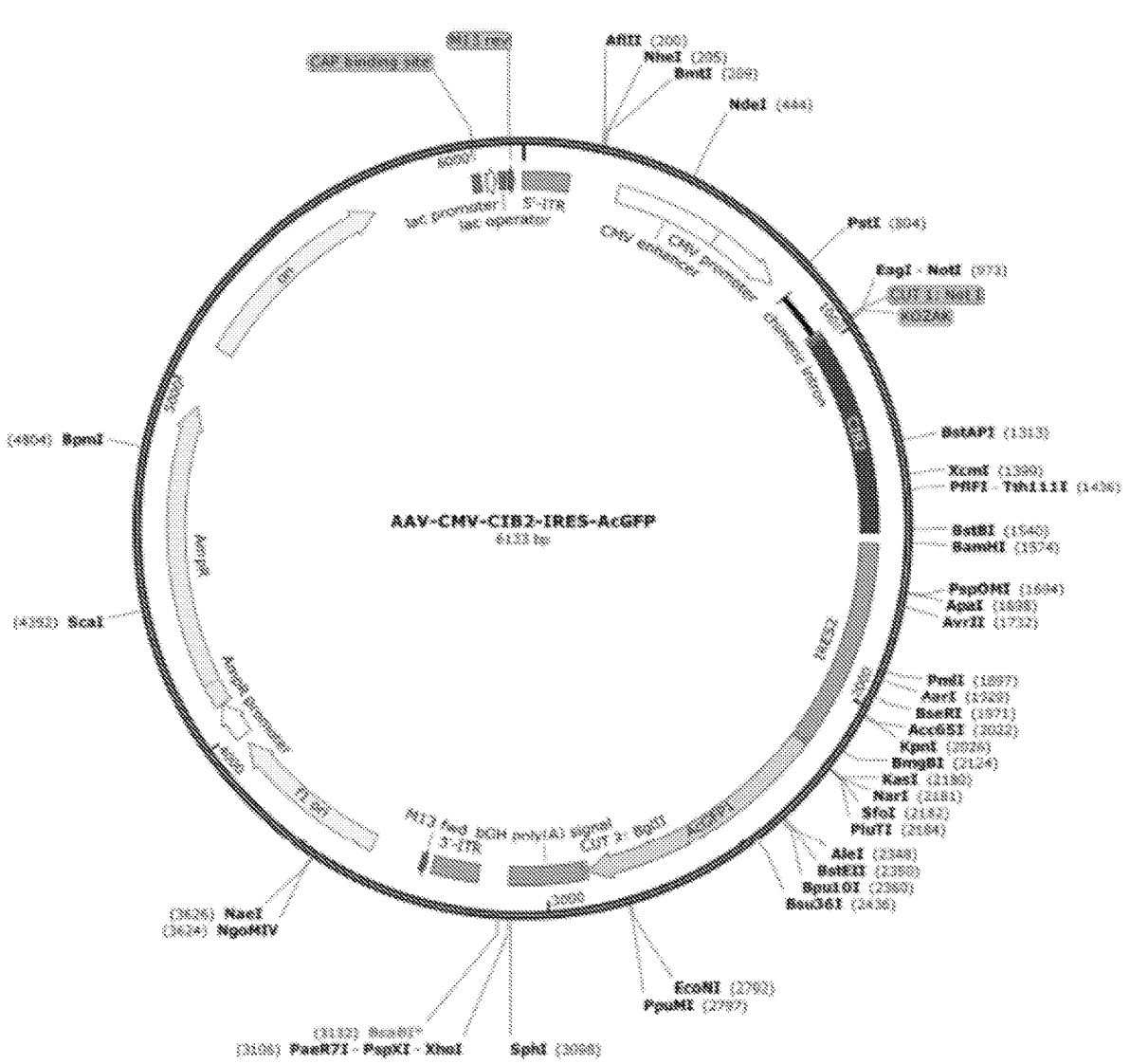

FIG. 18. Schematic of AAV.CMV.Cib2-IRES-AcGFP vector construct.

Figure 19:
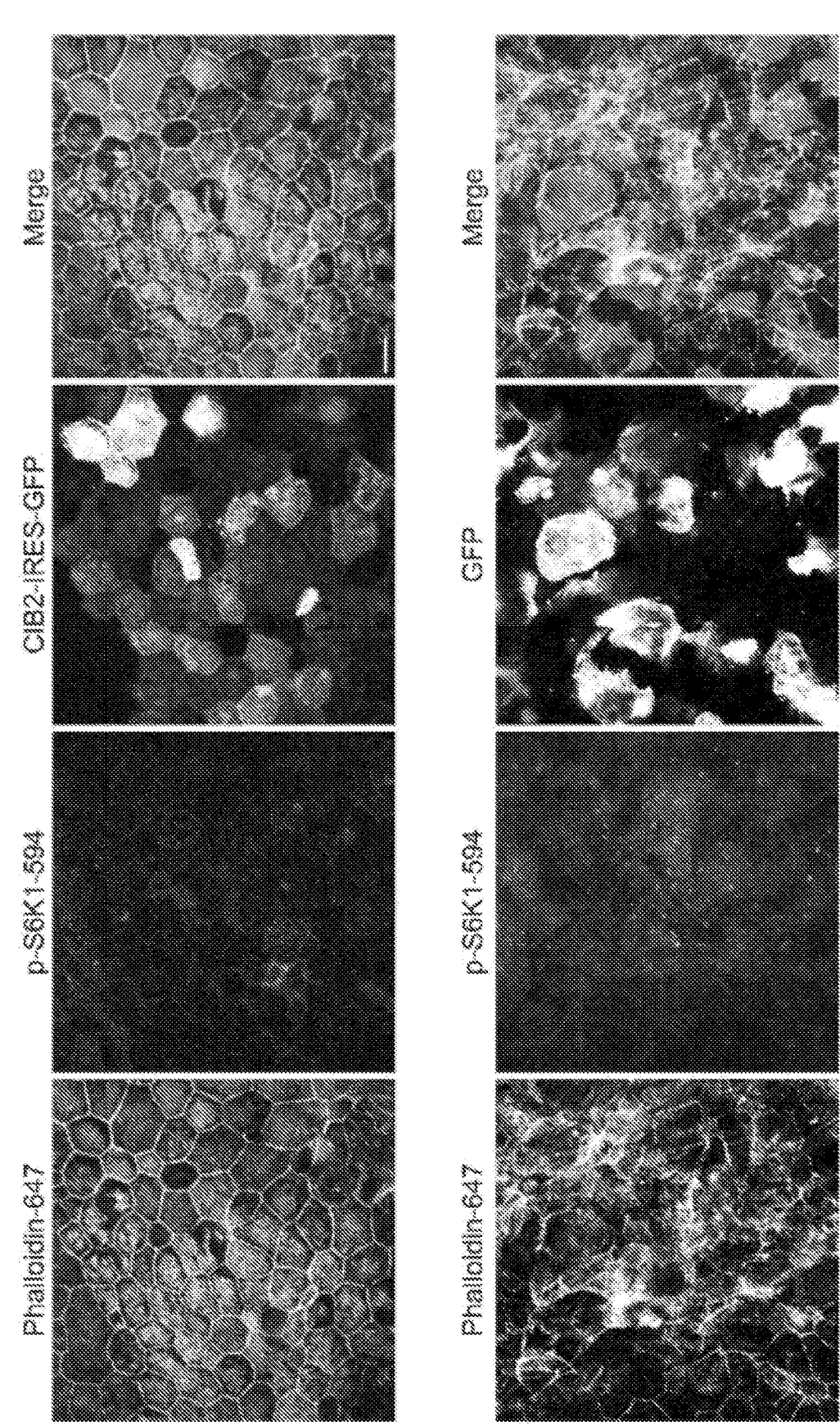

FIG. 19. RPE-specific Cib2$^{KO}$ mice were subretinally injected with 1 µl of Anc80-CIB2-IRES-AcGFP (top panel) or Anc80-eGFP virus (bottom panel. 1-2 weeks after injection, the mice were starved of food for 24 hrs to induce in vivo autophagy. After enucleating the eyes, the retina was separated from the RPE/choroid. RPE/choroid whole mounts were stained for phospho-S6K1 (direct target of mTORC1). The photomicrographs show higher p-S6K1 in RPE cells from mice injected with the negative control GFP virus (bottom panel) as compared to the experimental CIB2-IRES-GFP virus (top panel), suggesting exogenous expression of CIB2 is sufficient to reduce overactive mTORC1 signaling.

DETAILED DESCRIPTION OF THE INVENTION

The invention is based at least in part on the discovery that increased levels of CIB2 can increase autophagy flux in cells. Mammalian target of rapamycin complex 1 (mTORC1) is the central integrator of nutrient and stress signals. mTORC1 negatively regulates autophagy, which is essential for cellular homeostasis. Directly inhibiting mTORC1 (via rapamycin or rapalogs) for short duration successfully decreases mTORC1 activity, however, it has gross negative long-term effects including cell death. Rheb, a small GTPase, is an obligate activator of mTORC1 (but not mTORC2) on the lysosomal surface. Rheb in the GTP bound state potently activates mTORC1. Calcium and integrin binding protein 2 (CIB2) specifically binds to the GDP-bound (inactive state) Rheb. This leads to downregulation of mTORC1 signaling. Increasing the amount of CIB2 leads to higher autophagy flux, more lysosomal/autophagy proteins. CIB2 deletion in mouse models, particularly retinal pigment epithelium (RPE), leads to aberrant mTORC1 activation, slower phagolysosomal digestion of outer segment discs, lower autophagy flux, and secondary photoreceptor dysfunction. CIB2 over-expression (or peptide derived from CIB2) via gene/peptide delivery/genome editing in such disorders will down-regulate mTORC1 signaling and help improve primary and secondary symptoms.

Reference will now be made in detail to the presently preferred embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

In some aspects, the practice of the present invention employs various techniques of molecular biology (including recombinant techniques), microbiology, cell biology, biochemistry and immunology. See, e.g., Sambrook et al. *Molecular Cloning: A Laboratory Manual, 2$^{nd}$* edition (1989); *Current Protocols in Molecular Biology* (F. M. Ausubel et al. eds. (1987)); the series *Methods in Enzymology* (Academic Press, Inc.); *PCR: A Practical Approach* (M. MacPherson et al. IRL Press at Oxford University Press (1991)); *PCR 2: A Practical Approach* (M. J. MacPherson, B. D. Hames and G. R. Taylor eds. (1995)); *Antibodies, A Laboratory Manual* (Harlow and Lane eds. (1988)); *Using Antibodies, A Laboratory Manual* (Harlow and Lane eds. (1999)); and *Animal Cell Culture* (R. I. Freshney ed. (1987)).

Definitions of common terms in molecular biology may be found, for example, in Benjamin Lewin, *Genes VII,* published by Oxford University Press, 2000 (ISBN 019879276X); Kendrew et al. (eds.); *The Encyclopedia of Molecular Biology,* published by Blackwell Publishers, 1994 (ISBN 0632021829); and Robert A. Meyers (ed.),

*Molecular Biology and Biotechnology: a Comprehensive Desk Reference*, published by Wiley, John & Sons, Inc., 1995 (ISBN 0471186341).

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. As used in the specification and claims, the singular form "a," "an" and "the" include plural references unless the context clearly dictates otherwise. For example, the term "an antibody" includes a plurality of antibodies, including mixtures thereof. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" means plus or minus 10% of the numerical value of the number with which it is being used.

The terms "nucleic acid," and "polynucleotide," are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids. The term "sequence" relates to a nucleotide sequence of any length, which can be DNA or RNA; can be linear, circular or branched and can be either single-stranded or double stranded.

The term "identity" relates to an exact nucleotide-to-nucleotide or amino acid-to-amino acid correspondence of two polynucleotides or polypeptide sequences, respectively. Two or more sequences (polynucleotide or amino acid) can be compared by determining their percent identity. Calculations of homology or sequence identity between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frame shift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

"Sequence similarity" between polynucleotides can be determined by hybridization of polynucleotides under conditions that allow formation of stable duplexes between homologous regions, followed by digestion with single-stranded-specific nuclease(s), and size determination of the digested fragments.

The terms "inhibiting," "reducing," or "prevention," or any variation of these terms, when used in the claims and/or the specification includes any measurable decrease or complete inhibition to achieve a desired result. For example, there may be a decrease of 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal.

Methods

In one embodiment, the invention provides a method for down-regulating mTORC1 signaling in a subject, comprising administering to the subject an effective amount of one or more compositions that increase activity of CIB2 or a biologically active fragment or variant thereof in the subject.

In another embodiment, the invention provides a method for down-regulating mTORC1 signaling in a subject, comprising administering to the subject an effective amount of one or more compositions that promote increased levels of CIB2 or a biologically active fragment or variant thereof in the subject.

In another embodiment, the invention provides a method for down-regulating mTORC1 signaling in a cell, comprising administering to the cell an effective amount of one or more compositions that increase activity of CIB2 or a biologically active fragment or variant thereof in the cell.

In another embodiment, the invention provides a method for down-regulating mTORC1 signaling in a cell, comprising administering to the cell an effective amount of one or more compositions that promote increased levels of CIB2 or a biologically active fragment or variant thereof in the cell.

In another embodiment, the invention provides a method for treating a disease, condition, or disorder which would benefit from down-regulation of mTORC1 signaling in a subject, comprising administering to the subject an effective amount of one or more compositions that increase activity of CIB2 or a biologically active fragment or variant thereof, thereby treating the disease, condition, or disorder in the subject.

In another embodiment, the invention provides a method for treating a disease, condition, or disorder which would benefit from down-regulation of mTORC1 signaling in a subject, comprising administering to the subject an effective amount of one or more compositions that promote increased levels of CIB2 or a biologically active fragment or variant thereof, thereby treating the disease, condition, or disorder in the subject.

In another embodiment, the invention provides a method for increasing autophagy and/or phagolysosomal digestion in cells, comprising administering to the cells an effective amount of one or more compositions that increase activity of CIB2 or a biologically active fragment or variant thereof in the cells.

In another embodiment, the invention provides a method for increasing autophagy and/or phagolysosomal digestion in cells, comprising administering to the cells an effective amount of one or more compositions that promote increased levels of CIB2 or a biologically active fragment or variant thereof in the cells.

In another embodiment, the invention provides a method for increasing autophagy and/or phagolysosomal digestion in a subject, comprising administering to the subject an effective amount of one or more compositions that increase activity of CIB2 or a biologically active fragment or variant thereof in the subject.

In another embodiment, the invention provides a method for increasing autophagy and/or phagolysosomal digestion in a subject, comprising administering to the subject an effective amount of one or more compositions that promote increased levels of CIB2 or a biologically active fragment or variant thereof in the subject.

In some embodiments, the composition comprises a polypeptide comprising CIB2 or a biologically active fragment or variant thereof. In some embodiments, the polypeptide is a fusion protein comprising a protein transduction domain.

In some embodiments, the composition comprises a nucleic acid encoding CIB2 or a biologically active fragment or variant thereof. In some embodiments, an effective amount of a viral vector comprising the nucleic acid is administered.

As used herein, "treat" and all its forms and tenses (including, for example, treating, treated, and treatment) refers to therapeutic and prophylactic treatment. In certain aspects of the invention, those in need of treatment include those already with a pathological disease or condition of the invention, in which case treating refers to administering to a subject (including, for example, a human or other mammal in need of treatment) a therapeutically effective amount of a composition so that the subject has an improvement in a sign or symptom of a pathological condition of the invention and/or a slowing of disease onset and/or progression. The improvement may be any observable or measurable improvement. Thus, one of skill in the art realizes that a treatment may improve the patient's condition, but may not be a complete cure of the disease or pathological condition.

In accordance with the invention, a "therapeutically effective amount" or "effective amount" is administered to the subject. As used herein a "therapeutically effective amount" or "effective amount" is an amount sufficient to decrease, suppress, or ameliorate one or more symptoms associated with the disease or condition.

The subject to be treated herein is not limiting. In some embodiments, the subject to be treated is a mammal, bird, reptile or fish. Mammals that can be treated in accordance with the invention, include, but are not limited to, humans, dogs, cats, horses, mice, rats, guinea pigs, sheep, cows, pigs, monkeys, apes and the like. The term "patient" and "subject" are used interchangeably. In some embodiments, the subject is a human.

The therapeutic compositions can be administered one time or more than one time, for example, more than once per day, daily, weekly, monthly, or annually. The duration of treatment is not particularly limiting. The duration of administration of the therapeutic composition can vary for each individual to be treated/administered depending on the individual cases and the diseases or conditions to be treated. In some embodiments, the therapeutic composition can be administered continuously for a period of several days, weeks, months, or years of treatment or can be intermittently administered where the individual is administered the therapeutic composition for a period of time, followed by a period of time where they are not treated, and then a period of time where treatment resumes as needed to treat the disease or condition. For example, in some embodiments, the individual to be treated is administered the therapeutic composition of the invention daily, every other day, every three days, every four days, 2 days per week 3 days per week, 4 days per week, 5 days per week or 7 days per week. In some embodiments, the individual is administered the therapeutic composition for 1 week, 2 weeks, 3 weeks, 4 weeks, 1 month, 2 months, 3 months, 4 months, 5 months, 6 months, 7 months, 8 months, 9 months, 10 months, 11 months, 1 year, or longer.

In some embodiments, the disease, condition, or disorder is selected from ageing, cancer, hemangioma, obesity, epilepsy, autism, Alzheimer's, Tuberous Sclerosis Complex, lymphangioleiomyomatosis (LAM), tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, macular degeneration, Stargardt disease, and age-related macular degeneration (e.g., dry and/or wet), or any other genetic disease/disorder in which mTORC1 is hyperactive. In some embodiments, the cancer is selected from, glioma, melanoma, sarcoma and ovarian, breast, lung, pancreatic, prostate, colon, and epidermoid cancer. Without being bound by theory as to how the invention works, in some embodiments, the method increases canonical and non-canonical autophagy in cells.

The cells to be treated are not particularly limiting. In some embodiments, the cells comprise retinal pigment epithelium (RPE) cells. In some embodiments, the cells comprise epithelial cells, neurons, astrocytes, microglia, macrophages, or cells derived from the listed lineages.

In some embodiments, the method comprises increasing the activity of CIB2 in RPE or other cells listed above. In some embodiments, increasing the activity of CIB2 encompasses increasing the binding of CIB2 to Rheb protein in a cell, particularly the GDP-bound state of Rheb. The activity level can be increased, for example, by administering an agent that facilitates the interaction between the GDP-bound state of Rheb and CIB2. In some embodiments, the activity of CIB2 or a biologically active fragment or variant thereof can be increased by increasing the levels of the polypeptide in the cell.

Methods for increasing levels of CIB2 or a biologically active fragment or variant thereof are not particularly limiting and can include, for example, administering a composition comprising the polypeptide or administering a nucleic acid encoding the polypeptide. In some embodiments, a combination of polypeptides and nucleic acids can be administered. In some embodiments, the nucleic acids comprise mRNA. In some embodiments, one or more viral vectors comprising the nucleic acid are administered.

In some embodiments, one or more compositions that genetically modify cells are administered to increase levels or activity of CIB2. The types of genetic modification or genomic editing are not particularly limiting provided that the modification results in an increase in activity or levels of CIB2 or a biologically active fragment or variant thereof in the cells.

In some embodiments human CIB2 polypeptide comprises the sequence as shown below (SEQ ID NO:1). >sp|O75838|CIB2_HUMAN Calcium and integrin-binding family member 2 OS-*Homo sapiens* OX=9606 GN=CIB2 PE=1 SV=1

(SEQ ID NO: 1)
MGNKQTIFTEEQLDNYQDCTFFNKKDILKLHSRFYELAPNLVPMDYRKS

PIVHVPMSLIIQMPELRENPFKERIVAAFSEDGEGNLTFNDFVDMFSVL

CESAPRELKANYAFKIYDFNTDNFICKEDLELTLARLTKSELDEEEVVL

VCDKVIEEADLDGDGKLGFADFEDMIAKAPDFLSTFHIRI.

(SEQ ID NO:2). >sp|Q9Z309|CIB2_MOUSE Calcium and integrin-binding family member 2 OS=*Mus musculus* OX=10090 GN=Cib2 PE=1 SV=1

MGNKQTIFTEEQLDNYQDCTFFNKKDILKLHARFYELAPNLVPMDYRKS

PIVHVPMSLIIQMPELRENPFKERIVEAFSEDGEGNLTFNDFVDMFSVL

CESAPRELKANYAFKIYDFNTDNFICKEDLEMTLARLTKSELEEDEVVL

VCDKVIEEADLDGDGKLGFADFEDMIAKAPDFLSTFHIRI

In some embodiments, human CIB2 is encoded by a nucleotide sequence that encodes an amino acid sequence comprising SEQ ID NO:1 or mouse CIB2 sequence (SEQ ID NO: 2) or a biologically active fragment or variant thereof.

In some embodiments human CIB2 is encoded by a nucleotide sequence comprising SEQ ID NO:3, as shown below.

ATGGGGAACAAGCAGACCATCTTCACCGAAGAGCAGCTAGACAACTACC

AGGACTGCACCTTCTTCAATAAGAAGGACATCCTCAAGCTGCATTCGCG

ATTCTATGAGCTGGCCCCCAACCTCGTCCCAATGGACTACAGGAAGAGC

CCCATCGTCCACGTGCCCATGAGCCTCATCATCCAGATGCCAGAGCTCC

GGGAGAATCCCTTCAAAGAAAGGATCGTGGCGGCGTTTTCCGAGGATGG

TGAGGGGAACCTCACTTTCAACGACTTTGTGGACATGTTTTCCGTGCTC

TGCGAGTCGGCTCCCCGAGAGCTCAAGGCAAACTATGCCTTCAAGATCT

ATGACTTCAACACTGACAACTTCATCTGCAAGGAGGACCTGGAGCTGAC

GCTGGCCCGGCTCACTAAGTCAGAGCTGGATGAGGAGGAGGTGGTGCTT

GTGTGCGACAAGGTCATTGAGGAGGCTGACTTGGACGGTGACGGCAAGC

TGGGCTTTGCTGACTTCGAGGACATGATTGCCAAGGCCCCTGACTTCCT

CAGCACTTTCCACATCCGGATCTGA.

mouse CIB2

(SEQ ID NO: 4)
ATGGGGAACAAGCAGACCATCTTCACTGAAGAGCAGCTGGACAACTACC

AGGACTGCACTTTCTTCAATAAGAAGGACATCCTCAAGCTTCATGCACG

GTTCTATGAGCTGGCTCCCAACCTCGTCCCGATGGACTACAGGAAGAGT

CCCATCGTCCATGTACCCATGAGCCTCATCATTCAGATGCCGGAGCTCC

GGGAGAATCCCTTCAAAGAGAGGATTGTGGAGGCTTTCTCCGAGGATGG

CGAGGGGAACCTCACCTTCAATGACTTTGTGGACATGTTCTCTGTGCTC

TGCGAATCAGCGCCTCGGGAGCTCAAGGCAAACTATGCCTTCAAGATCT

ATGACTTCAACACTGACAATTTCATCTGTAAAGAAGACTTAGAGATGAC

GCTGGCCCGACTCACCAAGTCTGAGTTGGAAGAGGATGAGGTAGTGCTT

GTGTGTGACAAAGTCATTGAAGAGGCTGACCTGGATGGTGACGGCAAGC

-continued
TGGGCTTTGCTGACTTTGAGGACATGATCGCCAAGGCCCCTGATTTTCT

CAGCACCTTCCACATTCGAATCTGA

In some embodiments, nucleic acids can be administered to the subject either as naked nucleic acid, in conjunction with a delivery reagent, or as a recombinant plasmid or viral vector that expresses the nucleic acids. Delivery of naked nucleic acids or vectors to an individual may occur by any suitable means, but in specific embodiments it occurs by one of the following: cyclodextrin delivery system; ionizable lipids; DPC conjugates; GalNAc-conjugates; self-assembly of oligonucleotide nanoparticles (DNA tetrahedra carrying multiple siRNAs); or polymeric nanoparticles made of low-molecular-weight polyamines and lipids (see Kanasty et al. Nature Materials 12, 967-977 (2013) for review of same).

In some embodiments, the levels of CIB2 or a biologically active fragment or variant thereof are increased by administering a viral vector encoding the same.

The viral vector is not limiting. In some embodiments, the viral vector will typically comprise a highly attenuated, non-replicative virus. Viral vectors include, but are not limited to, DNA viral vectors such as those based on adenoviruses, herpes simplex virus, avian viruses, such as Newcastle disease virus, poxviruses such as vaccinia virus, and parvoviruses, including adeno-associated virus; and RNA viral vectors, including, but not limited to, the retro-viral vectors. Vaccinia vectors and methods useful in immunization protocols are described in U.S. Pat. No. 4,722,848. Retroviral vectors include murine leukemia virus, and lentiviruses such as human immunodeficiency virus. Naldini et al. (1996) *Science* 272:263-267. Replication-defective retroviral vectors harboring a nucleotide sequence of interest as part of the retroviral genome can be used. Such vectors have been described in detail. (Miller et al. (1990) *Mol. Cell. Biol.* 10:4239; Kolberg, R. (1992) *J. NIH Res.* 4:43; Cornetta et al. (1991) *Hum. Gene Therapy* 2:215).

Adenovirus and adeno-associated virus vectors useful in the invention may be produced according to methods already taught in the art. (See, e.g., Karlsson et al. (1986) EMBO 5:2377; Carter (1992) *Current Opinion in Biotechnology* 3:533-539; Muzcyzka (1992) *Current Top. Microbiol. Immunol.* 158:97-129; *Gene Targeting: A Practical Approach* (1992) ed. A. L. Joyner, Oxford University Press, NY). Several different approaches are feasible.

Alpha virus vectors, such as Venezuelan Equine Encephalitis (VEE) virus, Semliki Forest virus (SFV) and Sindbis virus vectors, can be used for efficient gene delivery. Replication-deficient vectors are available. Such vectors can be administered through any of a variety of means known in the art, such as, for example, intranasally or intratumorally. See Lundstrom, *Curr. Gene Ther.* 2001 1:19-29.

Additional literature describing viral vectors which could be used in the methods of the present invention include the following: Horwitz, M. S., *Adenoviridae and Their Replication*, in Fields, B., et al. (eds.) *Virology*, Vol. 2, Raven Press New York, pp. 1679-1721, 1990); Graham, F. et al., pp. 109-128 in *Methods in Molecular Biology*, Vol. 7: Gene *Transfer and Expression Protocols*, Murray, E. (ed.), Humana Press, Clifton, N.J. (1991); Miller, et al. (1995) *FASEB Journal* 9:190-199, Schreier (1994) *Pharmaceutica Acta Helvetiae* 68:145-159; Schneider and French (1993) *Circulation* 88:1937-1942; Curiel, et al. (1992) *Human Gene Therapy* 3:147-154; WO 95/00655; WO 95/16772; WO 95/23867; WO 94/26914; WO 95/02697 (Jan. 26, 1995); and WO 95/25071.

In some embodiments, the viral vector is derived from adenovirus (AV); adeno-associated virus (AAV; including AAV serotypes); retroviruses (e.g. lentiviruses (LV), Rhabdoviruses, murine leukemia virus); herpes virus, and the like. See, for example, Dornburg R (1995), *Gene Therap.* 2:301-310; Eglitis M A (1988), *Biotechniques* 6:608-614; Miller A D (1990), *Hum Gene Therap.* 1:5-14; and Anderson W F (1998), *Nature* 392:25-30, Forge et al., (2017) *Nature Biotechnology* 35, 280, the entire disclosures of which are herein incorporated by reference.

In some embodiments, the vector is an adeno-associated virus (AAV). In some embodiments, the viral vectors provided herein are AAV8 based viral vectors. In some embodiments, the AAV8 based viral vectors provided herein retain tropism for retinal cells. In some embodiments, the AAV-based vectors provided herein encode the AAV rep gene (required for replication) and/or the AAV cap gene (required for synthesis of the capsid proteins). Multiple AAV serotypes have been identified. In some embodiments, AAV-based vectors provided herein comprise components from one or more serotypes of AAV. In some embodiments, AAV based vectors provided herein comprise capsid components from one or more of AAV1. AAV2, AAV3, AAV4, AAV5, AAV6, AAV7, AAV8, AAV9, AAV10, AAV11, or AAVrh10. In some embodiments, AAV based vectors provided herein comprise components from one or more of AAV8, AAV9, AAV10, AAV11, or AAVrh10 serotypes. In some embodiments, the vector is selected from adeno-associated AAV serotype 2 (AAV-2), AAV8, and AAV2/8. In some embodiments, subjects can be tested to see if they have immunity to the viral capsid and possibly excluded if they do. Nucleic acid sequences of AAV based viral vectors and methods of making recombinant AAV and AAV capsids are taught, for example, in U.S. Pat. Nos. 7,282,199 B2, 7,790,449 B2, 8,318,480 B2, 8,962,332 B2 and International Patent Application No. PCT/EP2014/076466, each of which is incorporated herein by reference in its entirety.

In some embodiments, the AAV that is used in the methods described herein is Anc80 or Anc80L65, as described in Zinn et al., 2015, Cell Rep. 12 (6): 1056-1068, which is incorporated by reference in its entirety. In some embodiments, the AAV that is used in the methods described herein comprises one of the following amino acid insertions: LGETTRP (SEQ ID NO:56) or LALGETTRP (SEQ ID NO:57), as described in U.S. Pat. Nos. 9,193,956; 9,458, 517; and 9,587,282 and U.S. Patent Application Publication No. 2016/0376323, each of which is incorporated herein by reference in its entirety. In some embodiments, the AAV that is used in the methods described herein is AAV.7m8, as described in U.S. Pat. Nos. 9,193,956; 9,458,517; and 9,587.282 and U.S. Patent Application Publication No. 2016/0376323, each of which is incorporated herein by reference in its entirety. In some embodiments, the AAV that is used in the methods described herein is any AAV disclosed in U.S. Pat. No. 9,585,971, such as AAV-PHP.B.

In some embodiments, the AAV that is used in the methods described herein is an AAV disclosed in any of the following patents and patent applications, each of which is incorporated herein by reference in its entirety: U.S. Pat. Nos. 7,906,111; 8,524,446; 8,999,678; 8,628,966; 8,927, 514; 8,734,809; 9,284,357; 9,409,953; 9,169,299; 9,193, 956; 9,458,517; and 9,587,282 U.S. Patent Application Publication Nos. 2015/0374803; 2015/0126588; 2017/ 0067908; 2013/0224836; 2016/0215024; 2017/0051257; and International Patent Application Nos. PCT/US2015/ 034799 and PCT/EP2015/053335.

In some embodiments, a single-stranded AAV (ssAAV) may be used. In certain embodiments, a self-complementary vector, e.g., scAAV, may be used (see, e.g., Wu, 2007, *Human Gene Therapy*, 18 (2): 171-82, McCarty et al., 2001, *Gene Therapy*, Vol 8, Number 16, Pages 1248-1254; and U.S. Pat. Nos. 6,596,535; 7,125,717; and 7,456,683, each of which is incorporated herein by reference in its entirety).

In some embodiments, the viral vector is Anc80L65 serotype. Zinn et al. (2015) *Cell Reports* 12, 1056-1068. Further, Anc80L65-mediated gene transfer has shown much higher expression levels, as compared to established serotypes mentioned above, in retinal pigment epithelium (RPE), photoreceptor, liver, muscle, and hard to transduce cells such as inner ear hair cells. See, e.g., Landegger et al. (2017), *Nature Biotechnology* 35, 280.

In some embodiments, the invention provides a viral vector encoding CIB2 or a biologically active fragment or variant thereof. In some embodiments, the viral vector comprises a nucleic acid sequence encoding CIB2 or a biologically active fragment or variant thereof as provided herein.

In addition to the AAV gene delivery approaches described above, the skilled artisan will understand how to select an appropriate method for delivering nucleic acids encoding CIB2 or a biologically active fragment thereof to retina cells, such as RPE cells. See, for example, Bordet and Behar-Cohen, *Drug Discovery Today*, June 2019; Rodrigues et al., *Pharm Res* (2019), 36:29; Grishanin et al., *Mol. Ther.* (2018), 27 (1): 118-129; Trapani and Auricchio *Trends in Mol. Med.* (2018) 24 (8): 669-681; and Dalkara et al, *Sci. Translat. Med.* (2013), 5 (189): 189ra76.

In some embodiments, the nucleic acid comprises mRNA. See, e.g., Kaczmarek, et al., (2017). *Genome Medicine* 9, 60, for discussion of delivery of mRNA therapeutics to cells. In some embodiments, mRNA comprising CIB2 or a biologically active fragment or variant thereof can be delivered to specific organs or cell types such RPE or photoreceptors in the eye.

In some embodiments, increased levels or activity of CIB2 or a biologically active fragment or variant thereof can be achieved by a genomic editing approach. "Genomic editing" of an animal gene can be achieved, for example, by a single cleavage event, by cleavage followed by non-homologous end joining, by cleavage followed by homology-directed repair mechanisms, by cleavage followed by physical integration of a donor sequence, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) into the gene or its regulatory region, so as to disrupt the gene or regulatory region, or by targeting recombination of a splice acceptor sequence into an intron to cause mis-splicing of the transcript. See, U.S. Patent Publication Nos. 20030232410; 20050208489; 20050026157; 20050064474; 20060188987; 20060063231; and International Publication WO 07/014,275, the disclosures of which are incorporated by reference in their entireties for all purposes.

Recombinant transcription factors comprising the DNA binding domains from zinc finger proteins ("ZFPs") or TAL-effector domains ("TALEs") and engineered nucleases including zinc finger nucleases ("ZFNs"). TALENs, CRISPR/Cas nuclease systems, and homing endonucleases that are all designed to specifically bind to target DNA sites have the ability to regulate gene expression of endogenous genes and are useful in genome engineering and gene therapy. Sec, e.g., U.S. Pat. Nos. 9,045,763; 9,005,973; 8,956,828; 8,945,868; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983 and 20130177960 and 20150056705, the disclosures of which are incorporated by reference in their entireties for all purposes. Further, targeted nucleases are being developed based on the Argonaute system (e.g., from *T. thermophilus*, known as 'TtAgo', see Swarts et al. (2014) Nature 507 (7491): 258-261), which also may have the potential for uses in genome editing and gene therapy. Nuclease-mediated gene therapy can be used to genetically engineer a cell to have one or more inactivated genes and/or to cause that cell to express a product not previously being produced in that cell (e.g., via transgene insertion and/or via correction of an endogenous sequence). In particular, the use of engineered nucleases such as zinc finger nucleases (ZFNs), TALENS, TtAgo and CRISPR/Cas9 systems, provide the capability of precisely engineering specific genes. The nucleases act by creating double-stranded breaks (DSB) at a targeted DNA sequence, whose subsequent repair is then exploited to achieve one of three outcomes-gene knockout, gene mutation, or the site-specific addition (i.e. insertion or integration) of new genetic material (transgenes or fragments thereof) at the locus. For example, if DSB repair occurs through the error-prone NHEJ pathway, the result can be small insertions and/or deletions of nucleotides at the break site that thereby disrupt an open-reading frame.

In some embodiments, CIB2, a biologically active fragment or variant thereof is inserted by either homology directed repair (HDR) or by end capture during non-homologous end joining (NHEJ) driven processes. See, e.g., U.S. Pat. Nos. 9,045,763; 9,005,973; 7,888,121 and 8,703, 489.

In some embodiments, the genomic editing is performed using a nuclease, which can include CRISPR associated proteins (Cas proteins, e.g., Cas9), Zinc finger nuclease (ZFN), Transcription Activator-Like Effector Nuclease (TALEN), and meganucleases. Nucleases can be naturally existing nucleases, genetically modified, and/or recombinant. Gene editing can also be performed using a transposon-based system (e.g. PiggyBac, Sleeping beauty). For example, gene editing can be performed using a transposase.

In some embodiments, CIB2, a biologically active fragment or variant thereof is knocked-in using a CRISPR/Cas system of genomic editing at a particular locus in the genome. In some embodiments of the disclosure, one or more targeted "nucleases," e.g. CRIPSR/Cas9, TALEN or ZFN, as described herein create a double-stranded break in the target sequence (e.g., cellular chromatin) at a predetermined locus. A "target site" or "target sequence" is a nucleic acid sequence that defines a general region of a nucleic acid to which a binding molecule may bind, provided sufficient conditions for binding exist.

In some embodiments, the CIB2 promoter is activated using a genomic editing approach, e.g., using a CRISPR/Cas system. In some embodiments, the promoter can be activated using catalytically dead (d)Cas 9/CRISPR-mediated promoter target engagement resulting in subsequent upregulation of CIB2. See, e.g., Kaczmarek, et al., (2017).

In some embodiments, levels of CIB2 or a biologically active fragment or variant thereof are increased by administering a composition comprising a polypeptide. See, e.g., Lagassé et al. (2017). F1000Research 6, 113. In some embodiments, recombinant CIB2 or a biologically active fragment or variant thereof can be administered to whole body or to specific organs/tissues.

In some embodiments, the polypeptide composition comprises an agent that facilitates uptake of the polypeptide into cells. In some embodiments, the agent comprises one or more cationic peptides, amphipathic molecules, lipid-based carriers or combinations thereof.

In some embodiments, the amino acid sequence of CIB2 comprises SEQ ID NO: 1. In some embodiments, the polypeptide comprises a biologically active fragment or variant of CIB2. In some embodiments, the biologically active fragments or variants of CIB2 have at least 90% identity to SEQ ID NO:1. In some embodiments, the CIB2 or a biologically active fragment or variant thereof has at least 91%, 92%, 93%, 94%, 95%, 96%, 97%, 98% or 99% identity to the polypeptide of SEQ ID NO:1.

In some embodiments, the polypeptide comprises a biologically active fragment of CIB2. A fragment is a polypeptide having an amino acid sequence that entirely is the same as part but not all of the amino acid sequence of the aforementioned CIB2 polypeptide. In some embodiments, a fragment may constitute at least about 150 contiguous amino acids identified in SEQ ID NO:1. In some embodiments, the fragment is at least about 30, 35, 40, 45, 50, 55, 60, 65, 70, 75, 80, 85, 90, 95, 100, 105, 110, 115, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150 contiguous amino acids identified in SEQ ID NO: 1.

In some embodiments the fragments include, for example, truncation polypeptides having the amino acid sequence of CIB2, except for deletion of a continuous series of residues that includes the amino terminus, or a continuous series of residues that includes the carboxyl terminus or deletion of two continuous series of residues, one including the amino terminus and one including the carboxyl terminus. In some embodiments, fragments are characterized by structural or functional attributes such as fragments that comprise alpha-helix and alpha-helix forming regions, beta-sheet and beta-sheet-forming regions. turn and turn-forming regions, coil and coil-forming regions, hydrophilic regions, hydrophobic regions, alpha amphipathic regions, beta amphipathic regions, flexible regions, surface-forming regions, substrate binding region, high antigenic index regions, or functional domains. Biologically active fragments are those that mediate protein activity, including those with a similar activity or an improved activity, or with a decreased undesirable activity. In some embodiments, the activity is the ability to bind to Rheb protein in its GDP-bound state.

In one embodiment, the fragment comprises the final 30, 35, 40, 45, 50, 55, 60, 65, 70, 75, 80, 85, 90, 95, 100, 105, 110, 115, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150 amino acids of CIB2 of SEQ ID NO:1.

In one embodiment, the fragment comprises the first 30, 35, 40, 45, 50, 55, 60, 65, 70, 75, 80, 85, 90, 95, 100, 105, 110, 115, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150 amino acids of CIB2 of SEQ ID NO:1.

Biologically active fragments or variants of CIB2 include polypeptides having an amino acid sequence at least 90% identical to that of SEQ ID NO:1 or fragments thereof with at least 90% identity to the corresponding fragment of SEQ ID NO:1, all of which retain the biological activity of CIB2. Included in this group are variants of the defined sequence and fragment. In some embodiments, the variants are those that vary from the reference by conservative amino acid substitutions, i.e., those that substitute a residue with another of like characteristics. Typical substitutions are among Ala, Val, Leu and Ile; among Ser and Thr; among the acidic residues Asp and Glu; among Asn and Gln; and among the basic residues Lys and Arg, or aromatic residues Phe and Tyr. In some embodiments, the polypeptides are variants in which 1, 2, 3, 4, 5, 6, 7, 8, 9, 10 or more amino acids are substituted, deleted, or added in any combination.

The polypeptides comprising CIB2 and biologically active fragments or variants thereof can be prepared in any suitable manner. Such polypeptides include recombinantly produced polypeptides, synthetically produced polypeptides, or polypeptides produced by a combination of these methods. Means for preparing such polypeptides are well understood in the art.

In some embodiments, the polypeptide is associated with a protein transduction domain. In some embodiments, the polypeptide is a fusion protein comprising a protein transduction domain to facilitate uptake of the encoded polypeptide by cells, thereby facilitating the polypeptide's therapeutic activity when administered to a subject. In some embodiments, the invention provides a fusion protein comprising i) CIB2 or a biologically active fragment or variant thereof; and ii) a protein transduction domain.

In some embodiments, the polypeptide further comprises one or more epitope tags and/or purification tags. The epitope tag is not limiting and can include a Myc tag, a FLAG tag, a hemagglutinin (HA) tag, a V5 tag, and/or combinations thereof. The purification tag is not limiting and can include a histidine tag (6×), a glutathione S-Transferase tag or a combination thereof.

In some embodiments, the polypeptide comprises an enzymatic cleavage site to further aid in purification and processing of the protein. In some embodiments, the cleavage site is an enterokinase cleavage site.

In some embodiments, the polypeptide comprises a histidine tag (6×), a FLAG tag, a hemagglutinin (HA) tag, and/or an enterokinase cleavage site.

The PTD sequence is not limiting, provided it encodes a peptide sequence that enhances uptake of a functional polypeptide by cells. In some embodiments, the PTD comprises RRRRRRRRRPSASYPYDVPDYA (SEQ ID NO:5). In some embodiments, the PTD comprises one or more variants of TAT protein from HIV selected from GRKKRRQRRR (SEQ ID NO:6), YGRKKRRQRRR (SEQ ID NO:7), or GRKKRRQ (SEQ ID NO:8). Alternate forms of TAT can also be used. Non-limiting examples of PTDs which can be used in the present invention are shown in Table 1.

TABLE 1

Protein Transduction Domain Sequences
PROTEIN TRANSDUCTION DOMAINS

RRRRRRRRRPSASYPYDVPDYA (SEQ ID NO: 5)

GRKKRRQRRR (SEQ ID NO: 6)

YGRKKRRQRRR (SEQ ID NO: 7)

GRKKRRQ (SEQ ID NO: 8)

TABLE 1-continued

Protein Transduction Domain Sequences
PROTEIN TRANSDUCTION DOMAINS

RQIKIWFQNRRMKWKK (SEQ ID NO: 9)

RRMKWKK (SEQ ID NO: 10)

RRWRRWWRRWWRRWRR (SEQ ID NO: 11)

RGGRLSYSRRRFSTSTGR (SEQ ID NO: 12)

RKKRRQRRR (SEQ ID NO: 13)

YARAAARQARA (SEQ ID NO: 14)

RRRRRRRR (SEQ ID NO: 15)

KKKKKKKK (SEQ ID NO: 16)

GWTLNSAGYLLGKINLKALAALAKXIL (SEQ ID NO: 17)

SRRHHCRSKAKRSRHH (SEQ ID NO: 18)

NRARRNRRRVR (SEQ ID NO: 19)

RQLRIAGRRLRGRSR (SEQ ID NO: 20)

KLIKGRTPIKFGK (SEQ ID NO: 21)

RRIPNRRPRR (SEQ ID NO: 22)

KLALKLALKALKAALKLA (SEQ ID NO: 23)

KLAKLAKKLAKLAK (SEQ ID NO: 24)

GALFLGFLGAAGSTNGAWSQPKKKRKV (SEQ ID NO: 25)

KETWWETWWTEWSQPKKKRKV (SEQ ID NO: 26)

LKKLLKKLLKKLLKKLLKKL (SEQ ID NO: 27)

QAATATRGRSAASRPTERPRAPARSASRPRRPVE
(SEQ ID NO: 28)

MGLGLHLLVLAAALQGAKSKRKV (SEQ ID NO: 29)

AAVALLPAVLLALLAPAAANYKKPKL (SEQ ID NO: 30)

MANLGYWLLALFVTMWTDVGLCKKRPKP (SEQ ID NO: 31)

LGTYTQDFNKFHTFPQTAIGVGAP (SEQ ID NO: 32)

DPKGDPKGVTVTVTVTVTGKGDPXPD (SEQ ID NO: 33)

PPPPPPPPPPPPPPPP (SEQ ID NO: 34)

VRLPPPVRLPPPVRLPPP (SEQ ID NO: 35)

PRPLPPPRPG (SEQ ID NO: 36)

SVRRRPRPPYLPRPRPPPFFPPRLPPRIPP (SEQ ID NO: 37)

TRSSRAGLQFPVGRVHRLLRK (SEQ ID NO: 38)

GIGKFLHSAKKFGKAFVGEIMNS (SEQ ID NO: 39)

KWKLFKKIEKVGQNIRDGIIKAGPAVAVVGQATQIAK
(SEQ ID NO: 40)

ALWMTLLKKVLKAAAKAALNAVLVGANA (SEQ ID NO: 41)

GIGAVLKVLTTGLPALISWIKRKRQQ (SEQ ID NO:42)

INLKALAALAKKIL (SEQ ID NO:43)

GFFALIPKIISSPLPKTLLSAVGSALGGSGGQE
(SEQ ID NO: 44)

TABLE 1-continued

Protein Transduction Domain Sequences
PROTEIN TRANSDUCTION DOMAINS

LAKWALKQGFAKLKS (SEQ ID NO:45)

SMAQDIISTIGDLVKWIIQTVNXFTKK (SEQ ID NO:46)

LLGDFFRKSKEKIGKEFKRIVQRIKQRIKDFLANLVPRTES
(SEQ ID NO:47)

PAWRKAFRWAWRMLKKAA (SEQ ID NO:48)

KLKLKLKLKLKLKLKLKL (SEQ ID NO:49)

LLILLRRRIRKQANAHSK (SEQ ID NO:50)

GALFLGWLGAAGSTMGAKKKRKV (SEQ ID NO:51)

In some embodiments, a linker may be used to connect one or more PTDs and CIB2 or a biologically active fragment or variant thereof. In some embodiments, the PTD is fused or linked in frame to the N-terminal and/or C-terminal end of any one of the CIB2 full-length, or biologically active fragments or variants thereof described throughout the disclosure. In some embodiments, the CIB2 sequences are located downstream from the PTD sequence, i.e., the PTD sequence is N-terminal to the CIB2 sequence.

The administration of the one or more compositions increase the levels or activity of CIB2 or a biologically active fragment or variant thereof in cells of the subject. In some embodiments, the levels or activity increase by about 10%, about 20%, about 30%, about 40%, about 50%, about 60%, about 70%, about 80%, about 90%, about 100%, about 200%, about 300%, about 400%, or about 500% or more over untreated levels.

In some embodiments, the subject is co-administered one or more additional therapeutic agents. In some embodiments, the additional agent is an mTORC1 inhibitor or other therapeutic or treatment. See, e.g., U.S. Pat. No. 9,669,032, which is incorporated herein by reference.

The terms "co-administered," "administered in combination with," and their grammatical equivalents, encompass administration of two or more agents to a subject so that both agents and/or their metabolites are present in the animal at the same time. Co-administration includes simultaneous administration in separate compositions, administration at different times in separate compositions, or administration in a composition in which both agents are present. Co-administered agents may be in the same formulation. Co-administered agents may also be in different formulations.

In some embodiments, the disease, condition, or disorder is age-related macular degeneration (e.g., dry and/or wet), macular degeneration, Stargardt disease, or other degenerative disease/disorder of the eye. In some embodiments, the subject is administered an effective amount of a retinoid such as 9-cis retinal or derivative thereof in combination with the one or more compositions of the invention (Palczewski 2010; PMID: 20435355). In the case of wet macular degeneration it might be desirable to combine CIB2 therapy with an anti-angiogenic therapy, for example, an anti-VEGF therapy as is known in the art.

In some embodiments, the CIB2 therapy described herein is administered in combination with another therapeutic agent. For example, to treat wet macular degeneration, one or more CIB2 therapies as described herein can be combined with anti-angiogenic therapy, for example, by administering the CIB2 therapy along with a therapy that inhibits neovascularization in the eye. Such anti-angiogenic therapies used to treat wet AMD include, but are not limited to, inhibitors of vascular endothelial cell growth factor (VEGF) such as bevacizumab (e.g., Avastin®), ranibizumab (e.g., Lucentis®), and aflibercept (e.g., Eylea®), as well as nucleic acids encoding such therapeutic polypeptides (see, e.g., Grishanin et al., *Mol. Ther.* (2019), 27 (1): 118-129).

In some embodiments, the one or more additional therapeutic agents are those used to treat cancer. In some embodiments, the subject is administered one or more anti-cancer agents and/or radiotherapy in combination with the one or more compositions of the invention. The anti-cancer agent is not limiting. In some embodiments, the anti-cancer agent is selected from the group consisting of Abiraterone Acetate, Abitrexate (Methotrexate), Abraxane (Paclitaxel Albumin-stabilized Nanoparticle Formulation), ABVD, ABVE, ABVE-PC. AC. AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Becenum (Carmustine), Belcodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPOX, Carboplatin, CARBOPLATIN-TAXOL, Carfilzomib, Carmubris (Carmustinc), Carmustine, Carmustine Implant, Casodex (Bicalutamide), CecNU (Lomustine) Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine$^{131}$ Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C. Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nivolumab, Nolvadex (Tamoxifen Citrate), Nplate (Romiplostim), Obinutuzumab, OEPA, Ofatumumab, OFF, Olaparib, Omacetaxine Mepesuccinate, Oncaspar (Pegaspargase), Ontak (Denilcukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sorafenib Tosylate, Sprycel (Dasatinib), STANFORD V. Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and I 131 Iodine Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate).

In some embodiments, the subject is not administered another therapeutic agent and is administered a composition consisting of or consisting essentially of the one or more compositions of the invention.

Also provided are methods for predicting and/or evaluating a response to treatment with one or more compositions by assessing one or more effects associated with increasing activity or levels of CIB2. Such effects can include, e.g., increased canonical and/or non-canonical autophagy and/or increased phagolysosomal digestion in cells.

In some embodiments, autophagy and/or increased phagolysosomal digestion in cells in a subject may be assessed, and based on the level detected, a decision may be made to treat (or to continue or discontinue treatment) with one or more compositions of the invention, or to employ an alternate treatment.

In some embodiments, detection or measurement of autophagy and/or increased phagolysosomal digestion is performed as compared to controls, which may include, but are not limited to, a comparison with data from normal subjects and/or comparable normal tissue (in the same or different subjects) absent the disease or disorder present in the subject (or the specific tissue of the subject tested). In some embodiments, the comparison may be between levels detected at a variety of time intervals (and/or locations) in a subject. In some embodiments, the detection needs to be statistically significant as compared to background or control levels; the ability to assess significance is well-known in the art.

In another embodiment, the invention provides methods of screening for agents that increase activity or levels of CIB2 or biologically active fragments or variants thereof. In some embodiments, methods of screening for biologically active fragments (including, but not limited to truncations) or variants of CIB2 are contemplated. In some embodiments, activity can be assayed using one of the methods described herein, including detecting binding of the fragments or variants of CIB2 with Rheb, particularly Rheb in the GDP-bound state.

Nucleic Acids

In some embodiments, the invention provides a nucleic acid molecule encoding CIB2 or a biologically active fragment or variant thereof.

In some embodiments, the invention provides a nucleic acid molecule encoding a fusion protein comprising i) a nucleotide sequence encoding CIB2 or a biologically active fragment or variant thereof; and ii) a nucleotide sequence encoding a protein transduction domain.

In some embodiments, a nucleotide sequence encoding CIB2 or a biologically active fragment or variant thereof may be derived from genomic DNA, i.e., cloned directly from the genome of a particular organism. In some embodiments, however, the nucleic acid would comprise complementary DNA (cDNA). The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression.

The organismal source of CIB2 is not limiting. In some embodiments, the CIB2 nucleic acid sequence is derived from a mammal, bird, reptile or fish. In some embodiments, the CIB2 is of human origin. In some embodiments, the CIB2 is from dog, cat, horse, mouse, rat, guinea pig, sheep, cow, pig, monkey, or ape.

The nucleic acid molecules may be produced using recombinant DNA technology (e.g., polymerase chain reaction (PCR) amplification, cloning) or chemical synthesis. CIB2 nucleic acids include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect (e.g., production of CIB2 protein in non-human expression systems).

In some embodiments, the coding sequence of CIB2 is encoded by SEQ ID NO:3 and 4. "CIB2" nucleic acid in accordance with the invention may contain a variety of different bases compared to the wild-type sequence and yet still encode a corresponding polypeptide that exhibits the biological activity of the native CIB2 polypeptide.

In some embodiments, a particular nucleotide sequence encoding CIB2 polypeptide may be identical over its entire length to the coding sequence in SEQ ID NO:3 and 4. In some embodiments, a particular nucleotide sequence encoding CIB2 polypeptide may be an alternate form of SEQ ID NO:3 and 4 due to degeneracy in the genetic code or variation in codon usage encoding the polypeptide of SEQ ID NO:3 and 4.

In some embodiments, the nucleic acid sequence of CIB2 comprises a nucleotide sequence that is highly identical, at least 90% identical, with a nucleotide sequence encoding CIB2 polypeptide. In some embodiments, the nucleic acid sequence of CIB2 comprises a nucleotide sequence that is at least 60%, 65%, 70%, 75%, 80%, 85%, 90%, 91%, 92%, 93%, 94%, 95%, 96%, 97%, 98% 99% or 100% identical with the encoding nucleotide sequence set forth in SEQ ID NO:3 and 4.

When a polynucleotide of the invention is used for the recombinant production of CIB2 polypeptide, the polynucleotide may include the coding sequence for the full-length polypeptide or a fragment thereof, by itself; the coding sequence for the full-length polypeptide or fragment in reading frame with other coding sequences, such as those encoding a leader or secretory sequence, a pre-, or pro or prepro-protein sequence, or other fusion peptide portions. The polynucleotide may also contain non-coding 5' and 3' sequences, such as transcribed, non-translated sequences, splicing and polyadenylation signals, ribosome binding sites and sequences that stabilize mRNA.

In some embodiments, the nucleotide sequence encoding CIB2 or a biologically active fragment or variant thereof includes nucleic acid molecules comprising a polynucleotide having a nucleotide sequence at least 90%, 91%, 92%, 93%, 94%, 95%, 96%, 97%, 98% 99% or 100% identical to (a) a nucleotide sequence encoding CIB2 having the amino acid sequence in SEQ ID NO:1 and 2; or (b) a nucleotide sequence complementary to the nucleotide sequences in (a).

Conventional means utilizing known computer programs such as the BestFit program (Wisconsin Sequence Analysis Package, Version 10 for Unix, Genetics Computer Group, University Research Park, 575 Science Drive, Madison, Wis. 53711) may be utilized to determine if a particular nucleic acid molecule is at least 90%, 91%, 92%, 93%, 94%, 95%, 96%, 97%, 98% or 99% identical to SEQ ID NO:3 and 4.

In some embodiments, the nucleotide sequence encoding CIB2 or a biologically active fragment or variant thereof encode an amino acid sequence of CIB2 of SEQ ID NO:1 and 2, in which 1, 2, 3, 4, 5, 6, 7, 8, 9, 10 or more amino acid residues are substituted, deleted or added, in any combination.

In some embodiments, the nucleotide sequences are at least 90% identical over their entire length to a polynucleotide encoding a CIB2 having the amino acid sequence set out in SEQ ID NO:1 and 2, and polynucleotides which are complementary to such polynucleotides. In some embodiments, the polynucleotides are at least 91%, 92%, 93%, 94%, 95%, 96%, 97%, 98%, or at least 99% identical.

In some embodiments, the nucleic acid molecule encodes a biologically active fragment of CIB2 protein. In some embodiments, the biologically active fragment can be at least about 201, 210, 222, 231, 240, 252, 261, 270, 282, 291, 300, 312, 321, 330, 342, 351, 360, 372, 381, 390, 402, 405, 408, 411, 414, 417, 420, 423, 426, or 429 nucleotides in length.

In some embodiments, the nucleic acids encoding CIB2, a biologically active fragment or variant thereof, are fused to a nucleic acid sequence encoding a protein transduction domain (PTD). PTDs are short modular motifs, which, when attached to heterologous proteins, can transfer proteins across cell membranes. These short motifs, generally rich in positively charged amino acids, permit transfer of proteins across plasma membrane, without requiring any receptors for their internalization. Viral and cellular proteins-such as the HIV-TAT, herpes simplex viral VP22, the homeodomain protein antennapedia, lactoferrin and fibroblast growth factor contain such domains, which can be modularly attached to other proteins. PTDs are also called cell delivery domain or cell transduction domains.

In some embodiments, the nucleic acid sequence encoding the PTD is selected from:

```
                                    (SEQ ID NO: 52)
AGACGAAGGCGCAGACGGAGGCGTAGACCGTCTGCCAGCTATCCATACG
ACGTGCCTGACTACGCG, (SEQ ID NO: 53)
GGCCGTAAAAAACGCCGTCAACGCCGCCGT, (SEQ ID NO: 54)
TATGGCCGTAAAAAACGCCGTCAACGCCGCCGT and (SEQ ID NO: 55)
GGCCGTAAAAAACGCCGTCAA.
```

In some embodiments, the CIB2 nucleic acid sequence has been optimized for expression in alternative host organisms (e.g., non-human). Although as described above, the genetic code is degenerate, so frequently one amino acid may be coded for by two or more nucleotide codons. Thus, multiple nucleic acid sequences may encode one amino acid sequence. Although this creates identical proteins, the nucleic acids themselves are distinct, and can have other distinct properties. As described herein, one aspect of the choice of codon usage can be (but is not limited to) the ability to express a protein in a non-native cells (e.g., a human protein in bacteria, r yeast, or insect cells), or the level of expression in such cells. In order to obtain enough protein for purification, testing, and use in in vitro assays, in animal models, and eventually in clinical development, efficient protein expression in non-human systems is needed.

In some embodiments, the nucleic acid sequence further includes a nucleotide sequence encoding one or more of an epitope tag or a purification tag.

The term "epitope tag" as used herein in reference to nucleic acid molecules refers to nucleotides encoding peptide sequences that are recognized and bound by the variable region of an antibody or fragment. In some embodiments, the epitope tag is not part of the native protein. In some embodiments, the epitope tag is removable. In some embodiments, the epitope tag is not intrinsic to the protein's native biological activity. Examples of epitope tags include, but are not limited to Myc, HA, GFP, tdTomato, and FLAG, V5, or combination thereof.

The term "purification tag" as used herein in reference to nucleic acid molecules refers to nucleotides encoding peptide sequences that facilitate the purification of the protein, but are generally not necessary for the protein's biological activity. In some embodiments, purification tags may be removed following protein purification. Examples of purification tags include, but are not limited to glutathione S-transferase (GST) or 6×-histidine (H6).

In some embodiments, the epitope tag is selected from Myc, HA, and FLAG and combinations thereof. In some embodiments, the purification tag is one or more of glutathione-S-transferase (GST) or 6×-histidine (H6).

In some embodiments, the nucleic acid also encodes a cleavage site for a protease. In some embodiments, the cleavage site is an enterokinase target sequence, located downstream from one or more epitope and/or purification tags.

Vectors, Host Cells, and Recombinant Expression

The present invention also relates to vectors that comprise the nucleic acids of the present invention, including cloning vectors and expression vectors, host cells which are genetically engineered with vectors of the invention and methods for the production of polypeptides of the invention by recombinant techniques. Cell-free translation systems can also be employed to produce such proteins using RNAs derived from the DNA constructs of the invention.

Representative examples of appropriate hosts include bacterial cells, such as streptococci, staphylococci, *Escherichia coli, Streptomyces* and *Bacillus subtilis*; fungal cells, such as yeast and *Aspergillus*; insect cells such as *Drosophila* S2 and *Spodoptera* Sf9; mammalian cells such as CHO, COS-7, HeLa, C127, 3T3, BHK, HEK-293, RPE-J, MEF and Bowes melanoma. A great variety of expression systems can be used, including DNA or RNA vectors.

In other embodiments, this invention provides an isolated nucleic acid molecule of the invention operably linked to a heterologous promoter. The invention further provides an isolated nucleic acid molecule operably linked to a heterologous promoter, wherein said isolated nucleic acid molecule is capable of expressing a protein comprising CIB2, or a biologically active fragment or variant thereof when used to transform an appropriate host cell.

Methods for the production of polypeptides of the invention including culturing a host cells transfected with one or more of the vectors of the present invention under conditions promoting expression of the polypeptide encoded by the vector, and isolating the polypeptide so expressed from the cell culture.

Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC 2.0 from INVITROGEN and BACPACK baculovirus expression system from CLONTECH.

Other examples of expression systems include COMPLETE CONTROL Inducible Mammalian Expression System from STRATAGENE, which involves a synthetic ecdysone-inducible receptor, or its pET Expression System, an *E. coli* expression system. Another example of an inducible expression system is available from INVITROGEN, which carries the T-REX (tetracycline-regulated expression) System, an inducible mammalian expression system that uses the full-length CMV promoter. INVITROGEN also provides a yeast expression system called the *Pichia methanolica* Expression System, which is designed for high-level production of recombinant proteins in the methylotrophic yeast *P. methanolica*. One of skill in the art would know how to manipulate a vector, such as an expression construct, to produce a nucleic acid sequence or its cognate polypeptide, protein, or peptide.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented.

One embodiment involves the use of gene transfer to immortalize cells for the production of proteins. The nucleic acid for the protein of interest may be transferred as described above into appropriate host cells followed by culture of cells under the appropriate conditions.

Examples of useful mammalian host cell lines are Vero and HeLa cells and cell lines of Chinese hamster ovary, W138, BHK, COS-7, HEK-293, HepG2, NIH3T3, RIN, RPE-J, MEF (control or specific gene knockout) and MDCK cells. In addition, a host cell clone may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside G418; and hygro, that confers resistance to hygromycin.

As used herein, the terms "cell," "cell line," and "cell culture" may be used interchangeably. All of these terms also include their progeny, which are any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes (e.g., bacteria or yeast), depending upon whether the desired result is replication of the vector or expression of part or all of the vector-encoded nucleic acid sequences. Numerous cell lines and cultures are available for use as a host cell, and they can be obtained through the American Type Culture Collection (ATCC). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KCB, as well as a number of commercially available bacterial hosts such as SURE Competent Cells and SOLOPACK Gold Cells (STRATAGENE, La Jolla). Alternatively, bacterial cells such as E. coli LE392 could be used as host cells for phage viruses.

Examples of eukaryotic host cells for replication and/or expression of a vector include HeLa, NIH3T3, Jurkat, HEK-293, COS-7, MEF, CHO, Saos, RPE-J, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Pharmaceutical Compositions

Where clinical applications are contemplated, it will be necessary to prepare pharmaceutical compositions in a form appropriate for the intended application. Generally, this will entail preparing compositions that are suitable for administration to a subject, e.g., essentially free of pyrogens, as well as other impurities that could be harmful to humans or animals.

In some embodiments, the invention provides a pharmaceutical composition comprising CIB2 or a biologically active fragment or variant thereof as described herein.

In some embodiments, the invention provides a pharmaceutical composition comprising a nucleic acid encoding CIB2 or a biologically active fragment or variant thereof as described herein.

In some embodiments, the invention provides a pharmaceutical composition comprising a viral vector encoding CIB2 or a biologically active fragment or variant thereof as described herein.

In some embodiments, the compositions are pharmaceutical compositions comprising effective amounts of proteins or nucleic acids which are capable of treating one or more diseases or conditions described herein.

In some embodiments, the composition comprises appropriate salts and/or buffers to render delivery vectors or proteins stable and allow for uptake by target cells. In some embodiments, compositions comprising a viral vector or protein is dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" can include solvents, dispersion media, coatings, antibacterial and antifungal agents, isotonic and absorption delaying agents and the like. Except insofar as any conventional media or agent is incompatible with the nucleic acids or proteins of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes of administration may include oral, parenteral (including intravenous, intramuscular, subcutaneous, intradermal, intra-articular, intra-synovial, intrathecal, intra-arterial, intracardiac, subcutaneous, intraorbital, intracapsular, intraspinal, intrasternal, and transdermal), nasal, buccal, urethral, rectal, vaginal, mucosal, dermal, or topical (including dermal, buccal, and sublingual). Alternatively, administration may be by orthotopic, intradermal, subcutaneous, intramuscular, intraperitoneal or intravenous injection. Such compositions would normally be administered as pharmaceutically acceptable compositions. Of particular interest is direct intratumoral administration, perfusion of a tumor, or administration local or regional to a tumor, for example, in the local or regional vasculature or lymphatic system, or in a resected tumor bed. Administration can also be via nasal spray, surgical implant, internal surgical paint, infusion pump, or via catheter, stent, balloon or other delivery device. The most useful and/or beneficial mode of administration can vary, especially depending upon the condition of the recipient and the disorder being treated.

In some embodiments, suitable delivery reagents for administration in conjunction with the present nucleic acids, vectors or polypeptides can include the Mirus Transit TKO lipophilic reagent; lipofectin; lipofectamine; cellfectin; or polycations (e.g., polylysine), or liposomes. In some embodiments, a particular delivery reagent comprises a liposome.

In some embodiments, liposomes can aid in the delivery of the present nucleic acids or vectors to a particular tissue, and can also increase the blood half-life of the nucleic acids. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are herein incorporated by reference.

In certain aspects, the liposomes encapsulating the present nucleic acids comprise a ligand molecule that can target the liposome to a particular cell or tissue at or near the site of interest. Ligands that bind to receptors prevalent in the tissues to be targeted, such as monoclonal antibodies that bind to surface antigens, are contemplated. In particular cases, the liposomes are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand. Opsonization-inhibiting moieties for use in preparing the liposomes of the disclosure are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Opsonization inhibiting moieties suitable for modifying liposomes are preferably water-soluble polymers with a number-average molecular weight from about 500 to about 40,000 Daltons, and more preferably from about 2,000 to about 20,000 Daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

In some embodiments the opsonization-inhibiting moiety is a PEG, PPG, or derivatives thereof. Liposomes modified with PEG or PEG-derivatives are sometimes called "PEGylated liposomes." The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture such as tetrahydrofuran and water in a 30:12 ratio at 60 degrees C.

Recombinant plasmids can also be administered directly or in conjunction with a suitable delivery reagent, including but not limited to the Mirus Transit LT 1 lipophilic reagent; lipofectin; lipofectamine; cellfectin; polycations (e.g., polylysine) or liposomes.

The nucleic acids for increasing the level of CIB2 or a biologically active fragment or variant thereof can be administered to the subject by any suitable means. For example, the nucleic acids can be administered by gene gun, electroporation, or by other suitable parenteral or enteral administration routes, or by injection, for example, by intramuscular or intravenous injection.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intratumoral injection, intra-retinal injection or subretinal injection or intravitreal injection); subcutaneous injection or deposition including subcutaneous infusion (such as by osmotic pumps); direct (e.g., topical) application to the area at or near the site of interest, for example by a catheter or other placement device (e.g., a corneal pellet or a suppository, eye-dropper, or an implant comprising a porous, non-porous, or gelatinous material); and inhalation. In a particular embodiment, injections or infusions of the composition(s) are given at or near the site of disease.

The nucleic acids for increasing the level of CIB2 or a biologically active fragment or variant thereof of the invention can be administered in a single dose or in multiple doses. Where the administration of a composition is by infusion, the infusion can be a single sustained dose or can be delivered by multiple infusions. Injection of the agent directly into the tissue is at or near the site of need. Multiple injections of the agent into the tissue at or near the site of interest are encompassed within this disclosure.

One skilled in the art can also readily determine an appropriate dosage regimen for administering the nucleic acids for increasing the level of CIB2 or a biologically active fragment or variant thereof of the invention to a given subject. For example, the composition(s) can be administered to the subject once, such as by a single injection or deposition at or near the site of interest. In some embodiments, the composition(s) can be administered to a subject once or twice daily to a subject once weekly for a period of from about three to about twenty-eight days, in some embodiments, from about seven to about ten weeks. In some dosage regimens, the composition(s) is injected at or near the site of interest once a day for seven days. Where a dosage regimen comprises multiple administrations, it is understood that the effective amount of composition(s) administered to the subject can comprise the total amount of composition(s) administered over the entire dosage regimen.

A dosing schedule may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art. In some embodiments, the therapeutic agent is administered in a dose of between about 0.001 mg/kg to about 100 mg/kg body weight. In some embodiments, the dose administered is about 0.01-50 mg/kg body weight of the subject. In some embodiments, the dose administered is about 0.5-5 mg/kg body weight of the subject. In some embodiments, the dose administered is about 1 mg/kg body weight of the subject.

Application of the teachings of the present invention to a specific problem is within the capabilities of one having ordinary skill in the art in light of the teaching contained herein. Examples of the compositions and methods of the invention appear in the following non-limiting Examples.

EXAMPLES

Example 1. CIB2 Regulates mTORC1 Signaling and is Essential for Autophagy and Visual Function Autophagy is essential for maintenance and function of retinal pigment epithelium (RPE) (Valapala et al., Autophagy 10, 480-496 (2014); Kim et al., Cell 154, 365-376 (2013)). Although molecular mechanisms remain elusive, deficits in autophagy have been associated with age-related pathology in mice and macular degeneration (AMD) in humans (Golestaneh et al., Disease 8, e2537 (2017); Mitter et al., Advances in experimental medicine and biology 723, 83-90 (2012)). Here we show that deficiency of calcium and integrin-binding protein 2 (CIB2) specifically within murine RPE causes age related pathophysiology, including RPE vacuolization, lipid accumulation, and attenuated electroretinogram amplitudes, which can be rescued using exogenous retinoids. Further, mice with ubiquitous or RPE-specific loss of Cib2 displayed reduced autophagy flux, and increased mTORC1 signaling—a negative regulator of autophagy. Concordant molecular deficits were found in RPE/choroid tissues from humans affected with dry AMD. Mechanistically, we found that CIB2 negatively regulates mTORC1 signaling by preferentially binding to GDP-loaded Rheb, and Raptor. Upregulated mTORC1 signaling is also implicated in diverse disorders, including Tuberous sclerosis complex (TSC), and lymphangioleiomyomatosis (LAM). Over-expressing CIB2 in LAM patient-derived cells and Tsc2 knockout cell line down-regulated mTORC1 signaling. Thus, besides fundamental cell biology relevance our findings have significant ramifications for the etiology of AMD and other mTORC1 hyperactivity disorders and their treatment.

The retinal pigment epithelium (RPE) is a single-layer of polarized cobblestone-shaped epithelium, the apical microvilli of which intimately contact the photoreceptor (PR) outer segments (OS). The RPE has multiple functions essential to normal vision such as absorbing excess light, regenerating vitamin A-derived chromophores during the visual cycle, and shuttling nutrients to the PR and metabolites out of the sub-retinal space. It also plays an integral role in PR survival by engulfing the shed OS discs and subsequent clearance via LC3-associated phagocytosis (LAP) (Strauss et al., Physiological Reviews 85, 845-881 (2005)). Likewise, macroautophagy (henceforth autophagy) is a catabolic process which removes cellular debris, damaged and aged organelles, and shares many features with LAP. Autophagy is an essential process for all cells, but particularly in post-mitotic cells such as RPE (Kim et al., Cell 154, 365-376 (2013)) which have the highest life-long phagocytic load of any cell-type in the body.

CIB2 belongs to a family of proteins that includes four members (CIB1-CIB4). CIB proteins contain $Ca^{2+}/Mg^{2+}$ binding EF-hand domains, and binding of these ions leads to conformational change and downstream effects, similar to the well-studied protein, calmodulin (Leisner et al., The FASEB Journal 30, 2640-2650 (2016)). We previously identified CIB2 impairment associated with deafness and/or vision deficits in humans, zebrafish, and drosophila (Riazuddin et al., Nature genetics 44, 1265-1271 (2012)). Here we explore the function of CIB2 in the aging retina using mouse models and RPE/choroid tissues from humans affected with dry AMD.

In the retina, CIB2 is expressed in the RPE, certain ganglion cells, and photoreceptors (FIG. 5b-f). To determine the function of CIB2 in the mammalian retina, we used $Cib2^{tm1a}$ mutant mice (FIG. 5a, $Cib2^{KO}$ henceforth) (GIESE et al., Nature Communications 8, 43 (2017))[12], that lack CIB2 in the RPE (FIG. 5g) as well as other retinal layers. Non-invasive in vivo scotopic full-field electroretinograms (ERG, illustrated in FIG. 1a), which preferentially analyzes rod function, showed no difference in a-wave (derived primarily from the photoreceptor layer) or b-wave (derived from the inner retina, predominantly Müller and outer nuclear bipolar cells) amplitudes in one-month-old Cib2 deficient mice. However, at 3, 6, and 9 months both, $Cib2^{KO/+}$ and $Cib2^{KO/KO}$ mice exhibited similar age-related declines (~20-30%) in both a- and b-wave amplitudes as compared with those of wild type (WT) mice (FIG. 1b, and FIG. 6a-b), but not in latency or oscillatory potential, suggesting the inner retinal function is not impacted (FIG. 6c, 6e). In contrast, the b-wave amplitude of the photopic ERG, which evaluates cone PR, were similar across all three genotypes (FIG. 6d). These results suggest that both complete loss of CIB2 and its haploinsufficiency lead to rod PR dysfunction in mice.

To determine if corresponding anatomical changes occurred with progressive loss of PR function, we evaluated the morphology of the retina in 2 and 8-9 month-old CIB2-deficient mice. Light microscopy based morphometric analysis of the specific retinal strata showed no significant differences in the specific retinal layer thickness in Cib2$^{KO/+}$ and Cib2$^{KO/KO}$ compared to those of WT mice at either age (FIG. 7). At the transmission electron microscopic (TEM) level, we observed vacuoles with undigested membranous material and loss of basal infoldings in the RPE of Cib2$^{KO/+}$ and Cib2$^{KO/KO}$ mice, but not in age-matched control mice (FIG. 1c). Staining with the neutral lipid tracer BODIPY™ 493/503 revealed 2-fold more lipid droplets in the RPE of aged Cib2$^{KO/+}$ and Cib2$^{KO/KO}$ mice (FIG. 1d, and FIG. 6f). Together, these results suggest that loss of CIB2 causes excessive lipid accumulation in RPE and is associated with progressive rod PR dysfunction.

In the mammalian retina, PR and RPE are codependent, such that functional impairment of one layer negatively impacts the other (Valapala et al., Autophagy 10, 480-496 (2014); Kim et al., Cell 154, 365-376 (2013); Barabas et al., Proceedings of the National Academy of Sciences 110, 5181-5186 (2013); Sethna et al., Journal of Biological Chemistry 291, 6494-6506 (2016)). To pinpoint the anatomical site of age-related rod PR dysfunction seen in Cib2-deficient mice we generated two cell type-specific mutant strains, in which Cib2 expression is ablated either in rod PR (designated PR-Cre+) using the rod PR-specific rhodopsin-iCre75 (Li et al., genesis 41, 73-80 (2005); or in RPE (designated RPE-Cre+) using the RPE-specific Vmd2 promoter (Iacovelli et al., Investigative Ophthalmology & Visual Science 52, 1378-1383 (2011)) (FIG. 5a and Methods). ERG analyses revealed that RPE-specific Cib2$^{KO}$ (Cib2$^{flox/flox}$; RPE-Cre+ and Cib2$^{flox/+}$; RPE-Cre+) mice had reduced ERG amplitudes compared to control mice (Cib2$^{+/+}$; RPE-Cre+) as early as age 3 months, similar to Cib2 global knockout mice, that declined further with age (FIG. 1e, and FIG. 8a-b). In contrast, we found no differences compared to control mice in either a- or b-wave amplitudes in PR-specific Cib2$^{KO}$ (Cib2$^{flox/flox}$; PR-Cre+ and Cib2$^{flox/+}$; PR-Cre+) mice, at any age tested (FIG. 1f and FIG. 9a-b). We found no morphometric histological differences in thickness of RPE- and PR-specific Cib2$^{KO}$ mice retinal strata (FIG. 9c-d, data not shown), but TEM revealed sub-RPE deposits in RPE-specific Cib2$^{KO}$ mice (FIG. 1g), that were absent in PR-specific mutants (FIG. 9c). As in global Cib2$^{KO}$ mice, we found more lipid droplets in the RPE of RPE-specific Cib2$^{KO}$ mice (FIG. 8c). Taken together, the retinal functional and morphological analyses in three mutant strains suggest that rod PR dysfunction occurs secondary to loss of CIB2 function in RPE, but not in rod PRs.

Defects in the OS renewal process (pruning of distal most photo-damaged PR disks by the RPE) in mice can lead to formation of vacuoles and accumulation of lipids (Valapala et al., Autophagy 10, 480-496 (2014), a phenotype similar to that of Cib2$^{KO}$ mice. Key functions of RPE include LC3B-associated phagocytosis (LAP) of ingested rod OS and clearance in a diurnal light-entrained circadian manner (Strauss et al., Physiological Reviews 85, 845-881 (2005). Any rhodopsin, constituting 80% of rod OS protein content, found in the RPE is from phagocytosed OS that can be used as a marker to track the OS renewal process (Sethna et al., Journal of Biological Chemistry 291, 6494-6506 (2016); Sethna cl al., (eds. Weber, B. H. F. & Langmann, T.) 245-254 (Humana Press, Totowa, NJ, 2013)). In situ, in RPE/choroid whole mounts we found that opsin-phagosomes counts 1 hr after light onset, corresponding to peak of OS ingestion (Sethna et al., Journal of Biological Chemistry 291, 6494-6506 (2016)), were similar in Cib2$^{KO}$ and control (WT) mice, indicating that binding and ingestion of OS were unaffected by Cib2 deficiency. However, Cib2$^{KO}$ mice exhibited significantly higher numbers of opsin-phagosomes 8 and 12 hr after light onset, representing slower phagolysosomal clearance (FIG. 2a-b and FIG. 11a-b). The mean diameters of opsin-phagosomes decreased in tandem with time from onset of light-on in WT animals, but in Cib2$^{KO}$ mice such decreases were delayed, further indicating that Cib2 deficiency leads to phagolysosomal dysfunction (FIG. 11c). TEM imaging of two-month-old mice retinae dissected 8 hr after light onset revealed that Cib2$^{KO/+}$ and Cib2$^{KO/KO}$ mice exhibited marked accumulation of improperly-digested remnants, lipid droplets fused with undigested material, small vacuoles, and/or fused phago-melanosomes (FIG. 2c-d). Similar deficits were observed in RPE-specific Cib2$^{KO}$ mice 8 hr after light onset (FIG. 2g-h).

Proper clearance of ingested OS requires optimally functional autophagy-lysosomal machinery. In RPE, the aspartyl protease cathepsin D is essential for phagosome digestion (Sethna et al., Journal of Biological Chemistry 291, 6494-6506 (2016)). Cathepsin D is translated as ~50 kD pro-cathepsin D and matures to its active form (~30 kDa) in the low-pH lysosomal milieu. RPE flat mounts ex vivo probed with BODIPY-pepstatin A, which binds specifically to mature cathepsin D. showed a marked ~2.5-fold reduction in indirectly-stained lysosomes, and hence available mature cathepsin D in Cib2$^{KO/+}$, Cib2$^{KO/KO}$, and RPE-specific Cib2$^{KO}$ mice (FIG. 2e-f, i-j, and FIG. 7a-b), but not in PR-specific Cib2$^{KO}$ mice (FIG. 2k and FIG. 10b). Further, immunoblotting revealed markedly reduced levels of mature cathepsin D, consistent with the BODIPY-pepstatin A labeling. LAMP-1, and ATG5-ATG12 complex in Cib2$^{KO/KO}$ mice, both, 1 and 12 hr after light onset (FIG. 12a-b).

Complementary to the findings of Cib2 mutant mice, over-expressing CIB2 in RPE-J cells increased LAMP-1 and ATG5-ATG12 complex proteins levels (FIG. 12c-d). To assess whether CIB2 overexpression has functional impact, we performed in vitro pulse-chase phagocytosis assays (Sethna et al., Journal of Biological Chemistry 291, 6494-6506 (2016)) followed by immunoblotting for opsin in RPE-J cells (schematic—FIG. 12e, left panel). Again, in agreement with our findings in mice, we detected similar opsin levels bound initially (pulse-0 h) with control or CIB2 overexpression. However, 6 hr later, corresponding to the digestion phase, we found less opsin in cells with excessive CIB2, suggesting that CIB2 overexpression alone suffices to boost phagolysosomal digestion (FIG. 12e-f). Collectively, our results suggest that lack of CIB2 in the RPE causes abnormal OS phagolysosomal processing due to reduced numbers of lysosomes and lysosomal protein levels, whereas transient CIB2 overexpression augments OS clearance. Non-canonical autophagy such as phagolysosomal OS processing shares many aspects and proteins with canonical autophagy (Kim et al., Noncanonical Autophagy Promotes the Visual Cycle. Cell 154, 365-376 (2013)). Hence, we reasoned that autophagy is impaired in Cib2 mutant mice. To test this idea, we assessed LC3-II flux. LC3-I is a cytosolic protein which when lipidated with a phosphatidyletha-nolamine adduct (LC3-II form) localizes to the growing auto/phagosome membrane, and thus can be used as a reliable readout for the dynamic autophagic process (Valapala et al., Autophagy 10, 480-496 (2014); Kim et al., Noncanonical Autophagy Promotes the Visual Cycle. Cell 154, 365-376 (2013); Klionsky et al., Autophagy 12, 1-222

(2016)). RPE/choroid whole mounts, ex vivo, were incubated overnight with DMSO (control) or bafilomycin A1, which blocks autophagosome fusion with lysosomes, and the relative ratio of LC3-II (bafilomycin A1/DMSO, LC3 flux) was assessed with immunoblotting (Klionsky et al., Autophagy 12, 1-222 (2016)). We found ~50% reduction in relative LC3 flux in $Cib2^{KO/+}$, $Cib2^{KO/KO}$, and in RPE-specific $Cib2^{KO}$ mice (FIG. 13a-d). To induce autophagy in vivo, we fasted animals for 24 hr and collected the RPE/choroid. Immunoblots of RPE/choroid lysates from autophagy induced $Cib2^{KO/+}$ and $Cib2^{KO/KO}$ mice showed that their p62/SQSTM1 and LC3-II levels doubled as compared to those in WT age-matched controls (FIG. 2l-m). When autophagy is fully functional, the levels of autophagosome membrane protein LC3-II increase, while those of the autophagosome marker protein p62/SQSTM1 decrease in concert, due to specific digestion within the autolysosome. When autophagy is faulty, levels of both p62/SQSTM1 and LC3-II increase (Klionsky et al., Autophagy 12, 1-222 (2016)). In addition, overexpressing CIB2 in RPE-J cells markedly increased relative LC3 flux in the presence of bafilomycin A1. The mTOR inhibitor rapamycin similarly elevated LC3-II levels (FIG. 13c-f). These results strongly support the role of CIB2 in clearance of autophagosomes. without compromising autophagosome biogenesis.

Since mTORC1 is a negative regulator of autophagy, we hypothesized that in the absence of CIB2, mTORC1 may be aberrantly activated. To test this hypothesis, we measured phosphoprotein levels of the bonafide mTORC1 downstream targets 4E binding protein 1 (4E-BP1) and S6 kinase 1 (S6K1). RPE/choroid lysate immunoblots from mutant mice undergoing induced autophagy revealed an approximately two-fold increase in 4E-BP1 and S6K1 phosphoprotein levels, but we found no difference in levels of the mTORC2 downstream target phospho-AKT. (FIG. 2n-o), Together, the results suggest that CIB2 impacts autophagy in the RPE, specifically by modulating mTORC1.

mTORC1 integrates various metabolic and amino acid signals through its nutrient-sensing arm and growth signals, which converge on the small GTPase Rheb, via the TSC complex (Wolfson et al., Cell Metabolism 26, 301-309 (2017)). We first tested if CIB2 is a specific negative regulator of mTORC1 and/or mTORC2. We used HEK293 cells, because the mTORC1 signaling pathway is well-established in this cell line, and to expand CIB2 functions beyond the RPE. HEK293 cells overexpressing increasing amounts of CIB2 showed decreasing phosphorylation of the mTORC1 targets 4E-BP1, S6K1, and ULK1. We found no changes in mTORC2-mediated phosphorylation of AKT (FIG. 3a), further suggesting CIB2 specifically regulates mTORC1 but not mTORC2 signaling.

To reveal the molecular mechanism of CIB2-mediated mTORC1 modulation, we focused on the TSC-Rheb-mTORC1 axis. We performed an interaction screen of specific proteins including TSC1, TSC2, mTORC1-specific subunit Raptor, mTOR kinase, and Rheb. We used a recently-published quantitative interaction assay known as nanoscale pulldown 2.0 (NanoSPD), in which eGFP-nanobody tag fused to the myosin-HMM domain (nanoTRAP) preferentially migrates to the filopodia (Bird et al., Molecular Biology of the Cell 28, 463-475 (2017)). CIB2-eGFP (bait) migrated efficiently to filopodia in COS-7 cells only in the presence of the nanoTRAP. HA-GST-Rheb, HA-mCherry-Raptor, or myc-mTOR when co-transfected with nanoTRAP and GFP-METTL5 or GFP-FAM92A1 as control, did not accumulate at the tip of the filopodia, showing that the tested proteins or tags do not influence filopodia tip localization (FIG. 14a, d). Further, TSC1 and TSC2, the major proteins of the TSC complex directly regulating Rheb, did not show any co-accumulation with CIB2-eGFP (FIG. 14b, d). Many downstream and upstream targets of mTORC1 regulate its activity via binding to the mTORC1-specific subunit Raptor. Using NanoSPD, we found that Raptor, but not mTOR, interacts with CIB2. mTOR efficiently accumulated at filopodia tips only in the presence of Raptor, suggesting a tripartite complex with CIB2 (FIG. 14c-d). We further confirmed the interaction of Raptor with CIB2 using co-immunoprecipitation (co-IP) assays (FIG. 3b).

NanoSPD further revealed that CIB2 interacts with Rheb (FIG. 14c-d). A recent study showed that GTP-bound Rheb activates mTORC1 by directly interacting with mTOR kinase, leading to a conformational change that exposes the mTORC1 kinase domain (Yang et al., Nature 552, 368 (2017)). We tested the essentiality of nucleotide binding state of Rheb using co-IP assays. First, we confirmed that tdTomato-CIB2 co-immunoprecipitated with HA-GST-Rheb (FIG. 3c). Next, we used the Q64L and S20L Rheb variants, which mimic the GTP- and GDP-bound state, respectively. Consistent with prior findings (Heard et al., Cellular signalling 26, 1950-1957 (2014), we found that the Rheb-S20L variant protein was unstable and degraded quickly (FIG. 3c—input). In co-IP assay, CIB2 bound preferentially to the S20L variant as compared to either Rheb-WT or Rheb-Q64L variant (FIG. 3c). Furthermore, CIB2 binds more strongly to GDP-bound Rheb than to GTP-bound Rheb, seen by loading glutathione bead-immobilized HA-GST-Rheb (WT) with either GDP or non-cleavable GTPγS and adding tdTomato-CIB2 lysate (FIG. 3d). These findings revealed that the specific GDP– (vs. GTP–) bound state of Rheb is critical for CIB2 binding. Together, the results suggest that CIB2 modulates mTORC1 activity by preferentially binding to GDP-Rheb, besides acting as a linker to mTORC1 by binding to Raptor. Together our mouse and biochemical studies demonstrate that loss or lower levels of CIB2 in the RPE leads to overactive mTORC1 via binding to GDP-Rheb and raptor, reduced autophagy, leading to secondary impairment of PR function (FIG. 3c).

AMD is a progressive degenerative disease of the macula, a specialized region of the retina responsible for daytime vision, and can cause central vision loss and irreversible blindness. AMD affects 10% of the population aged 65-75 years and 25% of those aged ≥75 years. By 2050, its prevalence is expected to increase by 50% (Wong et al., The Lancet Global Health 2, e106-e116 (2014); Brown et al., Transactions of the American Ophthalmological Society 103, 173-186 (2005). AMD is characterized by drusen accumulation in the inner collagenous layer of Bruch's membrane, RPE vacuolization, and accumulation of lipid deposits (lipofuscin) within the RPE, Bruch's membrane, and elsewhere. Aging-associated lipofuscin accumulation is further thought to hinder lipid degradation by phagolysosomes and autolysosomes in RPE, exacerbating accumulation of undigested lipids (Vives-Bauza et al., The Journal of Biological Chemistry 283, 24770-24780 (2008)), and is an important causative factor in dry AMD. Both non-canonical and canonical autophagy is essential for RPE in mouse models (Valapala et al., Autophagy 10, 480-496 (2014); Kim et al., Noncanonical Autophagy Promotes the Visual Cycle. Cell 154, 365-376 (2013); Sethna et al., Journal of Biological Chemistry 291, 6494-6506 (2016); Kaarniranta et al., Autophagy 9, 973-984 (2013); Yao et al., Autophagy 11, 939-953 (2015)) and humans (Golestanch et al., Disease 8, e2537 (2017); Mitter et al., Advances in experimental medicine and biology 723, 83-90 (2012); Kaarniranta et al., Autophagy 9, 973-984 (2013). Based on our mouse model data, we reasoned that upregulated mTORC1 might be responsible for these autophagy deficits and AMD in humans. To test this, we evaluated RPE/choroid tissues bio-banked from human subjects affected with dry AMD (n=8) along with age-matched control (n=10) tissues. Consistent with observations made in primary RPE cell cultured from AMD patients (Golestanch et al., Disease 8, e2537 (2017)), autophagy was impaired in dry AMD RPE/choroid lysates, as exhibited by accumulation of both p62/SQSTM1 and LC3. Further, dry AMD patients' lysates exhibited reduced CIB2 expression, and higher levels of phosphorylated, but not of total protein levels, ULK1 and 4E-BP1 (FIG. 3f-g and FIG. 15), indicating hyperactive mTORC1 signaling. These results demonstrate that patients with dry AMD also had reduced CIB2 levels, over-active mTORC1 signaling and autophagy deficits in the RPE/choroid tissue.

Upregulated mTORC1 signaling is also implicated in aging. TSC, and cancers, including LAM. Further, TSC variants lead to RPE lesions in human patients (Shields et al., Archives of Ophthalmology 130, 387-390 (2012)). Since CIB2 interacts with Rheb, but not its direct upstream regulator TSC complex, we reasoned that CIB2 overexpression can partially down-regulate the hyper-activated mTORC1 signaling observed in TSC. LAM is a progressive lung disease commonly observed in ~80% of women suffering with TSC, while renal angiomyolipoma, occurs in ~60% of all TSC patients (Henske et al., Tuberous sclerosis complex. Nature Reviews Disease Primers 2, 16035 (2016)). The patient-derived cell line LAM-621 (LAM-associated renal angiomyolipoma) harbors a variant in TSC2 (p.Arg611Gln) rendering it unable to complex with TSC1, resulting in hyperactivated mTORC1 signaling (Yu et al., American Journal of Physiology-Lung Cellular and Molecular Physiology 286, L694-L700 (2004)). LAM-621 cells overexpressing increasing amounts of CIB2, showed decreasing amounts of phosphorylated 4E-BP-1 and ULK1, but not AKT (FIG. 3h, left panel). Finally, in $Tsc2^{KO/KO}$, $p53^{KO/KO}$ mouse embryonic fibroblasts (MEFs) over-expressing CIB2, we observed similar reduction in mTORC1 but not mTORC2 targets (FIG. 3h, right panel), suggesting that CIB2 can partially downregulate mTORC1, independently of TSC complex, and thus our findings also have implications for other mTORC1 hyperactive disorders.

Direct mTOR kinase inhibitors or rapamycin (and its analogs) have shown only limited success in geographic atrophy patient trials (Petrou et al., Investigative Ophthalmology & Visual Science 56, 330-338 (2015); Gensler et al., Ophthalmology Retina 2, 441-450 (2018), as chronic exposure to either class of compounds also leads to mTORC2 disassembly and affects cell survival (Sarbassov et al., Molecular Cell 22, 159-168 (2006)). Since direct mTOR inhibition is not a viable long term strategy, there are intense efforts to discover drugs modulating the mTORC1 pathway by targeting other players of the pathway such as RHEB (Mahoney et al., Nature Communications 9, 548 (2018)). CIB2 is a small gene that can easily fit within the carrying capacity of AAV for in vivo delivery, supporting potential translatability via gene therapy. Also, autophagy is linked to lysosomal biogenesis via transcription factor EB (TFEB) family, the lysosomal master transcription factor family (TFEB/TEF3/MiTF) via which mTORC1 controls lysosomal biogenesis (Martini-Stoica et al., Trends in Neurosciences 39, 221-234)). The reduction of lysosomal proteins in RPE of $Cib2^{KO}$ mice could potentially be mediated via mTORC1 regulation of TFEB. If so, CIB2 overexpression might be dually beneficial, by reducing mTORC1 activation, and thereby upregulating autophagy and lysosomal biogenesis, promising topics for further basic or translational studies.

RPE is essential for the visual cycle regeneration of 11-cis retinal, the chromophore of PR opsins. Upon photon absorption, 11-cis retinal is photo-isomerized to all-trans retinal, thereby activating opsin and initiating the phototransduction cascade (Saari et al., Investigative Ophthalmology & Visual Science 41, 337-348 (2000); Wald et al., Nature 177, 174-176 (1956)). All-trans retinal is regenerated to 11-cis retinal that is recycled back to PR, via a series of transport and enzymatic steps, occurring mainly in the RPE (illustrated in FIG. 4a). The ERG deficits without significant PR damage led us to investigate this key visual pathway. We quantified the absolute retinoid levels within the retina or RPE/choroid in 2- to 3-month and 8- to 9-month old $Cib2^{KO/+}$, $Cib2^{KO/KO}$, and control age-matched WT mice. We found no significant differences in the key retinoid species, including 11-cis oxime, all-trans oxime, retinyl esters, and A2E at either age in mutant vs. WT mice (FIG. 16). We reasoned that the vacuoles observed in the RPE may partially sequester retinoids, rendering them unavailable to re-enter the PR. Therefore, we tested whether we could rescue the ERG defects by bypassing the RPE visual cycle all-together, by supplying exogenous chromophore. We used two different treatment paradigms in our two Cib2 mutant models. We injected aged global $Cib2^{KO}$ (either heterozygous or homozygous) mice once with either 9-cis retinal (analog of 11-cis retinal) or vehicle, then assessed their visual function by ERG the following day, after dark adaptation. Treatment of $Cib2^{KO}$ mice with 9-cis retinal restored their ERG amplitudes to near WT levels, with significant differences in scotopic a- and b-wave amplitudes as compared to vehicle-injected $Cib2^{KO}$ controls (FIG. 4b, WT ERG amplitudes reproduced for comparison from FIG. 6b).

Figure 4:
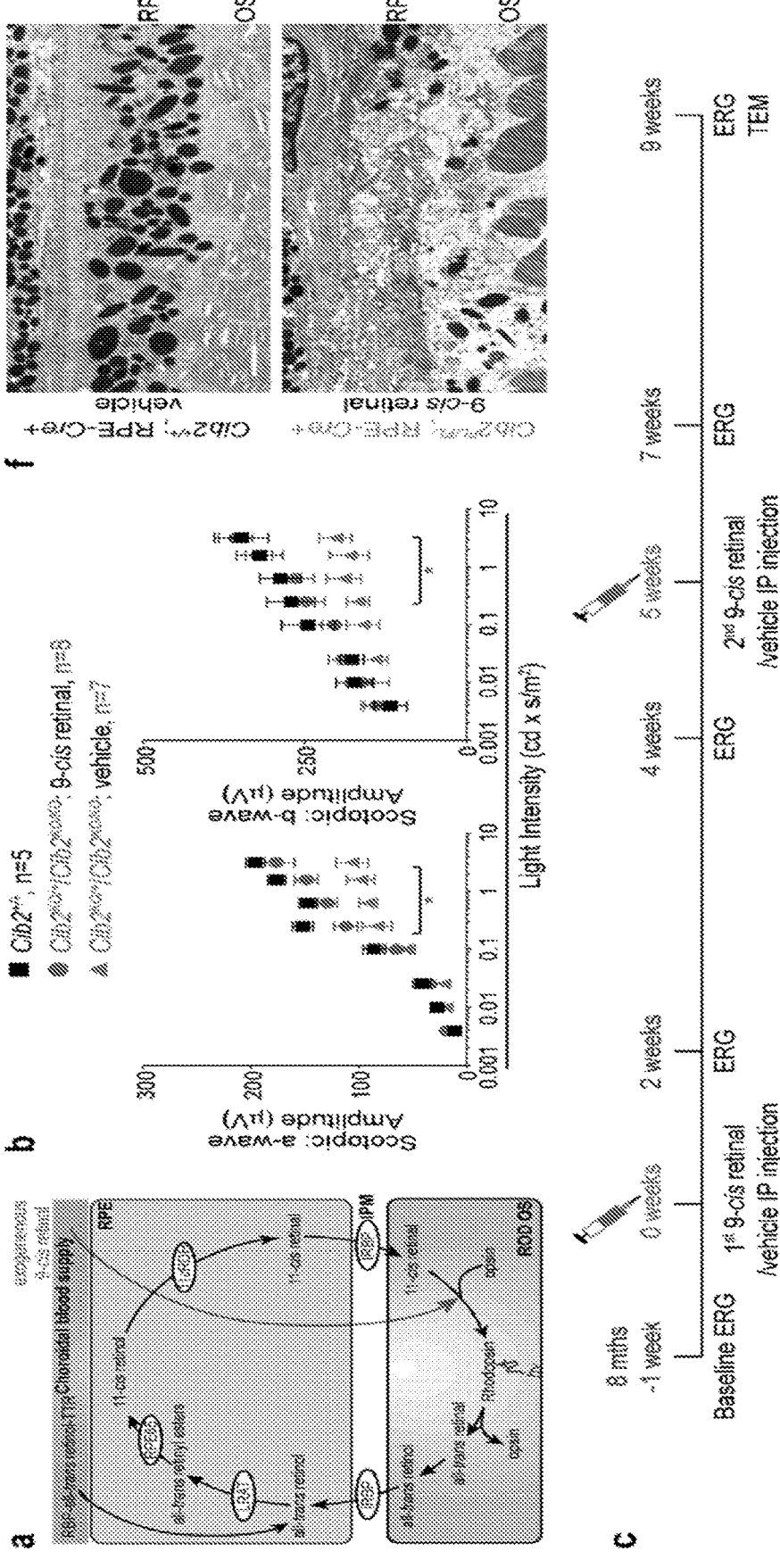
FIG. 4. PR function but not RPE pathology can be rescued by exogenous retinoid supplementation. a. Schematic of the visual cycle and exogenous 9-cis retinal treatment. b. 8-9 month old Cib2 mutant mice (Cib2$^{KO/+}$ and Cib2$^{KO/KO}$) injected intraperitoneally with 0.25 mg 9-cis retinal, dark adapted overnight, showed improved ERG a- and b-wave amplitudes as compared to vehicle injected mice. For comparison, untreated WT control mice (black squares) are replotted from FIG. 6b. c, Schematic of treatment paradigm in RPE-specific Cib2$^{KO}$ injected with 9-cis retinal and control mice injected with vehicle. d. Baseline ERG for indicated genotype are reproduced from FIG. 8b. e. ERG amplitudes for indicated genotype after specific treatment as outlined in c showed that 9-cis retinal treatment temporarily
Figure 4:
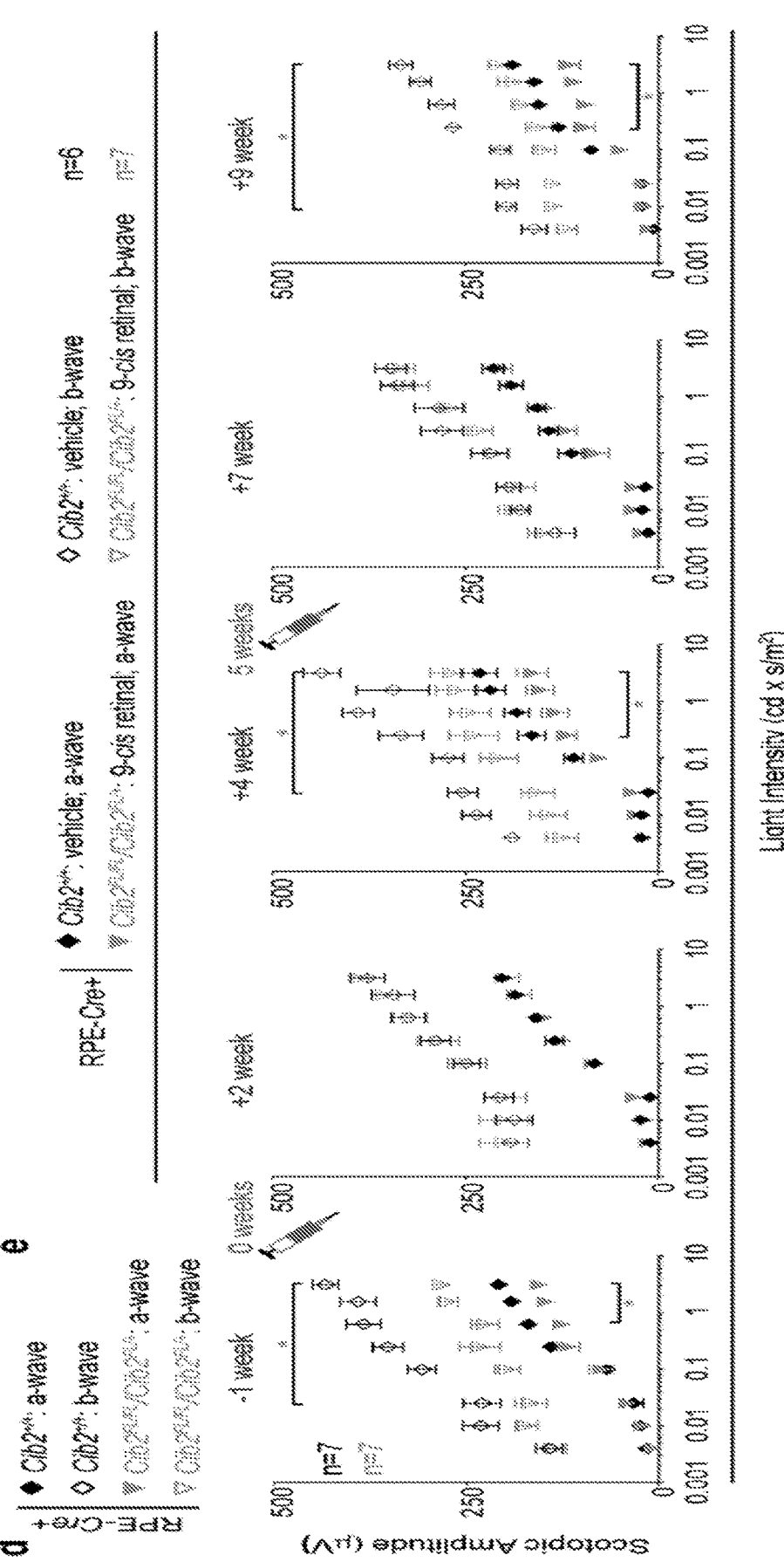

To further assess the potential clinical translatability of exogenous retinoids, we tested an extended treatment paradigm following injection of 9-cis retinal in RPE-specific $Cib2^{KO}$ mice (FIG. 4c). We performed baseline ERGs on 8 month old uninjected mice (FIG. 4d—reproduced from FIG. 8b). Two weeks after the $1^{st}$ injection, ERG amplitudes for RPE-specific $Cib2^{KO}$ mutant mice injected with 9-cis retinal were indistinguishable from those of vehicle-injected RPE-Cre+ controls. The rescuing effect of exogenous retinoid was short-lived, because by four weeks post-injection, the ERG amplitude differences between groups had returned to their baseline levels prior to the 9-cis retinal treatment. To assess medium-term efficacy of exogenous retinoid therapy, we extended the paradigm further by one month. Again, we saw no discernable inter-group differences two weeks after the $2^{nd}$ injection, but by four weeks after the $2^{nd}$ injection, ERG amplitudes diverged significantly (FIG. 4c), suggesting short-term but reproducible improvement in ERG amplitudes by such treatment. At the conclusion of treatment, TEM analysis of the RPE revealed vacuoles and/or sub-RPE drusen present in all three 9-cis retinal-treated RPE-specific $Cib2^{KO}$ mice (3 of 3), but not in vehicle-treated RPE-Cre+ control mice (1 of 3) (FIG. 4f). The results strongly suggest that repeated exogenous retinoid treatment can rescue PR function temporarily yet reproducibly in Cib2 deficient mice, by bypassing the RPE, although, as expected, without improving RPE pathophysiology. Bypassing the RPE visual cycle by supplying exogenous retinoids has been found to be a useful therapeutic approach for certain retinal disorders (Maeda et al., Human Molecular Genetics 18, 2277-2287 (2009); Palczewski., Trends in pharmacological sciences 31, 284-295 (2010). In summary, our findings reveal a new mechanistic model of age-related pathology in mice and AMD in humans elicited by deficiency of mTORC1-suppressing CIB2, specifically in the RPE, resulting in pathogenic impairment of autophagy and secondarily visual function.

Methods

Animals, Tissue Harvest, and Processing

The ARRIVE guidelines for reporting animal research were used for procedures involving animals and animal studies were conducted according to the ARVO *Statement for the Use of Animals in Ophthalmic and Vision Research* and the National Institutes of Health *Guide for the Care and Use of Laboratory Animals*. All animal procedures were reviewed and approved by the IACUC (Institutional Animal Care and Use Committees) of the University of Maryland School of Medicine. $Cib2^{tmIa}$ mice (designated $CIB2^{KO}$) were purchased from EUCOMM and validated by us and other laboratories recently (Giese et al., Nature Communications 8, 43 (2017); Michel et al., EMBO Molecular Medicine 9, 1711-1731 (2017)). To generate floxed allele ($Cib2^{FL}$), $Cib2^{tmIa}$ were crossed ROSA26::FlPe knock in mice (Jax lab, stock #003946), which resulted in the removal of LacZ-neomycin selection cassette by Flp-FRT recombination. RPE-specific Cre expressing mice were described earlier (Iacovelli et al., Investigative Ophthalmology & Visual Science 52, 1378-1383 (2011)), and were a kind gift from Drs. Sheldon Miller and Joshua Duniaef. Previous research pointed out that these mice may develop Cre-mediated age-dependent RPE pathology (He et al., The American Journal of Pathology 184, 1660-1667 (2014)), hence for all experiment's we used $Cib2^{+/+}$; RPE-Cre+ mice as controls. Rod photoreceptor-specific Cre-expressing mice (Li et al., genesis 41, 73-80 (2005) were purchased from Jackson Labs. Previous studies and our own studies did not show any Cre-mediated toxicity in this line, hence for controls we used a mix of $Cib2^{FL/FL}$ or $Cib2^{FL/+}$; Cre-, and $Cib2^{+/+}$; Cre+ mice. Mice were housed under a strict 12:12 h light on/off cycle and fed standard mouse diet (after weaning) and water ad libitum. Mice were killed by $CO_2$ asphyxiation followed by cervical dislocation before immediate eye enucleation. Eyes were immersion-fixed in 2% PFA-2% glutaraldehyde for morphometry and TEM.

RPE flat mounts were generated by first removing the anterior segment and lens from an eye, and then removing the retina carefully in Hank's balanced salt solution (HBSS), fixing the eyecup in 4% PFA in PBS for 30 mins to 1 hr, followed by radial cuts to flatten the eyecup, and antibody/dye labeling performed for fluorescence microscopy. For immunoblots of RPE/choroid tissue extracts, eyes were enucleated, opened to remove the lens, retinae dissected from posterior eyecups, and resulting RPE/choroid tissues snap-frozen on dry ice before storing at −80° C. before lysis. For retinoid analysis, mice were dark-adapted overnight and the above dissection was done under dim red light. For autophagy flux assay, whole mounts of RPE/choroid without radial cuts were incubated in DMSO (control) or 50 nM Bafilomycin A1 overnight in DMEM at 37° C. before rinsing with PBS, tap drying on filter paper, followed by snap-freezing on dry ice and storing at 80° C. before lysis and immunoblotting. For assessing mTORC1 activity following increased autophagy in vivo, mice were fasted with unlimited access to water for 24 hr, followed by RPE/choroid dissection as above.

Morphometric Analysis of the Outer Retina

Plastic sections were prepared as previously described (Scott et al., 2011). Eye were hemisected from the pupil through the optic nerve and the eyecups harvested for morphological analysis. Eyecups were dehydrated in ascending ethanol concentrations, infiltrated, and embedded in JB-4 Plus resin (Ted Pella, Redding, CA). Sections 4 µm thick were cut on a Leica EMUC6 Ultramicrotome (Leica Microsystems, Buffalo Grove, IL), mounted on slides, dried, and stained with 1% cresyl violet (Sigma, St. Louis, MO). Sections were examined at 40× or 100× using a NIKON EFD-3 Episcopic-Fluorescence microscope (Nikon Inc., Melville, NY). Photomicrographs were taken using a Moticam 2500 high-resolution camera (Motic, British Columbia, Canada) and brightness and contrast adjusted as needed using Adobe Photoshop (Adobe Systems, San Jose, CA).

To measure the thicknesses of outer retina strata, a vertical line was drawn from the outer plexiform layer (OPL) to the RPE, and the OPL, outer nuclear layer (ONL), PR OS, and distances of inner segment (IS) edges measured individually from this line using Moticam Image Plus 2.0 Software (Motic China Group Co., Ltd., Xiamen, China), in 10 sections per eye, and overall means calculated. Retinal thickness was measured without knowledge of the genotype by a masked observer (PAS).

Transmission Electron Microscopy

Sections for EM were prepared as previously described 48. Briefly, hemisected eyecups were rinsed in buffer and postfixed in 2% osmium tetroxide and 1.5% potassium ferrocyanide in $dH_2O$ for 2 hr, dehydrated in a graded ethanol series, and embedded in Epon-Araldite (Electron Microscopy Sciences, Hatfield, PA). Semi-thin sections (4 µm) were cut and stained with 1% cresyl violet. Ultra-thin sections (90 nm) were cut on an ultramicrotome (Ultracut E 701704, Reichert-Jung, Buffalo, NY) using a diamond knife (Micro Star Technologies, Inc., Huntsville, TX), collected on copper grids, counterstained with 4% methanolic uranyl acetate (Electron Microscopy Sciences, Hatfield, PA), and outer retinal morphology examined using a transmission electron microscope (TEM; Model 300: Phillips, Eindhoven, The Netherlands). Photomicrographs were captured with a digital camera (15 megapixel digital camera, Scientific Instruments and Applications, Duluth, GA) and Maxim DL Version 5 software (Diffraction Limited, Ottawa, Canada).

Electroretinography

Electroretinograms (ERG) were recorded as earlier described[14] with modifications. Mice, overnight dark-adapted, were anesthetized with ketamine-xylazine (100 mg/kg and 10 mg/kg, respectively) and pupils were dilated with 1% Tropicamide. A gold wire lens electrode was placed on the cornea, a platinum reference electrode in the mouth, and a ground electrode on the tail. To assess rod-driven responses, increasing scotopic stimuli were presented sequentially (0.003962233 to 3.147314 cd×s/m2) with 5-60 sec intervals using UTAS BigShot (LKC Technologies, Gaithersburg, MD). At least 3 waveforms per intensity were averaged. For cone function evaluation, photopic responses to a single bright flash (3.15 cd×s/m2) under a steady rod-suppressing field of cd×s/m2. Waves were analyzed using EM for Windows software (LKC Technologies).

Cell Culture, Drug Treatment, Synchronized Cell Culture Phagocytosis Assay

Immortalized RPE-J cells derived from rat (ATCC, Manassas, VA) were maintained at 32° C. and 8% $CO_2$ in 4% FBS/DMEM supplemented with 1× penicillin/streptomycin. HEK-293T. COS-7, LAM-621, and $TSC2^{KO/KO}$ $p53^{KO/KO}$ MEF cells were maintained at 37° C./5% CO2 in 10% FBS-DMEM supplemented with 1× penicillin/strepto-mycin. OS were purified from fresh porcine eyes harvested within 24 hrs from Sierra For Medical Science (Whittier, CA) using an established protocol (Parinot et al., Large-Scale Purification of Porcine or Bovine Photoreceptor Outer Segments for Phagocytosis Assays on Retinal Pigment Epithelial Cells. e52100 (2014)), modifying only the preparation of sucrose density gradient tubes. 24 hr before OS purification, sucrose step gradients (20%-60% in 10% increments) were prepared in ultracentrifugation tubes and frozen at −20° C. at ~45° angle. On the day of purification, a continuous gradient was formed by thawing at room temperature at this angle. Pulse-chase experiments were performed as we described (Sethna et al., Journal of Biological Chemistry 291, 6494-6506 (2016)). RPE-J cells transiently overexpressing AcGFP or CIB2-IRES-AcGFP were challenged with ~10 OS/cell in serum-free DMEM with 1 µM MFG-E8 for 1 h at 20° C. (pulse, POS binding only). After washing unbound POS with PBS, cells were chased for indicated times at 32° C. with 5% FBS-supplemented DMEM. At the end of the pulse or chase period, cells were rinsed 3× with PBS before lysis in RIPA buffer with a solution containing 1× protease inhibitors, 1 mM Na orthovanadate, 10 mM Na glycerophosphate, and 10 mM NaF, and stored at −80° C. until immunoblotting.

X-Gal Staining, nanoSPD, Lipid Droplet, and Indirect Lysosome Labeling

For X-gal staining. Cib2$^{WT/WT}$ (control) and Cib2$^{KO/+}$ nucleated eyes were fixed for 1 h in 0.5% glutaraldehyde (0.5%)-NP-40 (0.02%) diluted in PBS, followed by washing with PBS 2× for 5 min. Eyecups were stained O/N at 37° C. in tubes covered with aluminum foil with PBS, in a solution of 1 mg/ml X-Gal, 5 mM $K_3Fe(CN)_6$, 5 mM $K_4Fe(CN)_6$, 2 mM $MgCl_2$, 0.02% NP-40, and 0.01% sodium deoxycholate. The next day, eyes were washed once for 5 min in PBS followed by post-fixation with 2% PFA-2% glutaraldehyde in PBS for at least 1 hr at RT. An opening was made in the lens region to allow OCT penetration. Eyes were embedded in OCT using standard protocols. 20-30 µm-thick sections were cut on a Cryotome (Leica, Germany).

Phagosome counts in whole mounts of RPE were performed essentially as we described, with Ret-P1 antibody (Sethna et al., Journal of Biological Chemistry 291, 6494-6506 (2016)). Whole-mount RPE/choroid preparations were live-stained with 1 µM BODIPY-Pepstatin A or 0.1 mg/ml BODIPY-493/503 in DMEM at 37° C. for 30 min followed by fixation with 4% PFA.

60-70% confluent COS-7 cells or RPE-J cells were fixed with 4% PFA for 15 min at RT and permeabilized with 0.2% Triton X-100 in PBS for 15 min at room temperature, followed by blocking with 10% normal goat serum (NGS) in PBS for at least 30 min at RT. Primary antibodies were diluted in 3% NGS-PBS and incubated overnight at 4° C., followed by the incubations with the indicated goat secondary antibodies. Phalloidin-647 or rhodamine-phalloidin was added at dilutions of 1:1000 (COS-7) or 1:200 (RPE-J) during secondary antibody incubation to stain F-actin. A Zeiss 710 laser scanning confocal microscopy system was used for image acquisition, with step size of 0.5 µm. Fiji (Image)) (Schindelin et al., Nature Methods 9, 676 (2012)) was used to process images, and average numbers of phagosomes per 100 µm² of retina were calculated [detailed in (Sethna el al., (eds. Weber, B. H. F. & Langmann, T.) 245-254 (Humana Press, Totowa, NJ, 2013))]. For counting area of undigested material or mitochondria as control (FIG. 2C, D), outlines were drawn in Fiji on TEM images from indicated genotypes of mice sacrificed 8 hr after light onset, and areas calculated using Fiji functions.

60-70% confluent Cos7 cells in 6-well plates for nano-TRAP were transfected with Lipofectamine 2000 (3:1 ratio) with 1 µg plasmid construct each. For nanoTRAP assay, cells were split 1:10 ratio in glass coverslips to allow for filopodia formation. 24 hrs later, cells were fixed and processed as above.

Transfection, Immunoprecipitation, and Immunoblotting

80% confluent HEK293 cells in 10-cm dishes were transfected for co-IP experiments with 10 µg of indicated plasmid/s using the polyethylenimine (PEI) method (3:1::PEI:DNA). 2 plates per condition were used. 36 hr later the plates were chilled on ice, washed once with ice-cold PBS, and cells collected in ice-cold PBS and centrifuged for 2 min at 1500 RPM at 4° C. Cell pellet was then lysed in IP buffer (0.3% CHAPS, 40 mM HEPES, 2.5 mM $MgCl_2$, 1× Protease inhibitors, 1 mM Na orthovanadate, 10 mM Na glycerophosphate, 10 mM NaF) on ice for 20 min, followed by centrifuging at full speed for 20 min at 4° C. Lysates were pre-cleared with control agarose beads for 1 h rotating at 4° C. 30 µl of a 50% slurry of either HA or GST beads washed 3 times in lysis buffer was added. Samples were rotated 3 hr or overnight at 4° C., washed 4 times in IP buffer, boiled in 50-100 µl SDS sample buffer at 95° C., separated by SDS-gel electrophoresis, transferred to PVDF membranes, and immunoblotted.

For GTPγS of GDP loading experiments, cleared lysates of HEK293 cells over-expressing HA-GST-Rheb were prepared as described in buffer lacking $MgCl_2$. Rheb was immobilized on GST beads by incubating for 2 h, rotating at 4° C. Beads were washed 4 times with lysis buffer without $MgCl_2$. GTPγS of GDP was added to final concertation of 100 µM and 1 mM, respectively. The tubes were incubated with shaking for 1 h at 37° C. Loading was stopped by placing tubes on ice and adding $MgCl_2$ to final concentration of 60 mM. TdTomato (control) or tdTomato-CIB2 cleared lysates were prepared as above and dividing equally to GTPγS of GDP loaded Rheb and incubated with rotation overnight. Next day the beads were washed, processed, and immunoblotted as above.

RPE-J cells transfect poorly with PEI and the standard Lipofectamine-2000 protocol. We optimized the following protocol for 24 wells: Lipofectamine 2000:DNA::3:1 was prepared in 100 µl Optimem. 2-4 µg plasmid/well was used. This very high plasmid concentration leads to toxicity for most other cell types, but works well for RPE-J cells. Cells were used for transfection at ~70% confluence. The medium was replaced with 400 µl Optimem/well (adding Optimem instead of 2% FBS-DMEM is important for transfecting RPE-J cells). The Lipofectamine/plasmid mix was added dropwise. 24 hr later the medium was changed to complete medium (4% FBS-DMEM), cells were allowed to grow/express plasmid for a further 24 hr before fixing or used for pulse-chase experiments, followed by immunoblotting. This method reliably and reproducibly gave us >60% transfection. LAM-621 and TSC2$^{-/-}$, p53$^{-/-}$ MEFs were transfected with Lipofectamine 2000 following manufacturer's instructions.

Human AMD/Control Tissue

Studies on human tissue followed the Declaration of Helsinki guidelines. Human age-matched RPE-choroid tissues were obtained from donor eyes harvested from local and national eye banks, under an IRB exemption issued by the University of Maryland-Baltimore. A complete ocular history, relevant medical history and age was obtained from each donor. Donors with dry AMD and age-matched normal donors were selected for use. We excluded donors with any eye-related diseases besides AMD, or systemic disorders that might affect retinal/RPE or choroidal function. Eyes were examined and RPE/choroidal tissue isolated by a trained Ophthalmolgist (SLB) and any additional lesions noted prior to preservation. Tissues were snap-frozen on dry ice and stored at −80° C. prior to use.

Data Analysis

For ERG analysis 4-8 animals per time point/genotype/treatment were used. For in vivo experiments, at least 3 mouse eyes (from different animals) were used for immunoblots, at least 3 images were averaged per eye from 3 eyes/indicated genotype/time point for confocal microscopy. For cell culture (in vitro) experiments, at least three independent experiments or 2 independent experiments for co-IP studies were performed. One-way ANOVA with Tukey's post-hoc test or Student's t-test was used to compare control sample to test samples, with data presented as mean±SEM. Differences with $p<0.05$ were considered significant. Data were analyzed using GraphPad Prism (GraphPad Software, Inc., La Jolla, CA).

| REAGENT or RESOURCE | SOURCE | IDENTIFIER |
|---|---|---|
| ANTIBODIES (Anti) | | |
| CIB2 (clone 59, homemade) | This paper | |
| Raptor (clone 24C12) | Cell Signaling Technology | # 2280S |
| mTOR Substrates Antibody Sampler Kit | Cell Signaling Technology | # 9862T |
| TSC1 | Cell Signaling Technology | # 4906S |
| TSC2 | Cell Signaling Technology | # 4308S |
| Actin (clone 13E5) | Cell Signaling Technology | # 4970S |
| β-Tubulin (clone 9F3) | Cell Signaling Technology | # 2128S |
| SQSTM1/p62 (clone D1Q5S) | Cell Signaling Technology | #39749 |
| Phospho-AKT 1/2/3 (ser 473) | Santa Cruz Biotechnology | sc-7985 |
| AKT 1/2/3 | Santa Cruz Biotechnology | sc-8312 |
| ULK1 (clone D8H5) | Cell Signaling Technology | # 8054S |
| Phospho-ULK1 (Ser757) (D7O6U) | Cell Signaling Technology | #14202 |
| GAPDH (clone 0411) | Santa Cruz Biotechnology | sc-47724 |
| HA.11 Epitope Tag | Biolegend | # 901501 |
| Cathepsin D | R & D systems | AF1029 |
| ATG5; N-terminal | Sigma | A0856 |
| LC3B | Novus Biologicals | NB100-2220 |
| LAMP1 | Sigma | L1418 |
| Rhodopsin Antibody, clone RET-P1 | EMD Milipore | MAB5316 |
| DsRed (recognizes tdTomato, clone OTI4C8) | OriGene | # TA180084 |
| Opsin (clone B6-30); do not boil sample for immunoblot | Novus Biologicals | NBP2-25160 |
| REAGENTS | | |
| Bafilomycin A1 | Sigma-Aldrich | B1793 |
| Rapamycin | Sigma-Aldrich | R0395 |
| Pierce ™ Anti-HA Agarose | Thermo Fisher | 26181 |
| Glutathione Sepharose ® 4B | GE Healthcare | GE17-0756-01 |
| Pierce ™ Control Agarose Resin | Thermo Fisher | INV-26150 |
| ECL ™ Prime Western Blotting System | Thermo Fisher | 32106 |
| Chaps Hydrate >=98% (hplc) | Sigma-Aldrich | SIG-C3023-25G |
| Gtp-gamma-s | Abcam | ab146662 |
| Guanosine 5'-diphosphate Sodium Type I | Sigma | G7127 |
| Lipofectamine ™ 2000 Transfection Reagent | Thermo Fisher | 11668019 |
| In-Fusion ® HD Cloning Plus | Clonetech | 638911 |
| BODIPY 493/503 | Thermo Fisher | D3922 |
| Pepstatin A, BODIPY ™ FL Conjugate | Thermo Fisher | P12271 |
| X-Gal | Sigma-Aldrich | 3117073001 |
| 9-cis retinal | Sigma-Aldrich | R5754-100MG |
| QuikChange Lightning Site-Directed Mutagenesis Kit | Agilent | 210518 |
| Recombinant Proteins | | |
| Recombinant Human MFG-E8 Protein | R & D systems | 2767-MF-050 |
| Experimental Models: Cell Lines | | |
| RPE-J | ATCC | # CRL-2240 |
| HEK-293 | ATCC | # CRL-1573 |
| LAM-621 | Kind gift from Dr. Henske | Yu et al., 2004 |
| TSC2$^{-/-}$, p53$^{-/-}$ MEF | | Zhang et al., 2003 |
| Recombinant DNA | | |
| pRK5-HA-mCherry-raptor | Addgene | 73386 |
| pRK5-HA-GST-Rheb1 | Addgene | 19310 |
| pRK5-myc-mTOR | Addgene | 1861 |
| pRK7-FLAG-TSC1 | Addgene | 8995 |
| pRK7-FLAG-TSC2 | Addgene | 8996 |
| eGFP-N2-hCIB2 | This paper | |
| tdTomato-C1-mCIB2 | This paper | |
| ptdTomato Vector-C1 | Clonetech | 632531 |
| pAAV-CIB2-IRES-AcGFP | This paper | |
| pAAV-AcGFP | Grousbeck Gene Therapy Center | |

-continued

| REAGENT or RESOURCE | SOURCE | IDENTIFIER |
|---|---|---|
| pcDNA3.1-MYO10-HMM-Nanotrap | Addgene | 87255 |
| | Software and Algorithms | |
| EM for Windows | LKC | |
| Prism 6.0 | GraphPad, La Jolla, CA | |
| Adobe Suite | Adobe, CA | |
| Fiji | https://fiji.sc/ | |
| | Mouse strains | |
| Cib2$^{tm1a(EUCOMM)Wtsi}$ mice | EUCOMM | EM:05417 |
| VMD2-Cre mice | Gift from Drs Sheldon Miller | Iacovelli et al., |
| | and Joshua Dunaief | 2011 |
| Opsin-iCre75 | Jax | Stock No: 015850 |
| ROSA26::FlPe knock in mice | Jax | Stock No: 003946 |

Example 2. Treatment of Tuberous Sclerosis Complex

Tuberous Sclerosis Complex (TSC) is an autosomal dominant multisystem tumor suppresser disorder with ~1 million people affected worldwide. The key defining feature of TSC is multi-organ benign tumors including skin, brain, lung, and kidney. TSC is caused by inactivating variants in TSC1 or usually TSC2 (encoding hamartin and tuberin, respectively) leading to hyperactivated mTORC1 (mechanistic target of rapamycin complex 1) signaling and reduced autophagy. TSC1, TSC2, along with TBC1D7 form a complex which regulates mTORC1 via its obligate activator Rheb—a small GTPase. mTORC1 is the master integrator of specific nutrient and growth signals and controls cell growth, metabolism, and is a negative regulator of autophagy. mTORC1 is activated on the surface of the lysosomes by GTP-Rheb (but not GDP-Rheb). TSC complex partially regulates Rheb via the GTPase-activating protein (GAP) function of TSC2. The strongest regulatory role of TSC complex, however, is to physically bind with Rheb and prevent its interaction and subsequent activation of mTORC1.

Currently, the only treatment for TSC patients is mTOR inhibitors such as everolimus which have significant side effects. mTOR exists in another multi-subunit complex, mTORC2, whose functions are less well understood. mTOR kinase inhibitors leads to disassembly of mTORC2 and may cause cell death amongst other. Our novel data shows that calcium and integrin binding protein 2 (CIB2) regulates mTORC1 (but not mTORC2) activity via direct binding to GDP-Rheb (inactive state). Further, it is shown that CIB2 regulates autophagy flux in multiple cell types. To our knowledge, CIB2 is the first protein shown to bind more strongly to the inactive state of Rheb and hence acts downstream of TSC to modulate mTORC1 signaling specifically. Based on our data, we expect that in TSC2 mutant/null cells, CIB2 can down-regulate the hyper-activated mTORC1 signaling and improve autophagy flux.

1. Elucidate the mechanism of CIB2 mediated-mTORC1 activity modulation Based on data, it is expected that CIB2, via its interaction with Rheb, modulates mTORC1 activity. The interaction of endogenous CIB2 with endogenous Rheb can be confirmed, e.g., by co-immunoprecipitation assays. Further, whether CIB2 can interact with other members of the mTORC1-TSC-Rheb axis can be tested, specifically the tuberous sclerosis complex (TSC1 and TSC2), mTOR, and mTORC1 specific subunit Raptor, as described herein and using known methods. Further, CRISPR-mediated Cib2 knockout mouse model has been generated and validated. Mouse embryonic fibroblasts (MEFs) can be generated from it to provide robust tools to gain mechanistic insights into mTORC1 signaling in CIB2 context, and TSC localization and phosphorylation state.

2. Assess the impact of over-expression of CIB2 in TSC2 null or patient-derived TSC2 mutant cell lines, on mTORC1 activity and autophagy flux. In HEK293 cells, over-expression of CIB2 leads to reduced mTORC1 activity under basal conditions. TSC2 null MEFs or patient-derived cell line (Lymphangioleiomyomatosis 621-101 cell-line) with variants in TSC2 are validated and have been shown to have hyperactive mTORC1 signaling and reduced autophagy flux. It is expected that over-expressing CIB2 in TSC null/mutant context will reduce the aberrant activity of mTORC1. Further, our data showed that retinal pigment epithelium cells lacking CIB2, in vivo, have markedly reduced autophagy flux and autophagy/lysosomal proteins. Previous research has shown that autophagy is essential for tumor cell survival in TSC. Hence the autophagy flux in TSC2 null/mutant context can be assessed. These novel data will facilitate further studies to assess the effects of CIB2 over-expression in TSC pre-clinical animal models.

Current treatment options for TSC patients is very limited and most of them have serious side effects. Deciphering the impact of CIB2 over-expression is a critical step towards the development of actual therapies for the treatment and/or mitigation of this debilitating, lifelong disorder.

Example 3. Exogenous Expression of CIB2 is Sufficient to Reduce Overactive mTORC1 Signaling Functional Testing after Gene Delivery:

1 mth old mice received subretinal injections of CIB2-IRES-AcGFP or control eGFP viral vectors. 4 weeks after injections, the mice underwent functional electroretinogram (ERG) evaluation, optical coherence tomography (OCT) evaluation to assess retinal morphology. Finally we assessed for mTORC1 inhibition using western blots and immunofluorescence experiments on mice eyes.

In FIG. 19, it is shown that RPE-specific Cib2$^{KO}$ mice were subretinally injected with 1 μl of Anc80-CIB2-IRES-AcGFP (top panel) or Anc80-eGFP virus (bottom panel). 1-2 weeks after injection, the mice were starved of food for 24 hrs to induce in vivo autophagy. After enucleating the eyes, the retina was separated from the RPE/choroid. RPE/choroid whole mounts were stained for phospho-S6K1 (direct target of mTORC1). The photomicrographs show higher p-S6K1 in RPE cells from mice injected with GFP virus (control) as compared to CIB2-IRES-GFP, suggesting exogenous expression of CIB2 is sufficient to reduce overactive mTORC1 signaling. See FIG. 19.

Viral Vector Construction

Mouse Cib2 gene (NM_019686.6), was cloned into the AAV vector CMV-GFP, using the Not I and Bgl II enzymes to remove the GFP and WPRE sequences from the CMV-eGFP virus and replacing with CIB2-IRES-AcGFP cDNA. The AAV plasmid was packed, by Harvard University Vector Core, into the Anc80 capsid. See FIGS. 17 and 18. The viral titres are shown below:

Anc80 AAV.CMV.Cib2-IRES-AcGFP: 1.81 E+12 GC/ml
Anc80 AAV.CMV.eGFP.WPRE: 4.77 E+12 GC/ml

Protocol for Subretinal Injections

Surgical Preparation

Anesthetized the mouse with 100 mg/ml ketamine and 10 mg/ml xylazine (10 µl/10 g body weight) of mice.

Administer anesthesia to a depth such that mouse has no toe pinch.

Dilate the eyes with Tropicamide 1% solution.

Sterile instruments with 70% ethanol prior to use.

Injection Site Preparation

Prepare NaNOFIL syringe 10 ul (World precision instrument, Nanofil) with 35GA blunt needle (WPI #NF35BL), with 1 µl of Cib2 virus.

Positioned the mouse so the eyes facing up and clearly visible in dissecting microscope.

Using a dissecting microscope gently stretch the skin on both sides of the eye so the eye pops slightly up out of the socket. Make sure not to grasp the mouse too close to the throat.

Gently pinch the temporal conjunctiva with tipped forceps (COLIBI Suturing 7.5 C, #5550060 FT, WPI company).

Sclerotomy and Subretinal Injection.

Make a small cut in the tissue to expose the scleral tissue, using curved vannas scissors Make an incision at injection site using 23G sterile syringe. This incision should only be large enough to allow the tip of NaNOFIL needle to pass through the sclera.

Insert NaNOFIL syringe parallel to the retina inject desired volume.

Depress the plunger slowly over 30 sec without moving the needle and with even pressure. Wait for 1 min after injection, to avoid backflow.

Put the eye back in socket, clean with sterile eyewash, and ensure the eye has rotated back to its normal position.

Put methylcellulose on both eyes to prevent dehydration and to minimize anesthetic induced cataract.

Note:

1. IMPORTANT: When the needle is in subretinal space (between the photoreceptors and retinal pigment epithelium (RPE), a slight resistance should be felt while depressing the plunger. If you do not feel resistance, you have gone too deep and pierced the RPE or not deep enough and are not in the subretinal space.

What is claimed is:

1. A method for treating a disease, condition or disorder by down-regulating mTORC1 signaling in a subject, comprising administering to the subject an effective amount of one or more compositions that increase activity of CIB2 or a biologically active fragment or variant thereof in the subject, wherein the subject is in need of treatment for the disease, condition, or disorder selected from the group consisting of macular degeneration and age-related macular degeneration, thereby downregulating mTORC1 signaling in the subject.

2. The method of claim 1, wherein the disease, condition, or disorder is age-related macular degeneration.

3. The method of claim 1, wherein the method increases canonical and non-canonical autophagy and/or phagolysosomal digestion in cells.

4. The method of claim 3 wherein the cells comprise retinal pigment epithelium.

5. The method of claim 1, wherein the one or more compositions comprise a nucleic acid comprising a sequence encoding CIB2 or a biologically active fragment or variant thereof.

6. The method of claim 5, wherein the nucleic acid is provided by a viral vector.

7. The method of claim 6, wherein the viral vector comprises an adeno-associated (AAV) donor vector.

8. The method of claim 1, wherein the one or more compositions comprise at least one non-naturally occurring nuclease, wherein the nuclease cleaves a sequence in a genome of a cell in the subject, such that the CIB2 or a biologically active fragment or variant thereof is integrated into the genome of the cell in the subject.

9. The method of claim 8, wherein the nuclease is administered as a nucleic acid and is expressed by the cell.

10. The method of claim 9, wherein the nuclease is administered as a polypeptide.

11. The method of claim 8, wherein the vector is administered prior to or after the administration of the at least one nuclease.

12. The method of claim 8, wherein the vector is administered together with the at least one nuclease.

13. The method of claim 8, wherein the at least one nuclease is selected from the group consisting of a zinc finger nuclease (ZFN), a TALE nuclease (TALEN), a CRISPR/Cas nuclease system and combinations thereof.

14. The method of claim 1, wherein the one or more compositions comprise a polypeptide comprising CIB2 or a biologically active fragment or variant thereof.

15. The method of claim 14, wherein the one or more compositions comprise an agent that facilitates uptake of the polypeptide into cells.

16. The method of claim 15, wherein the agent comprises one or more cationic peptides, amphipathic molecules, lipid-based carriers or combinations thereof.

17. The method of claim 15, wherein the polypeptide is associated with a protein transduction domain.

18. The method of claim 17, wherein the polypeptide is a fusion protein comprising the protein transduction domain.

19. The method of claim 1, wherein the method further comprises administering an effective amount of an additional therapeutic agent.

20. The method of claim 5, wherein the one or more compositions comprise a nucleic acid comprising a sequence encoding CIB2.

* * * * *

SEQUENCE LISTING

<160> NUMBER OF SEQ ID NOS: 57

<210> SEQ ID NO 1
<211> LENGTH: 187
<212> TYPE: PRT
<213> ORGANISM: Homo sapiens

<400> SEQUENCE: 1

```
Met Gly Asn Lys Gln Thr Ile Phe Thr Glu Glu Gln Leu Asp Asn Tyr
1               5                   10                  15

Gln Asp Cys Thr Phe Phe Asn Lys Lys Asp Ile Leu Lys Leu His Ser
            20                  25                  30

Arg Phe Tyr Glu Leu Ala Pro Asn Leu Val Pro Met Asp Tyr Arg Lys
        35                  40                  45

Ser Pro Ile Val His Val Pro Met Ser Leu Ile Ile Gln Met Pro Glu
    50                  55                  60

Leu Arg Glu Asn Pro Phe Lys Glu Arg Ile Val Ala Ala Phe Ser Glu
65                  70                  75                  80

Asp Gly Glu Gly Asn Leu Thr Phe Asn Asp Phe Val Asp Met Phe Ser
                85                  90                  95

Val Leu Cys Glu Ser Ala Pro Arg Glu Leu Lys Ala Asn Tyr Ala Phe
            100                 105                 110

Lys Ile Tyr Asp Phe Asn Thr Asp Asn Phe Ile Cys Lys Glu Asp Leu
        115                 120                 125

Glu Leu Thr Leu Ala Arg Leu Thr Lys Ser Glu Leu Asp Glu Glu Glu
    130                 135                 140

Val Val Leu Val Cys Asp Lys Val Ile Glu Glu Ala Asp Leu Asp Gly
145                 150                 155                 160
```

-continued

```
Asp Gly Lys Leu Gly Phe Ala Asp Phe Glu Asp Met Ile Ala Lys Ala
                165                 170                 175

Pro Asp Phe Leu Ser Thr Phe His Ile Arg Ile
            180                 185

<210> SEQ ID NO 2
<211> LENGTH: 187
<212> TYPE: PRT
<213> ORGANISM: Mus musculus

<400> SEQUENCE: 2

Met Gly Asn Lys Gln Thr Ile Phe Thr Glu Glu Gln Leu Asp Asn Tyr
1               5                   10                  15

Gln Asp Cys Thr Phe Phe Asn Lys Lys Asp Ile Leu Lys Leu His Ala
            20                  25                  30

Arg Phe Tyr Glu Leu Ala Pro Asn Leu Val Pro Met Asp Tyr Arg Lys
        35                  40                  45

Ser Pro Ile Val His Val Pro Met Ser Leu Ile Ile Gln Met Pro Glu
    50                  55                  60

Leu Arg Glu Asn Pro Phe Lys Glu Arg Ile Val Glu Ala Phe Ser Glu
65                  70                  75                  80

Asp Gly Glu Gly Asn Leu Thr Phe Asn Asp Phe Val Asp Met Phe Ser
                85                  90                  95

Val Leu Cys Glu Ser Ala Pro Arg Glu Leu Lys Ala Asn Tyr Ala Phe
            100                 105                 110

Lys Ile Tyr Asp Phe Asn Thr Asp Asn Phe Ile Cys Lys Glu Asp Leu
            115                 120                 125

Glu Met Thr Leu Ala Arg Leu Thr Lys Ser Glu Leu Glu Glu Asp Glu
        130                 135                 140

Val Val Leu Val Cys Asp Lys Val Ile Glu Glu Ala Asp Leu Asp Gly
145                 150                 155                 160

Asp Gly Lys Leu Gly Phe Ala Asp Phe Glu Asp Met Ile Ala Lys Ala
                165                 170                 175

Pro Asp Phe Leu Ser Thr Phe His Ile Arg Ile
            180                 185

<210> SEQ ID NO 3
<211> LENGTH: 564
<212> TYPE: DNA
<213> ORGANISM: Homo sapiens

<400> SEQUENCE: 3
atggggaaca agcagaccat cttcaccgaa gagcagctag acaactacca ggactgcacc      60
ttcttcaata agaaggacat cctcaagctg cattcgcgat ctatgagct ggcccccaac      120 ctcgtcccaa tggactacag gaagagcccc atcgtccacg tgcccatgag cctcatcatc     180
cagatgccag agctccggga gaatcccttc aaagaaagga tcgtggcggc gttttccgag     240
gatggtgagg ggaacctcac tttcaacgac tttgtggaca tgtttccgt gctctgcgag      300 tcggctcccc gagagctcaa ggcaaactat gccttcaaga tctatgactt caacactgac     360
aacttcatct gcaaggagga cctggagctg acgctggccc ggctcactaa gtcagagctg     420
gatgaggagg aggtggtgct tgtgtgcgac aaggtcattg aggaggctga cttggacggt     480
gacggcaagc tgggctttgc tgacttcgag gacatgattg ccaaggcccc tgacttcctc     540
agcactttcc acatccggat ctga                                            564
```

```
<210> SEQ ID NO 4
<211> LENGTH: 564
<212> TYPE: DNA
<213> ORGANISM: Mus musculus

<400> SEQUENCE: 4
atggggaaca agcagaccat cttcactgaa gagcagctgg acaactacca ggactgcact        60
ttcttcaata agaaggacat cctcaagctt catgcacggt tctatgagct ggctcccaac       120
ctcgtcccga tggactacag gaagagtccc atcgtccatg tacccatgag cctcatcatt       180
cagatgccgg agctccggga gaatcccttc aaagagagga ttgtggaggc tttctccgag       240
gatggcgagg ggaacctcac cttcaatgac tttgtggaca tgttctctgt gctctgcgaa       300
tcagcgcctc gggagctcaa ggcaaactat gccttcaaga tctatgactt caacactgac       360
aatttcatct gtaaagaaga cttagagatg acgctggccc gactcaccaa gtctgagttg       420
gaagaggatg aggtagtgct tgtgtgtgac aaagtcattg aagaggctga cctggatggt       480
gacggcaagc tgggctttgc tgactttgag gacatgatcg ccaaggcccc tgattttctc       540
agcaccttcc acattcgaat ctga                                              564

<210> SEQ ID NO 5
<211> LENGTH: 22
<212> TYPE: PRT
<213> ORGANISM: artificial sequence
<220> FEATURE:
<223> OTHER INFORMATION: transduction domain

<400> SEQUENCE: 5

Arg Arg Arg Arg Arg Arg Arg Arg Arg Pro Ser Ala Ser Tyr Pro Tyr
1               5                   10                  15

Asp Val Pro Asp Tyr Ala
            20

<210> SEQ ID NO 6
<211> LENGTH: 10
<212> TYPE: PRT
<213> ORGANISM: artificial sequence
<220> FEATURE:
<223> OTHER INFORMATION: transduction domain

<400> SEQUENCE: 6

Gly Arg Lys Lys Arg Arg Gln Arg Arg Arg
1               5                   10

<210> SEQ ID NO 7
<211> LENGTH: 11
<212> TYPE: PRT
<213> ORGANISM: artificial sequence
<220> FEATURE:
<223> OTHER INFORMATION: transduction domain

<400> SEQUENCE: 7

Tyr Gly Arg Lys Lys Arg Arg Gln Arg Arg Arg
1               5                   10

<210> SEQ ID NO 8
<211> LENGTH: 7
<212> TYPE: PRT
<213> ORGANISM: artificial sequence
<220> FEATURE:
<223> OTHER INFORMATION: transduction domain

<400> SEQUENCE: 8
```

```
Gly Arg Lys Lys Arg Arg Gln
1               5

<210> SEQ ID NO 9
<211> LENGTH: 16
<212> TYPE: PRT
<213> ORGANISM: artificial sequence
<220> FEATURE:
<223> OTHER INFORMATION: transduction domain

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 7
<212> TYPE: PRT
<213> ORGANISM: artificial sequence
<220> FEATURE:
<223> OTHER INFORMATION: transduction domain

<400> SEQUENCE: 10

Arg Arg Met Lys Trp Lys Lys
1               5

<210> SEQ ID NO 11
<211> LENGTH: 16
<212> TYPE: PRT
<213> ORGANISM: artificial sequence
<220> FEATURE:
<223> OTHER INFORMATION: transduction domain

<400> SEQUENCE: 11

Arg Arg Trp Arg Arg Trp Trp Arg Arg Trp Trp Arg Arg Trp Arg Arg
1               5                   10                  15

<210> SEQ ID NO 12
<211> LENGTH: 18
<212> TYPE: PRT
<213> ORGANISM: artificial sequence
<220> FEATURE:
<223> OTHER INFORMATION: transduction domain

<400> SEQUENCE: 12

Arg Gly Gly Arg Leu Ser Tyr Ser Arg Arg Arg Phe Ser Thr Ser Thr
1               5                   10                  15

Gly Arg

<210> SEQ ID NO 13
<211> LENGTH: 9
<212> TYPE: PRT
<213> ORGANISM: artificial sequence
<220> FEATURE:
<223> OTHER INFORMATION: transduction domain

<400> SEQUENCE: 13

Arg Lys Lys Arg Arg Gln Arg Arg Arg
1               5

<210> SEQ ID NO 14
<211> LENGTH: 11
<212> TYPE: PRT
<213> ORGANISM: artificial sequence
<220> FEATURE:
<223> OTHER INFORMATION: transduction domain

<400> SEQUENCE: 14
```

-continued

```
Tyr Ala Arg Ala Ala Ala Arg Gln Ala Arg Ala
1               5                   10

<210> SEQ ID NO 15
<211> LENGTH: 8
<212> TYPE: PRT
<213> ORGANISM: artificial sequence
<220> FEATURE:
<223> OTHER INFORMATION: transduction domain

<400> SEQUENCE: 15

Arg Arg Arg Arg Arg Arg Arg Arg
1               5

<210> SEQ ID NO 16
<211> LENGTH: 8
<212> TYPE: PRT
<213> ORGANISM: artificial sequence
<220> FEATURE:
<223> OTHER INFORMATION: transduction domain

<400> SEQUENCE: 16

Lys Lys Lys Lys Lys Lys Lys Lys
1               5

<210> SEQ ID NO 17
<211> LENGTH: 27
<212> TYPE: PRT
<213> ORGANISM: artificial sequence
<220> FEATURE:
<223> OTHER INFORMATION: transduction domain
<220> FEATURE:
<221> NAME/KEY: misc_feature
<222> LOCATION: (25)..(25)
<223> OTHER INFORMATION: Xaa can be any naturally occurring amino acid

<400> SEQUENCE: 17

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 18
<211> LENGTH: 16
<212> TYPE: PRT
<213> ORGANISM: artificial sequence
<220> FEATURE:
<223> OTHER INFORMATION: transduction domain

<400> SEQUENCE: 18

Ser Arg Arg His His Cys Arg Ser Lys Ala Lys Arg Ser Arg His His
1               5                   10                  15

<210> SEQ ID NO 19
<211> LENGTH: 11
<212> TYPE: PRT
<213> ORGANISM: artificial sequence
<220> FEATURE:
<223> OTHER INFORMATION: transduction domain

<400> SEQUENCE: 19

Asn Arg Ala Arg Arg Asn Arg Arg Arg Val Arg
1               5                   10

<210> SEQ ID NO 20
<211> LENGTH: 15
```

```
<212> TYPE: PRT
<213> ORGANISM: artificial sequence
<220> FEATURE:
<223> OTHER INFORMATION: transduction domain

<400> SEQUENCE: 20

Arg Gln Leu Arg Ile Ala Gly Arg Arg Leu Arg Gly Arg Ser Arg
1               5                   10                  15

<210> SEQ ID NO 21
<211> LENGTH: 13
<212> TYPE: PRT
<213> ORGANISM: artificial sequence
<220> FEATURE:
<223> OTHER INFORMATION: transduction domain

<400> SEQUENCE: 21

Lys Leu Ile Lys Gly Arg Thr Pro Ile Lys Phe Gly Lys
1               5                   10

<210> SEQ ID NO 22
<211> LENGTH: 10
<212> TYPE: PRT
<213> ORGANISM: artificial sequence
<220> FEATURE:
<223> OTHER INFORMATION: transduction domain

<400> SEQUENCE: 22

Arg Arg Ile Pro Asn Arg Arg Pro Arg Arg
1               5                   10

<210> SEQ ID NO 23
<211> LENGTH: 18
<212> TYPE: PRT
<213> ORGANISM: artificial sequence
<220> FEATURE:
<223> OTHER INFORMATION: transduction domain

<400> SEQUENCE: 23

Lys Leu Ala Leu Lys Leu Ala Leu Lys Ala Leu Lys Ala Ala Leu Lys
1               5                   10                  15

Leu Ala

<210> SEQ ID NO 24
<211> LENGTH: 14
<212> TYPE: PRT
<213> ORGANISM: artificial sequence
<220> FEATURE:
<223> OTHER INFORMATION: transduction domain

<400> SEQUENCE: 24

Lys Leu Ala Lys Leu Ala Lys Lys Leu Ala Lys Leu Ala Lys
1               5                   10

<210> SEQ ID NO 25
<211> LENGTH: 27
<212> TYPE: PRT
<213> ORGANISM: artificial sequence
<220> FEATURE:
<223> OTHER INFORMATION: transduction domain

<400> SEQUENCE: 25

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25
```

<210> SEQ ID NO 26
<211> LENGTH: 21
<212> TYPE: PRT
<213> ORGANISM: artificial sequence
<220> FEATURE:
<223> OTHER INFORMATION: transduction domain

<400> SEQUENCE: 26

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 27
<211> LENGTH: 20
<212> TYPE: PRT
<213> ORGANISM: artificial sequence
<220> FEATURE:
<223> OTHER INFORMATION: transduction domain

<400> SEQUENCE: 27

Leu Lys Lys Leu Leu Lys Lys Leu Leu Lys Lys Leu Leu Lys Lys Leu
1               5                   10                  15

Leu Lys Lys Leu
            20

<210> SEQ ID NO 28
<211> LENGTH: 34
<212> TYPE: PRT
<213> ORGANISM: artificial sequence
<220> FEATURE:
<223> OTHER INFORMATION: transduction domain

<400> SEQUENCE: 28

Gln Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 29
<211> LENGTH: 23
<212> TYPE: PRT
<213> ORGANISM: artificial sequence
<220> FEATURE:
<223> OTHER INFORMATION: transduction domain

<400> SEQUENCE: 29

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 30
<211> LENGTH: 26
<212> TYPE: PRT
<213> ORGANISM: artificial sequence
<220> FEATURE:
<223> OTHER INFORMATION: transduction domain

<400> SEQUENCE: 30

Ala Ala Val Ala Leu Leu Pro Ala Val Leu Leu Ala Leu Leu Ala Pro
1               5                   10                  15

```
Ala Ala Ala Asn Tyr Lys Lys Pro Lys Leu
            20                  25
```

<210> SEQ ID NO 31
<211> LENGTH: 28
<212> TYPE: PRT
<213> ORGANISM: artificial sequence
<220> FEATURE:
<223> OTHER INFORMATION: transduction domain

<400> SEQUENCE: 31

```
Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25
```

<210> SEQ ID NO 32
<211> LENGTH: 24
<212> TYPE: PRT
<213> ORGANISM: artificial sequence
<220> FEATURE:
<223> OTHER INFORMATION: transduction domain

<400> SEQUENCE: 32

```
Leu Gly Thr Tyr Thr Gln Asp Phe Asn Lys Phe His Thr Phe Pro Gln
1               5                   10                  15

Thr Ala Ile Gly Val Gly Ala Pro
            20
```

<210> SEQ ID NO 33
<211> LENGTH: 26
<212> TYPE: PRT
<213> ORGANISM: artificial sequence
<220> FEATURE:
<223> OTHER INFORMATION: transduction domain
<220> FEATURE:
<221> NAME/KEY: misc_feature
<222> LOCATION: (24)..(24)
<223> OTHER INFORMATION: Xaa can be any naturally occurring amino acid

<400> SEQUENCE: 33

```
Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25
```

<210> SEQ ID NO 34
<211> LENGTH: 14
<212> TYPE: PRT
<213> ORGANISM: artificial sequence
<220> FEATURE:
<223> OTHER INFORMATION: transduction domain

<400> SEQUENCE: 34

```
Pro Pro Pro Pro Pro Pro Pro Pro Pro Pro Pro Pro Pro Pro
1               5                   10
```

<210> SEQ ID NO 35
<211> LENGTH: 18
<212> TYPE: PRT
<213> ORGANISM: artificial sequence
<220> FEATURE:
<223> OTHER INFORMATION: transduction domain

<400> SEQUENCE: 35

```
Val Arg Leu Pro Pro Pro Val Arg Leu Pro Pro Pro Val Arg Leu Pro
1               5                   10                  15

Pro Pro

<210> SEQ ID NO 36
<211> LENGTH: 10
<212> TYPE: PRT
<213> ORGANISM: artificial sequence
<220> FEATURE:
<223> OTHER INFORMATION: transduction domain

<400> SEQUENCE: 36

Pro Arg Pro Leu Pro Pro Pro Arg Pro Gly
1               5                   10

<210> SEQ ID NO 37
<211> LENGTH: 30
<212> TYPE: PRT
<213> ORGANISM: artificial sequence
<220> FEATURE:
<223> OTHER INFORMATION: transduction domain

<400> SEQUENCE: 37

Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
                20                  25                  30

<210> SEQ ID NO 38
<211> LENGTH: 21
<212> TYPE: PRT
<213> ORGANISM: artificial sequence
<220> FEATURE:
<223> OTHER INFORMATION: transduction domain

<400> SEQUENCE: 38

Thr Arg Ser Ser Arg Ala Gly Leu Gln Phe Pro Val Gly Arg Val His
1               5                   10                  15

Arg Leu Leu Arg Lys
                20

<210> SEQ ID NO 39
<211> LENGTH: 23
<212> TYPE: PRT
<213> ORGANISM: artificial sequence
<220> FEATURE:
<223> OTHER INFORMATION: transduction domain

<400> SEQUENCE: 39

Gly Ile Gly Lys Phe Leu His Ser Ala Lys Lys Phe Gly Lys Ala Phe
1               5                   10                  15

Val Gly Glu Ile Met Asn Ser
                20

<210> SEQ ID NO 40
<211> LENGTH: 37
<212> TYPE: PRT
<213> ORGANISM: artificial sequence
<220> FEATURE:
<223> OTHER INFORMATION: transduction domain

<400> SEQUENCE: 40

Lys Trp Lys Leu Phe Lys Lys Ile Glu Lys Val Gly Gln Asn Ile Arg
1               5                   10                  15
```

```
Asp Gly Ile Ile Lys Ala Gly Pro Ala Val Ala Val Val Gly Gln Ala
                20              25              30

Thr Gln Ile Ala Lys
        35

<210> SEQ ID NO 41
<211> LENGTH: 28
<212> TYPE: PRT
<213> ORGANISM: artificial sequence
<220> FEATURE:
<223> OTHER INFORMATION: transduction domain

<400> SEQUENCE: 41

Ala Leu Trp Met Thr Leu Leu Lys Lys Val Leu Lys Ala Ala Ala Lys
1               5               10              15

Ala Ala Leu Asn Ala Val Leu Val Gly Ala Asn Ala
                20              25

<210> SEQ ID NO 42
<211> LENGTH: 26
<212> TYPE: PRT
<213> ORGANISM: artificial sequence
<220> FEATURE:
<223> OTHER INFORMATION: transduction domain

<400> SEQUENCE: 42

Gly Ile Gly Ala Val Leu Lys Val Leu Thr Thr Gly Leu Pro Ala Leu
1               5               10              15

Ile Ser Trp Ile Lys Arg Lys Arg Gln Gln
                20              25

<210> SEQ ID NO 43
<211> LENGTH: 14
<212> TYPE: PRT
<213> ORGANISM: artificial sequence
<220> FEATURE:
<223> OTHER INFORMATION: transduction domain

<400> SEQUENCE: 43

Ile Asn Leu Lys Ala Leu Ala Ala Leu Ala Lys Lys Ile Leu
1               5               10

<210> SEQ ID NO 44
<211> LENGTH: 33
<212> TYPE: PRT
<213> ORGANISM: artificial sequence
<220> FEATURE:
<223> OTHER INFORMATION: transduction domain

<400> SEQUENCE: 44

Gly Phe Phe Ala Leu Ile Pro Lys Ile Ile Ser Ser Pro Leu Pro Lys
1               5               10              15

Thr Leu Leu Ser Ala Val Gly Ser Ala Leu Gly Gly Ser Gly Gly Gln
                20              25              30

Glu

<210> SEQ ID NO 45
<211> LENGTH: 15
<212> TYPE: PRT
<213> ORGANISM: artificial sequence
<220> FEATURE:
<223> OTHER INFORMATION: transduction domain

<400> SEQUENCE: 45
```

-continued

```
Leu Ala Lys Trp Ala Leu Lys Gln Gly Phe Ala Lys Leu Lys Ser
1               5                   10                  15

<210> SEQ ID NO 46
<211> LENGTH: 27
<212> TYPE: PRT
<213> ORGANISM: artificial sequence
<220> FEATURE:
<223> OTHER INFORMATION: transduction domain
<220> FEATURE:
<221> NAME/KEY: misc_feature
<222> LOCATION: (23)..(23)
<223> OTHER INFORMATION: Xaa can be any naturally occurring amino acid

<400> SEQUENCE: 46

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 47
<211> LENGTH: 41
<212> TYPE: PRT
<213> ORGANISM: artificial sequence
<220> FEATURE:
<223> OTHER INFORMATION: transduction domain

<400> SEQUENCE: 47

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

Ala Asn Leu Val Pro Arg Thr Glu Ser
        35                  40

<210> SEQ ID NO 48
<211> LENGTH: 18
<212> TYPE: PRT
<213> ORGANISM: artificial sequence
<220> FEATURE:
<223> OTHER INFORMATION: transduction domain

<400> SEQUENCE: 48

Pro Ala Trp Arg Lys Ala Phe Arg Trp Ala Trp Arg Met Leu Lys Lys
1               5                   10                  15

Ala Ala

<210> SEQ ID NO 49
<211> LENGTH: 18
<212> TYPE: PRT
<213> ORGANISM: artificial sequence
<220> FEATURE:
<223> OTHER INFORMATION: transduction domain

<400> SEQUENCE: 49

Lys Leu Lys Leu Lys Leu Lys Leu Lys Leu Lys Leu Lys Leu Lys Leu
1               5                   10                  15

Lys Leu

<210> SEQ ID NO 50
<211> LENGTH: 18
<212> TYPE: PRT
<213> ORGANISM: artificial sequence
<220> FEATURE:
<223> OTHER INFORMATION: transduction domain
```

-continued

<400> SEQUENCE: 50

Leu Leu Ile Leu Leu Arg Arg Arg Ile Arg Lys Gln Ala Asn Ala His
1               5                   10                  15

Ser Lys

<210> SEQ ID NO 51
<211> LENGTH: 23
<212> TYPE: PRT
<213> ORGANISM: artificial sequence
<220> FEATURE:
<223> OTHER INFORMATION: transduction domain

<400> SEQUENCE: 51

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 52
<211> LENGTH: 66
<212> TYPE: DNA
<213> ORGANISM: artificial sequence
<220> FEATURE:
<223> OTHER INFORMATION: transduction domain

<400> SEQUENCE: 52
agacgaaggc gcagacggag gcgtagaccg tctgccagct atccatacga cgtgcctgac      60
tacgcg                                                                 66

<210> SEQ ID NO 53
<211> LENGTH: 30
<212> TYPE: DNA
<213> ORGANISM: artificial sequence
<220> FEATURE:
<223> OTHER INFORMATION: transduction domain

<400> SEQUENCE: 53
ggccgtaaaa aacgccgtca acgccgccgt                                       30

<210> SEQ ID NO 54
<211> LENGTH: 33
<212> TYPE: DNA
<213> ORGANISM: artificial sequence
<220> FEATURE:
<223> OTHER INFORMATION: transduction domain

<400> SEQUENCE: 54
tatggccgta aaaacgccg tcaacgccgc cgt                                    33

<210> SEQ ID NO 55
<211> LENGTH: 21
<212> TYPE: DNA
<213> ORGANISM: artificial sequence
<220> FEATURE:
<223> OTHER INFORMATION: transduction domain

<400> SEQUENCE: 55
ggccgtaaaa aacgccgtca a                                                21

<210> SEQ ID NO 56
<211> LENGTH: 7
<212> TYPE: PRT
<213> ORGANISM: artificial sequence -continued

```
<220> FEATURE:
<223> OTHER INFORMATION: vector insertion sequence

<400> SEQUENCE: 56

Leu Gly Glu Thr Thr Arg Pro
1               5

<210> SEQ ID NO 57
<211> LENGTH: 9
<212> TYPE: PRT
<213> ORGANISM: artificial sequence
<220> FEATURE:
<223> OTHER INFORMATION: vector insertion sequence

<400> SEQUENCE: 57

Leu Ala Leu Gly Glu Thr Thr Arg Pro
1               5
```